US010738346B2

(12) United States Patent
Lukhtanov et al.

(10) Patent No.: US 10,738,346 B2
(45) Date of Patent: Aug. 11, 2020

(54) NITRODIARYLETHENES AS FLUORESCENCE QUENCHERS FOR NUCLEIC ACID PROBES

(71) Applicant: ELITechGroup, Inc., Logan, UT (US)

(72) Inventors: Eugeny A. Lukhtanov, Bothell, WA (US); Noah Scarr, Seattle, WA (US)

(73) Assignee: ELITECHGROUP, INC., Logan, UT (US)

(*) Notice: Subject to any disclaimer, the term of this patent is extended or adjusted under 35 U.S.C. 154(b) by 0 days.

(21) Appl. No.: 15/909,096

(22) Filed: Mar. 1, 2018

(65) Prior Publication Data
US 2018/0258471 A1    Sep. 13, 2018

Related U.S. Application Data

(60) Provisional application No. 62/469,063, filed on Mar. 9, 2017.

(51) Int. Cl.
C07C 205/35    (2006.01)
C07C 205/57    (2006.01)
C07C 229/18    (2006.01)
C09B 23/14     (2006.01)
C07D 207/12    (2006.01)
C07D 207/46    (2006.01)
C07D 213/55    (2006.01)
C07D 401/10    (2006.01)
C07F 9/572     (2006.01)
C07H 21/04     (2006.01)
C12Q 1/6816    (2018.01)
G01N 21/64     (2006.01)

(52) U.S. Cl.
CPC .......... C12Q 1/6816 (2013.01); C07C 205/35 (2013.01); C07C 205/57 (2013.01); C07C 229/18 (2013.01); C07D 207/12 (2013.01); C07D 207/46 (2013.01); C07D 213/55 (2013.01); C07D 401/10 (2013.01); C07F 9/572 (2013.01); C07H 21/04 (2013.01); C09B 23/141 (2013.01); C09B 23/148 (2013.01); G01N 21/6428 (2013.01); G01N 2021/6432 (2013.01)

(58) Field of Classification Search
CPC combination set(s) only.
See application file for complete search history.

(56) References Cited

FOREIGN PATENT DOCUMENTS

WO    2002/099141    12/2002
WO    2004/106358    9/2004

OTHER PUBLICATIONS

Korbecka et al. Dyes and Pigments 2017, 140, 166-168. (Year: 2017).*
Prukala J. Het. Chem. 2006, 43, 337. (Year: 2006).*
Barton et al. J. Chem. Soc. Chem. Commun. 1988, 7, 488-489. (Year: 1988).*
Chemical Abstract Service STN Registry No. 52785-57-6 [Entered STN: Nov. 16, 1984]. (Year: 1984).*
Doi et al. "Efficiency of [2+2] photodimerization of various stilbene derivatives within the DNA duplex scaffold." J. Org. Biomolec. Chem. 2015, 13, 4355-4616. (Year: 2015).*
Yang et al. Can. J. Chem. 2013, 91, 1513 (Year: 2013).*
Notification of Transmittal of the International Search Report and the Written Opinion of the International Searching Authority dated Sep. 3, 2018 for PCT/IB2018/000326, issued by the European Patent Office, 18 pages.
Lukhtanov, Eugeny A., "Novel DNA probes with low backgroundandhigh hybridization-triggered fluorescence", Necleic Acids Research, Oxford University Press, vol. 35, No. 5, Jan. 1, 2007, pp. 1-14.
Barton, John W., et al., "A Promising Material for Non-linear Optics: Observation of Second Harmonic Generation from 4-[N-(4-Carboxypentyl)-N-menthylamino]-4'-nitrostilbene-coated Substrates", Journal of the Chemical Society, Chemical Communications, No. 7, Jan. 1, 1988, pp. 488-489.
Schanne-Klein, et al., "Magnetic chiroptical effects in surface second harmonic reflection", Chemical Physics Letters, vol. 338, No. 2-3, Apr. 1, 2001, pp. 159-166.
Prukala, Dorota, "Synthesis and Physicochemical Properties of New Fluorescent Derivatives of Cytosine", Journal of Heterocyclic Chemistry, vol. 43, No. 2, Mar. 1, 2006, pp. 337-344.
Heesemann, Jurgen, "Studies on Monolayers. 1. Surface Tension and Absorption Spectroscopic Measurements of Monolayers of Surface-Active Azo and Stilbene Dyes", Journal of the American Chemical Society, vol. 102, No. 7, Mar. 1, 1980, pp. 2167-2176.
Tian, Feng, et al., "The Effects of Antibodies on Stilbene Excited-State Energetics", Angewandte Chemie International Edition, vol. 45, No. 46, Nov. 27, 2006, pp. 7763-7765.
Gigante, Bárbara, et al., "Systhesis, spectroscopy, photophysics and thermal behaviour of stilbene-based triarylamines with dehydroabietic acid methyl ester moieties", New Journal of Chemistry, vol. 33, No. 4, Jan. 1, 2009, p. 877-885.
Schreiter, Katja, et al., "Novel Periphery-Functionalized Solvatochromic Nitrostilbenes As Precursors for Class II Hybrid Materials", Chemistry of Materials, vol. 22, No. 9, May 11, 2010, pp. 2720-2729.
Korbecka, Izabela, et al., "Novel fluorescent liquid crystal containing azobenzene and stilbene moieties-synthesis, mesogenic and spectroscopic studies", Dyes and Pigments, Elsevier Applied Science Publishers, Barking, GB, vol. 140, Jan. 23, 2017, pp. 166-168.

(Continued)

Primary Examiner — Amanda L. Aguirre
(74) Attorney, Agent, or Firm — Jackson Walker LLP

(57) ABSTRACT

Fluorescence quenching nitrodiarylethene analogs are useful in oligonucleotide conjugates and probes. These analogs, whose absorption spectra are substantially blue-shifted relatively to emission spectra of common fluorophores (such as fluorescein), do not need to rely on spectral overlap of quencher absorbance and fluorophore's emission for their quenching abilities. The oligonucleotide-quencher conjugates may be used in detection methods for nucleic acid targets.

7 Claims, 28 Drawing Sheets

Specification includes a Sequence Listing.

(56) References Cited

OTHER PUBLICATIONS

Notification of Transmittal of the International Preliminary Report on Patentability dated Sep. 19, 2019 from the International Bureau of WIPO containing the Written Opinion of the International Searching Authority—European Patent Office—for International Application No. PCT/IB2018/000326, 10 pages.

\* cited by examiner

Scheme 1

Scheme 2

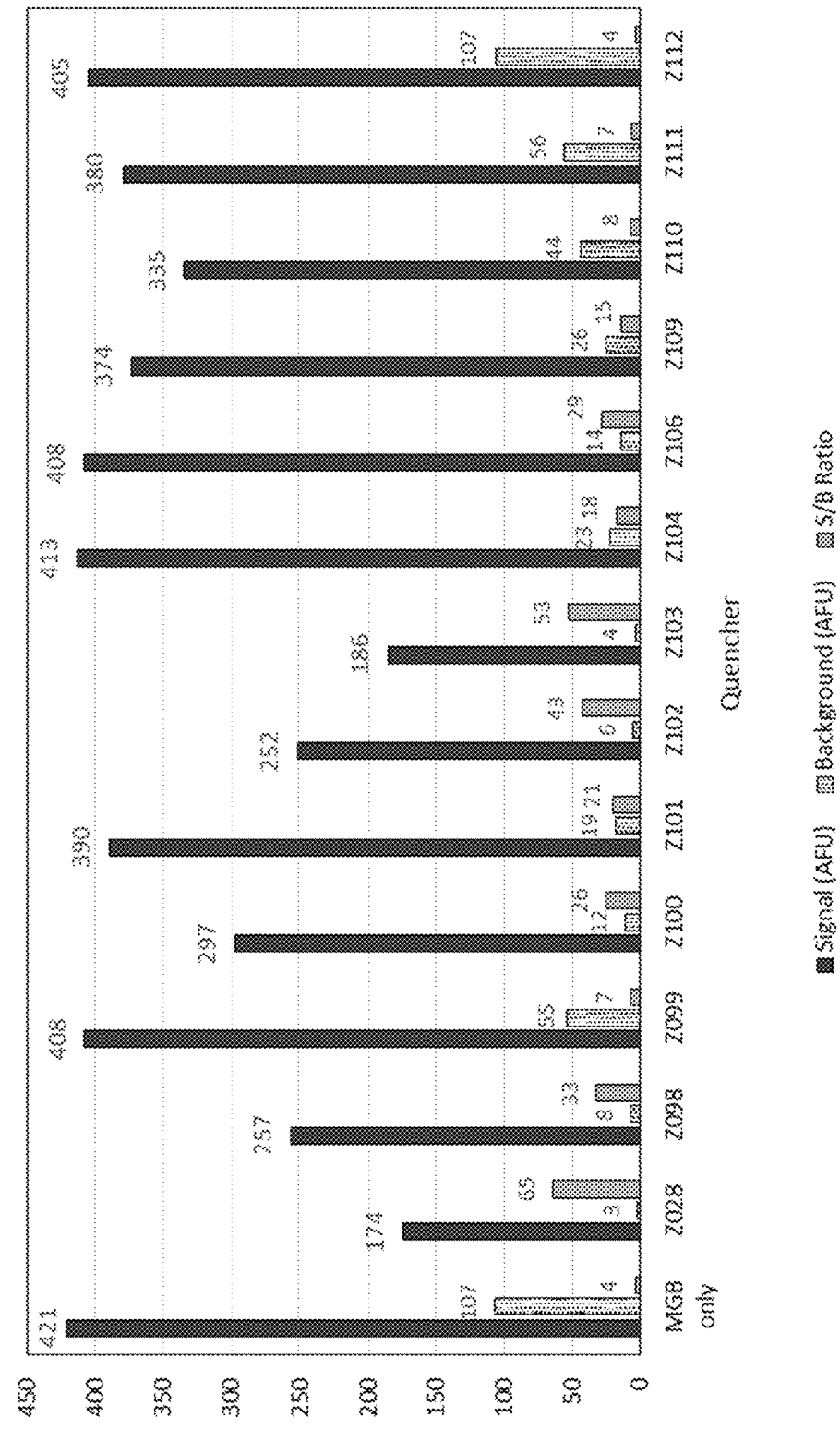

1a R$^1$= -H, R$^2$= -H, R$^3$= -H, X= -N(Me)-

1b R$^1$= -OMe, R$^2$= -H, R$^3$= -OMe, X= -N(Et)-

1c R$^1$+ R$^2$= -CH=CH-, R$^3$= -H, X= -N(Et)-

2a-c

R$^1$ = -H or -OMe

2d R$^1$= -H

2e R$^1$= -OMe

NITRODIARYLETHENES AS FLUORESCENCE QUENCHERS FOR NUCLEIC ACID PROBES

This application claims priority to U.S. Provisional Patent Application No. 62/469,063, entitled "Nitrodiarylethenes as Fluorescence Quenchers for Nucleic Acid Probes," filed Mar. 9, 2017, the entire contents of which are hereby incorporated by reference.

BACKGROUND

This disclosure pertains to oligonucleotide-quencher conjugates with improved fluorescence characteristics, and to reagents suitable for incorporating novel quencher moieties into oligonucleotides. The disclosure also pertains to the use of oligonucleotide-quencher conjugates in detection methods for nucleic acid targets.

Nucleic acid hybridization probes are used for detection and discrimination of closely related nucleic acid targets. Fluorescence is often used to signal the hybridization event. Numerous types of fluorescence-based assays have emerged over past two decades as reviewed (Knemeyer and Marme, 2007). The so-called TaqMan probes (Heid et al., 1996). and Molecular Beacons (Tyagi et al., 1996) are the two most prominent examples of such methods. Both of these examples utilize both a fluorophore and a non-fluorescent quencher for signal generation with the quencher responsible for the probe's low background fluorescence in the unhybridized state.

The inherent specificity of natural DNA probes is not always sufficient to meet assay goals. Several methods for improved mismatch discrimination have been suggested and include use of a secondary structure (Bonnet et al., 1999), competitive hybridization (Morrison et al., 1998), solution-phase detection of polynucleotides using interacting labels and competitive hybridization, rigid nucleic acid backbones (Tolstrup et al., 2003), and Zip DNA (Paris et al., 2010). These and some other approaches have been discussed (Demidov and Frank-Kamenetskii, 2004). It has been also shown that stabilization of DNA duplexes by minor groove binding (MGB) agents allows for much shorter probes to be used at a given assay temperature and that such probes are more sensitive to single base variations (Kutyavin et al., 2000).

In addition to high hybridization specificity, ideal fluorescence-based nucleic acid probes should possess low fluorescence background, high signal and signal-to-background ratio (S/B). The Molecular Beacons can achieve high signals and S/B through the use of self-complementary ends that bring the fluorophore and the non-fluorescent DABCYL quencher in close proximity when probe is unhybridized and are far apart when the probe is bound to its target (Tyagi S. et al., 1998). Since the introduction of DABCYL several structural types of organic non-fluorescent quenchers have been described and patented. The most extensively explored azo dye-based quenchers are Eclipse Dark Quencher (U.S. Pat. No. 6,699,975), Diarylazo quenchers (U.S. Pat. No. 6,790,945), Black Hole Quenchers (U.S. Pat. No. 7,019,129), ZEN quencher (U.S. Pat. No. 7,439,341), BlackBerry Quenchers (U.S. Pat. No. 7,879,986) and Multi-Path Quenchers (Crisalli and Kool, 2011). Other known quenchers are based on rhodamine (QSY quenchers), rhodole (U.S. Pat. No. 6,399,392), triarylmethane, fluorescein (U.S. Pat. No. 6,323,337), anthraquinone based Iowa Black quencher (U.S. Pat. No. 7,803,536) and nitro-substituted cyanine dyes (U.S. Pat. No. 7,166,715).

MGB-labeled hybridization probes called Pleiades (Lukhtanov et al., 2007, U.S. Pat. No. 7,381,818) offer the benefits of high signal and S/B without the need for the Molecular Beacon's self-complementary stem structure. The key structural features of the Pleiades probes are strategically positioned 5'-end MGB and fluorophore and 3'-end Eclipse Dark quencher. All three components work in a coordinated manner to yield a unique signal generation mechanism with low background fluorescence, high signal and S/B (Lukhtanov et al., 2007). In addition, the 5'-positioning of the MGB prevents the probe from being cleaved by Taq polymerase. The Eclipse Dark quencher (U.S. Pat. No. 6,699,975) used in these probes has been designed to optimize fluorescence quenching based on the fluorescence resonance energy transfer (FRET), which requires an overlap of the absorption spectrum of the quencher with the emission spectrum of the fluorophore. The absorption spectrum of the Eclipse Dark quencher overlaps efficiently with most common fluorophore (Fluorescein, tetramethylrhodamine, Texas Red). When used under PCR-relevant conditions (55-70° C.) the MGB-probes are 15-20 bases long. At this length hybridization of the probe to a target provides sufficient spatial separation between the fluorophore and the quencher thus eliminating most of the FRET quenching.

Despite the recognized advantages of using FRET-based Pleiades probes, there are certain situations when the FRET mechanism is detrimental to probe's performance. For example, very short MGB-probes (8-12 bases long) are ideal for low temperature (20-50° C.) applications if high hybridization specificity is required. For those probes, however, hybridization to a target does not provides sufficient spatial separation between the fluorophore and the quencher, leading to significant residual FRET quenching and consequently to a low fluorescence signal and reduced sensitivity. To fully employ the mismatch discrimination advantages of short fluorogenic MGB-probes it is, therefore, necessary to optimize the quenching mechanism with the goal of increasing fluorescence signal.

One possible solution is based on the use of so-called "non-FRET" quenchers. Contact quenching (also known as quenching by "touching" or collisional quenching) is not based on the long range (20-60 Å) FRET mechanism and requires close contact between fluorophore and quencher (U.S. Pat. No. 6,150,097). The described method works especially well in the Molecular Beacons wherein the "touching" is enhanced by the formation of the self-complementary double-stranded stem. Linear probes, however, do not demonstrate very efficient quenching. Based on dynamics of fluorophore-quencher interaction, quenching was categorized as being either dynamic or static in complex formation (Lakowicz, 2007). Three different contact quenching mechanisms were identified: intersystem crossing, electron exchange, and photoinduced electron transfer (PET). At least the last two mechanisms have been shown to be present in known nucleic acid probes. For example, the electron exchange (also known as Dexter interaction) is present (along with FRET) in linear dual labeled probes (such as TaqMan) and requires temporary orbital overlap. The photoinduced electron transfer between a fluorescent dye and a guanine base is the quenching mechanism for the so-called Smart probes (U.S. Pat. No. 7,262,007) or for probes with a guanine base in close proximity of the dye (U.S. Pat. No. 6,699,661). Examples of possible PET-mediated quenching by a methanesulfonylaminoindole (U.S. Pat. No. 7,759,470) or by nitroindole nucleosides (EP Patent No. EP1384789) are described. Lukhtanov et al. 2007 demonstrated that the $CDPI_3$-type MGB-dependent quenching invokes the PET mechanism as well. An example of the static quenching is described by Johansson et al., 2002. It is characterized by a formation of a ground state complex (hetero-dimer) between a fluorophore and a Black Hole quencher accompanied by a significant change in absorption spectra of the dyes. FIG. 1 shows a general schematic diagram for some of these quenching mechanisms in oligonucleotide probes containing MGB.

Published studies suggest that at least some of the existing quenchers already possess the required contact quenching properties and all is needed is to somehow reduce or eliminate the accompanied FRET quenching. However, problematically, all popular quenchers of common fluorophores (500-600 nm emission range) that presumably employ some degree of contact quenching also possess a significant FRET component. Moreover, those quenchers are typically designed to maximize the FRET effect.

Due to the described deficiencies, there is a need for redesign of the quenchers with the goal of weakening the FRET effect while preserving the contact quenching.

SUMMARY

The present disclosure relates to novel oligonucleotide conjugates and probes comprising fluorescence quenching nitrodiarylethene analogs. These analogs, whose absorption spectra are substantially blue-shifted relatively to emission spectra of common fluorophores (such as fluorescein), do not need to rely on spectral overlap of quencher absorbance and fluorophore's emission for their quenching abilities. As a result, the oligonucleotide probes of this invention have fluorescence characteristics that are not always achievable using existing fluorescence quenching compounds. This disclosure encompasses an approach wherein the parent diarylazo quenchers are replaced with structurally similar but spectrally more blue-shifted diarylethene analogs.

The quenchers of this disclosure are particularly useful in oligonucleotide hybridization probes having fewer than 12 bases between the fluorophore and quencher. Oligonucleotide probes of this length, when labeled with traditional quenchers, demonstrate significantly reduced fluorescence signals upon hybridization with their targets. The signal drop is due to insufficient spatial separation between the fluorophore and quencher leading to a residual FRET quenching. The new quenchers, which substantially devoid of FRET quenching properties, allow to avoid this disadvantage.

A particular class of probes that is suitable for use in conjunction with the fluorescence quenching compounds comprises a fluorescent label (Fl) and a minor groove binder (MGB). Such probes are short, due to the duplex stabilizing effect of the MGB, and are optimal for distinguishing closely related nucleic acid targets. Importantly, these probes containing the present fluorescence quenching compounds demonstrate low background fluorescence and high hybridization signals, the latter being significantly higher than those achieved using the older FRET-based quenchers. Both the background fluorescence and signal are essential parameters for improving assay sensitivity.

Another type of probe that may be used with the current fluorescence quenching compounds are Molecular Beacons. Short Molecular Beacons demonstrate improved fluorescence characteristics due to the presence of new fluorescence quenchers.

In one embodiment, the probes are useful in all hybridization-based assays requiring short probes. One preferred embodiment is the use in digital PCR, such as that described in U.S. Patent Application Publication No. 2014/0335515.

The present fluorescence quenching compounds are also useful in nucleic acid probes that utilize other duplex stabilizing technologies such as locked nucleic acids (LNA), peptide nucleic acid (PNA), ZNA, and the like.

The present disclosure also provides reagents for nucleic acid labeling. These reagents enable direct 3', 5' and internal quencher incorporation during oligonucleotide synthesis. Examples of these reagents include phosphoramidites, and solid supports for oligonucleotide synthesis. The reagents are compatible with oligonucleotide synthesis and deprotection conditions and are, therefore, suitable for efficient probe manufacturing. Alternatively, certain reagents, including activated esters, can be used for post-synthetic modification of oligonucleotides and artificial oligonucleotide analogs.

In addition, the present disclosure relates to assays employing the novel oligonucleotide-quencher conjugates and assay kits containing them.

BRIEF DESCRIPTION OF THE DRAWINGS

FIG. 7A shows duplex fluorescence (signal), single strand fluorescence (background) and signal-to-background ratio (S/B) of 11-mer Pleaides probes labeled with FAM and selected quenchers in accordance with preferred embodiments disclosed herein.

DETAILED DESCRIPTION

Definitions

Figure 1:
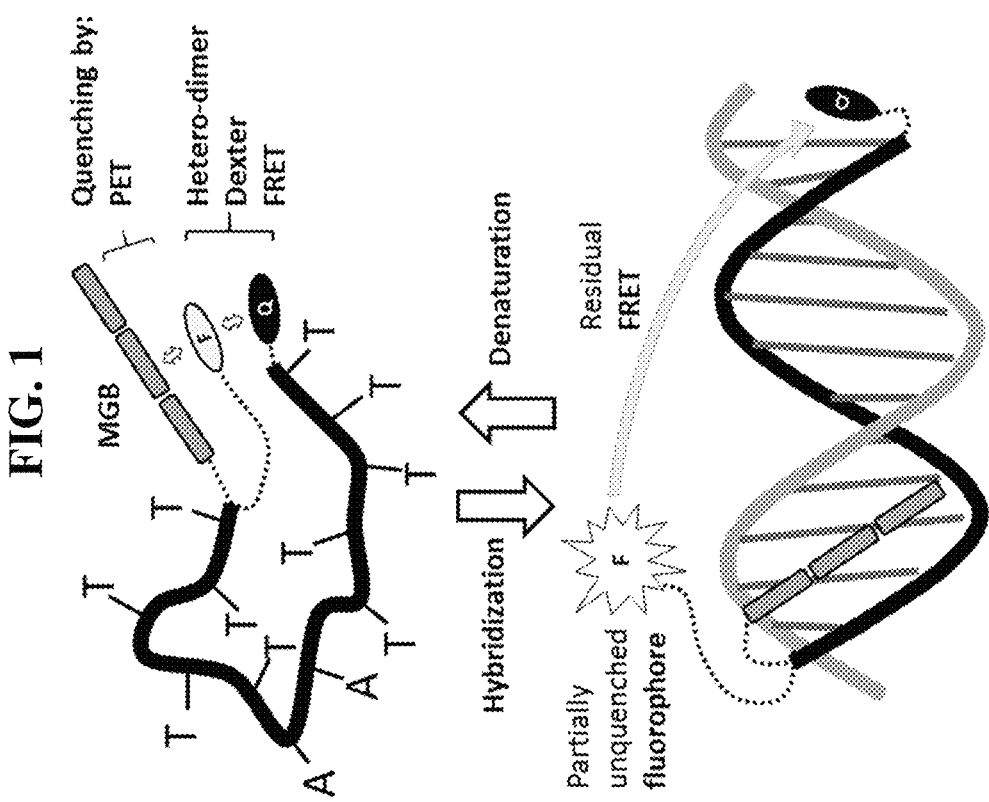
FIG. 1 shows a general schematic diagram of a proposed mechanism for quenching and hybridization-triggered fluorescence in Pleaides probes.

The abbreviations MGB, Fl, Q, CPG and ODN refer to "minor groove binder", "fluorescent label" or "fluorophore", "quencher", "controlled pore glass" (as an example of a solid support) and "oligonucleotide" moieties or molecules, respectively, and in a manner which is apparent from context.

The term "minor groove binder" refers to a moiety that is capable of forming a complex (typically non-covalent) with the minor groove of DNA. The minor groove binders of the invention are oligonucleotide conjugates (or "probes") as described in U.S. Pat. Nos. 5,801,155 and 6,312,894, both hereby incorporated by reference. These conjugates form hyper-stabilized duplexes with complementary DNA. In particular, sequence specificity of short minor groove binder probes is excellent for high temperature applications such as PCR. The probes/conjugates of the present disclosure can also have a covalently attached minor groove binder. A variety of suitable minor groove binders have been described in the literature (U.S. Pat. No. 5,801,155; Wemmer, D. E., and Dervan P. B., 1997; Walker et al., *Biopolymers*, 44:323-334, 1997; Zimmer, C & Wahnert, U., 1986; and Reddy, et al., *Pharmacol. Therap.*, 84:1-111, 1999).

Suitable methods for attaching minor groove binders (as well as reporter groups such as fluorophores and quenchers) through linkers to oligonucleotides have also been described (U.S. Pat. Nos. RE 38,416; 5,512,677; 5,419,966; 5,696, 251; 5,585,481; 5,942,610 and 5,736,626).

The term "fluorescent label or fluorophore" refers to an organic moiety that is capable of absorbing and re-emitting light. Typically, fluorophores absorb light of certain wavelength range (excitation spectrum) and re-emitting it at a longer wavelength range (emission spectrum) with respective excitation and emission maxima. The fluorophores of the invention have excitation and emission maxima between 400 and 900 nm. Examples of these dye classes can be found in Haugland, et al., HANDBOOK OF FLUORESCENT PROBES AND RESEARCH CHEMICALS, SIXTH ED., Molecular Probes, Eugene, Oreg. 1996; Krasoviskii and Bolotin, ORGANIC LUMINESCENT MATERIALS, VCH Publishers, N.Y., 1988; Zolliger, COLOR CHEMISTRY, 2nd Edition, VCH Publishers, N.Y., 1991. Still other dyes are provided via online sites such as zeiss.com. Phosphonate dyes are disclosed in co-owned U.S. Pat. Nos. 7,671,218, 7,767,834 and 8,163,910.

The term "quencher" refers to an organic moiety that is capable of reducing the efficiency of light re-mission by a fluorophore.

The term "oligonucleotide" refers to a fragment of natural or artificial nucleic acid or combination of thereof. Examples of artificial nucleic acids include analogs with modified sugar-phosphate backbone such as 2-OMe nucleic acid, peptide nucleic acid (PNA), locked nucleic acid (LNA), threose nucleic acid (TNA), glycol nucleic acid (GNA). Artificial nucleic acid may also comprise modified nucleobases.

The term "modified nucleobases or modified bases" refers to those bases that differ from the naturally-occurring bases (adenine, cytosine, guanine, thymine, and uracil) by addition or deletion of one or more functional groups, differences in the heterocyclic ring structure (i.e., substitution of carbon for a heteroatom, or vice versa), and/or attachment of one or more linker arm structures to the base. Modified bases include naturally-occurring and synthetic modifications and analogues of the major bases such as, for example, hypoxanthine, 2-aminoadenine, 2-thiouracil, 2-thiothymine, inosine, 5-$N^4$-ethenocytosine, 4-aminopyrrazolo[3,4-d]pyrimidine and 6-amino-4-hydroxy-[3,4-d]pyrimidine. Any modified nucleotide or nucleotide analogue compatible with hybridization of probe with a nucleic acid conjugate to a target sequence is useful, even if the modified nucleotide or nucleotide analogue itself does not participate in base-pairing, or has altered base-pairing properties compared to naturally-occurring nucleotides. Examples of modified bases are disclosed in U.S. Pat. Nos. 7,045,610; 5,824,796; 6,127,121; 5,912,340; and PCT Publications WO 01/38584 and WO 01/64958, each of which is hereby incorporated herein by reference in its entirety. Preferred modified bases include 5-hydroxybutynyl uridine for uridine; 4-(4,6-Diamino-1H-pyrazolo[3,4-d]pyrimidin-3-yl)-but-3-yn-1-ol, 4-amino-1H-pyrazolo[3,4-d]pyrimidine, and 4-amino-1H-pyrazolo[3,4-d]pyrimidine for adenine; 5-(4-Hydroxy-but-1-ynyl)-1H-pyrimidine-2,4-dione for thymine; and 6-amino-1H-pyrazolo[3,4-d]pyrimidin-4(5H)-one for guanine. Particularly preferred modified bases are "Super A®: 4-(4,6-Diamino-1H-pyrazolo[3,4-d]pyrimidin-3-yl)-but-3-yn-1-ol," "Super G": 4-hydroxy-6-amino pyrazolopyrimidine" (elitechgroup.com) and "Super T": 5-(4-hydroxy-but-1-ynyl)-1H-pyrimidine-2,4-dione". "Super-D™: 3-Alkynyl pyrazolopyrimidine" analogues as universal bases are disclosed in U.S. Patent Application Publication No. 2012/0244535, incorporated by reference.

The term "linker" refers to a moiety that is used to assemble various portions of the molecule or to covalently attach the molecule (or portions thereof) to a solid support. Typically, a linker or linking group has functional groups that are used to interact with and form covalent bonds with functional groups in the ligands or components (e.g., fluorophores, oligonucleotides, minor groove binders, or quenchers) of the oligonucleotide probes described and used herein. Additionally, a linker can include linear or acyclic portions, cyclic portions, aromatic rings or combinations thereof (U.S. Pat. Nos. 5,419,966; 5,696,251; 5,585,481; 5,942,610 and 5,736,626).

The terms "functional" and "reactive" groups in this invention are used interchangeably and refer to chemical groups and moieties that are suitable for the formation of a chemical bond. They are exemplified but not limited to amines, oxyamines, hydrazines, hydrazides, semi-carbazides, semi-thiocarbazides, hydroxyl-substituted compounds, sulfur compounds (such as thiols, dithiols, thiocarbonyl compounds, phosphorothiates), carboxylates, phosphates, phosphonates, aromatic nitrogens (such as in pyridine), amide nitrogens, azides, electron-rich aromatics, etc.), acids (in the presence of activating agents), esters, imidoesters, anhydrides, acid chlorides, acyl azides, lactones, azlactones, isocyanates, isothiocyanates, o-acylisoureas, acid amides (such as acyl imidazolides or phosphoramidites), carbonyl compounds, halogenated hydrocarbons, halogenated aromatics (such as triazine chloride, electron-deficient fluoroaromatics), unsaturated hydrocarbons, aromatic diazonium salts, epoxides, aziridines. Other types of functional or reactive groups include photo-reactive (azides, benzophenones, diazirines, etc.), metal chelating groups (aminodiacetic acid), substrates for metal-catalyzed coupling, ligands for molecular recognition (such as biotin), antigens and haptens. Functional and reactive groups of this invention may also be used in conjunction with bi-functional or poly-functional cross-linking reagents (such as bis-amines, bis-aldehydes, maleimido-NHS esters, etc). Other examples of reactive groups and cross-linking reaction can be found in literature (Hermanson, Bioconjugate Techniques, Elsevier, 1996).

"Protecting group" or "protected form thereof" refers to a grouping of atoms that, when attached to a reactive group in a molecule, masks, reduces or prevents that reactivity. Examples of protecting groups can be found in T. W. Greene and P. G. Wuts, 2007 and Harrison and Harrison et al 1971 to 1996. Representative amino protecting groups include formyl, acetyl, trifluoroacetyl, benzyl, benzyloxycarbonyl (CBZ), tert-butoxycarbonyl (Boc), trimethyl silyl (TMS), 2-trimethylsilylethanesulfonyl (SES), trityl and substituted trityl groups, allyloxycarbonyl, 9-fluorenylmethyloxycarbonyl (FMOC), nitro-veratryloxycarbonyl (NVOC) and the like. Representative hydroxy protecting groups include those where the hydroxy group is either acylated or alkylated such as benzyl and trityl ethers as well as alkyl ethers, tetrahydropyranyl ethers, trialkylsilyl ethers and allyl ethers.

The term "solid support" refers to any support that is compatible with oligonucleotide synthesis including, for example, glass, controlled pore glass, polymeric materials, polystyrene, beads, coated glass and the like.

The term "alkyl" refers to a linear, branched, or cyclic saturated monovalent hydrocarbon substituent or a combination of cyclic and linear or branched saturated monovalent substituents having the number of carbon atoms indexed in the prefix. For example, $(C_1-C_8)$alkyl is meant to include methyl, ethyl, n-propyl, 2-propyl, tert-butyl, pentyl, cyclopentyl, cyclopropylmethyl and the like. For each of the definitions herein (e.g., alkyl, alkenyl, alkoxy, aralkyloxy), when a prefix is not included to indicate the number of chain carbon atoms in an alkyl portions, the substituent thereof will have eight or fewer main chain carbon atoms.

The term "alkylene" refers to a linear saturated divalent hydrocarbon substituent or a branched saturated divalent hydrocarbon substituent having the number of carbon atoms indicated in the prefix. For example, $(C_1-C_6)$alkylene is meant to include methylene, ethylene, propylene, 2-methylpropylene, pentylene, and the like.

The term "aryl" means a monovalent or bivalent (e.g., arylene) monocyclic, bicyclic aromatic or tricyclic hydrocarbon substituent of 5, or in some cases fewer than 5, to 14 ring atoms which is unsubstituted or substituted. If substituted the substituents are selected from those groups provided below. The term "heteroaryl" refers to aryl wherein one or more heteroatoms or heteroatom functional groups have replaced a ring carbon, while retaining aromatic properties, e.g., pyridyl, quinolinyl, quinazolinyl, thienyl, and the like. More specifically the terms aryl and heteroaryl include, but are not limited to, phenyl, 1-naphthyl, 2-naphthyl, thienyl and benzothiazolyl, and the substituted forms thereof.

Substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O) NR'R", —NR"C(O)R', —NR"C(O)$_2$R', —NR'—C(O), NR"R''', —NH—C(NH2) =NH, —NR'C(NH2)=NH, —NH—C(NH2)=NR', —S(O) R', —S(O)$_2$R', —S(O)$_2$NR'R", —N$_3$, —CH(Ph)$_2$, perfluoro $(C_1-C_4)$alkoxy, and perfluoro$(C_1-C_4)$alkyl, in a number ranging from zero to the total number of open valences on the aromatic ring system; and where R', R" and R''' are independently selected from hydrogen, $(C_1-C_8)$alkyl and heteroalkyl, unsubstituted aryl and heteroaryl, (unsubstituted aryl)-$(C_1-C_4)$alkyl, and (unsubstituted aryl)oxy-$(C_1-C_4)$alkyl. Preferred substituents are —OH, Halogen, OR', —OC(O)R', —NR'R", —SR', —R', —CN and —NO$_2$— where R' and R" are independently —H— or —$(C_1-C_4)$.

The prefix "halo" and the term "halogen," when used to describe a substituent, refer to —F, —Cl, —Br and —I. Certain compounds or oligonucleotides of the present disclosure may exist in a salt form.

Such salts include base addition salts such as sodium, potassium, calcium, ammonium, organic amino, or magnesium salt, or a similar salt. When the compounds or modified oligonucleotides of the present disclosure contain relatively basic functionalities, acid addition salts can be obtained by contacting the neutral form of such compounds with a sufficient amount of the desired acid, either neat or in a suitable inert solvent. Examples of acceptable acid addition salts include those derived from inorganic acids like hydrochloric, hydrobromic, nitric, carbonic, monohydrogencarbonic, phosphoric, monohydrogenphosphoric, dihydrogenphosphoric, sulfuric, monohydrogensulfuric, hydriodic, or phosphorous acids and the like, as well as the salts derived from organic acids like acetic, propionic, isobutyric, maleic, malonic, lactic, benzoic, succinic, suberic, fumaric, mandelic, phthalic, benzenesulfonic, p-tolylsulfonic, citric, tartaric, methanesulfonic, and the like. Also included are salts of amino acids such as arginate and the like, and salts of organic acids like glucuronic or galactunoric acids and the like (Berge, S. M., et al. 1977). Certain specific compounds described herein contain both basic and acidic functionalities that allow the compounds to be converted into either base or acid addition salts. The neutral forms of the compounds may be regenerated by contacting the salt with a base or acid and isolating the parent compound in the conventional manner. The parent form of the compound differs from the various salt forms in certain physical properties, such as solubility in polar solvents, but otherwise the salts are equivalent to the parent form of the compound for the purposes of the present disclosure.

Certain compounds of the present disclosure can exist in unsolvated forms as well as solvated forms, including hydrated forms. In general, the solvated forms are equivalent to unsolvated forms and are intended to be encompassed within the scope of the present disclosure. Certain compounds of the present disclosure may exist in multiple crystalline or amorphous forms. In general, all physical forms are equivalent for the uses contemplated by the present disclosure and are intended to be within the scope of the present disclosure.

Certain compounds of the present disclosure possess asymmetric carbon atoms (optical centers) or double bonds; the racemates, diastereomers, geometric isomers and individual isomers are all intended to be encompassed within the scope of the present disclosure. The methods for the determination of stereochemistry and the separation of isomers are well-known in the art (March, J., 1992).

The compounds of the present disclosure may also contain unnatural proportions of atomic isotopes at one or more of the atoms that constitute such compounds. For example, the compounds may be radiolabeled with radioactive isotopes, such as for example tritium ($^3H$), iodine-125 ($^{125}I$) or carbon-14 ($^{14}C$). All isotopic variations of the compounds of the present disclosure, whether radioactive or not (e.g, $^2H$), are intended to be encompassed within the scope of the present disclosure.

"Optional" or "optionally" in the above definitions means that the subsequently described event or circumstance may but need not occur, and that the description includes instances where the event or circumstance occurs and instances in which it does not. For example, "aryl optionally mono- or di-substituted with an alkyl group" means that the alkyl group may, but need not, be present, and the description includes situations where the aryl group is mono- or bis-substituted with an alkyl group and situations where the aryl group is not substituted with the alkyl group.

The term "digital PCR" refers to an approach to nucleic acid detection and quantification, which is a method of absolute quantification since it directly counts the number of target molecules rather than relying on reference standards or endogenous controls (Sedlak and Jerome 2013).

The term "arrays" refers to hybridization of the probes of the invention to an immobilized oligonucleotide (U.S. Pat. No. 6,045,996). In some arrays, the probes described herein are immobilized to a solid support (U.S. Pat. No. 6,821,727).

The practice of the present disclosure will employ, unless otherwise indicated, conventional techniques in organic chemistry, biochemistry, oligonucleotide synthesis and modification, bioconjugate chemistry, nucleic acid hybridization, molecular biology, microbiology, genetics, recombinant DNA, and related fields as are within the skill of the art. These techniques are fully explained in the literature. See, for example, Maniatis, Fritsch & Sambrook 1982; Sambrook, Fritsch & Maniatis, (1989); Ausubel, et al., 1987, 1988, 1989, 1990, 1991, 1992, 1993, 1994, 1995, 1996; Gait (ed.), 1984; Eckstein (ed.), 1991.

In one aspect the present disclosure provides quencher reagents for oligonucleotide labeling having the Formula I

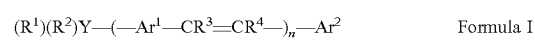

Formula I wherein $Ar^1$ and $Ar^2$ each independently represent a substituted or unsubstituted aryl or heteroaryl group and at least one of $Ar^1$ or $Ar^2$ is substituted with a nitro ($NO_2$) group and further additional substituents for the aryl and heteroaryl groups are varied and are selected from: -halogen, —OR', —OC(O)R', —NR'R", —SR', —R', —CN, —$NO_2$, —$CO_2R'$, —CONR'R", —C(O)R', —OC(O) NR'R", —NR"C(O)R', —NR"C(O)$_2$R', —NR'—C(O), NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —$N_3$, —CH(Ph)$_2$, perfluoro($C_1$-$C_4$)alkoxy, and perfluoro($C_1$-$C_4$) alkyl, in a number ranging from zero to the total number of open valences on the aromatic ring system; and where R', R" and R'" are independently selected from hydrogen, ($C_1$-$C_8$) alkyl and heteroalkyl, unsubstituted aryl and heteroaryl, (unsubstituted aryl)-($C_1$-$C_4$)alkyl, and (unsubstituted aryl) oxy-($C_1$-$C_4$)alkyl.

Preferred substituents are —OH, Halogen, OR', —OC(O)R', —NR'R", —SR', —R', —CN and —$NO_2$— where R' and R" are independently —H— or —($C_1$-$C_4$).

In addition, $R^3$ and $R^4$ are independently H or ($C_1$-$C_8$) alkyl; n is from 1 to 3 and when n is 2 or 3 the multiple $Ar^2$ moieties are the same or different;

Y is a linking group connecting $Ar^1$ with $R^1$ and $R^2$ and having from 0 to 100 main chain atoms selected from C, N, O, S, P and Si and can be acyclic, cyclic or aromatic or combinations thereof;

$R^1$ is a protected or unprotected functional group (e.g., a hydroxyl, that optionally is protected with a suitable protecting group as are known to those of skill in the art, or carboxylic acid or pentafluorophenyl (PFP) ester, any phosphorus coupling moiety used in oligonucleotide synthesis, for example, a phosphoramidite of the formula O—P (N(iPr)$_2$)(OCH$_2$CH$_2$CN)), or alternatively, a linking group attached to a solid support of the formula O—C(=O)Z-solid support wherein Z is 1 to 30 main chain atoms in length wherein the main chain atoms are selected from C, N, O, P, and S, and Z can include acyclic, cyclic or aromatic groups or combinations thereof; and $R^2$ is H, ($C_1$-$C_{12}$)alkyl, aryl, heteroaryl, or a protected or unprotected functional group.

For those embodiments in which Y has 0 main chain atoms, the $R^2$ group is absent and the $R^1$ group is directly connected to the $Ar^1$ moiety. In one particular embodiment of this aspect the reagents of Formula I contain at least two nitro groups.

In additional aspects the present disclosure provides quencher reagents for oligonucleotide labeling having the formula:

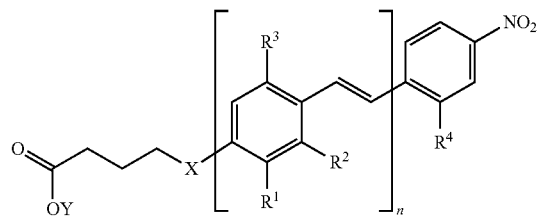

wherein Y is Et, H, or PFP, $R^1$ is H or OMe, $R^2$ is H, or $R^1$ and $R^2$ are each —CH=CH— and link together to form an aromatic group, $R^3$ is H or OMe, $R^4$ is H, $NO_2$, or Cl, n is 1 or 2, and X is N(Me), N(Et), or O.

The descriptions provided herein may include abbreviations for methyl (Me) and ethyl (Et) groups.

In further aspects the present disclosure provides quencher reagents for oligonucleotide labeling having the formula:

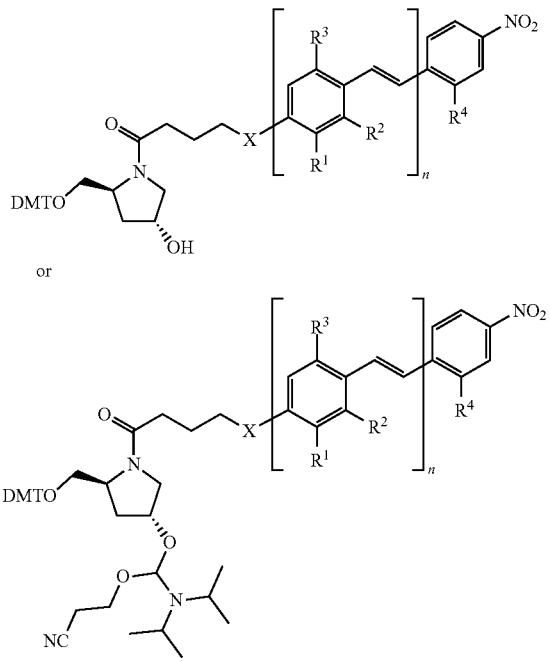

wherein DMT is dimethoxytrityl, $R^1$ is H or OMe, $R^2$ is H, or $R^1$ and $R^2$ are each —CH=CH— and link together to form an aromatic group, $R^3$ is H or OMe, $R^4$ is H, $NO_2$, or Cl, n is 1 or 2, and X is N(Me), N(Et), or O.

Figure 2:
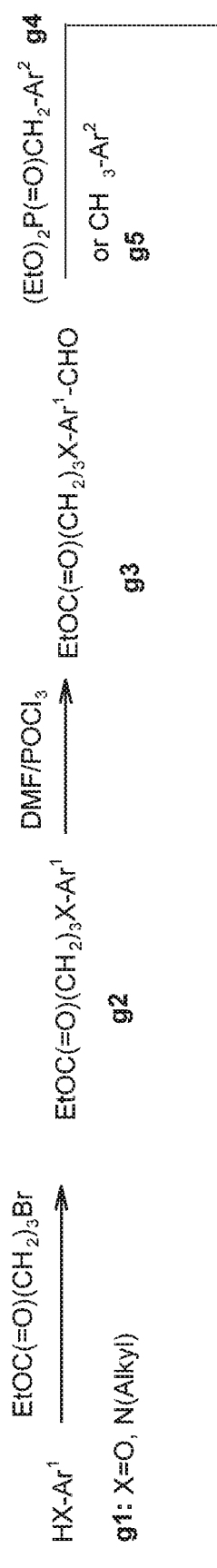
FIG. 2 shows Scheme 1, a general reaction scheme for synthesis of activated esters of compounds in accordance with preferred embodiments of this disclosure.
Figure 2:

Activated esters of the compounds of this disclosure are such for example when $R^1$ or $R^2$ in Formula I is an activated carboxyl (NHS, PFP esters and alike). They can be synthesized by the method illustrated in generic reaction Scheme 1, shown in FIG. 2. The starting hydroxy- or N-alkylamino-substituted aromatics g1 are reacted with ethyl 4-bromobutyrate to introduce a prerequisite linker suitable for further conversion to an active ester. The linker-modified aromatics g2 are then formylated using, for instance, the Vilsmeier-Haack reaction. The aryl aldehydes g3 thus obtained are then converted into diarylethenes by the Horner-Wadsworth-Emmons reaction with diethyl (arylmethyl)phosphonates (g4) (accessible through the Arbuzov reaction) in the presence of strong base such as sodium ethylate. Alternatively, highly reactive methyl-substituted aromatics (g5) (such as dinitrotoluenes) can be directly condensed with aryl aldehydes in the presence of a base. The obtained diarylethenes g6 are predominantly trans-isomers in regard to orientation of the aryl groups around the double bond. Other methods of conversion of arylcarbonyl compounds into diarylethenes are known and reviewed (Edmonds et al. (2004)). The ester intermediates g6 are saponified yielding carboxylates g7, which are then converted to pentafluorophenyl (PFP) esters g8 using pentafluorophenyl trifluoroacetate (PFP-TFA). Alternatively, using reagents and procedures known in the art, a variety of different activated esters can be prepared starting from carboxylates g7.

Figure 3:
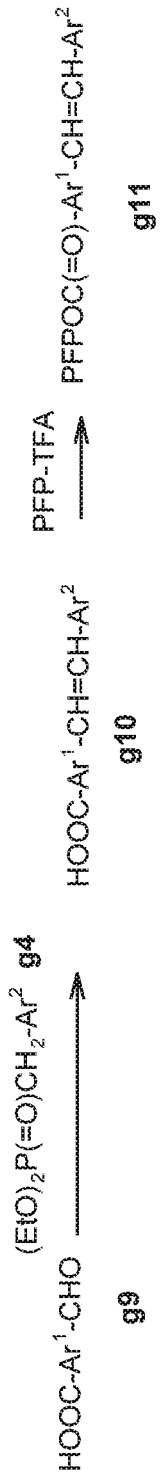
FIG. 3 shows Scheme 2, a general reaction scheme for synthesizing carboxy-substituted diarylethenes in accordance with preferred embodiments of this disclosure.

Aromatic formyl carboxylic acids and their esters, which are either commercially available or prepared by methods known in the art, can also be used to synthesize carboxy-substituted diarylethenes as shown in generic Scheme 2 (FIG. 3). The diarylethene carboxylic acids g10 obtained by the aforementioned olifination methods are converted to activated esters of choice such as PFP esters g1.

Figure 4:
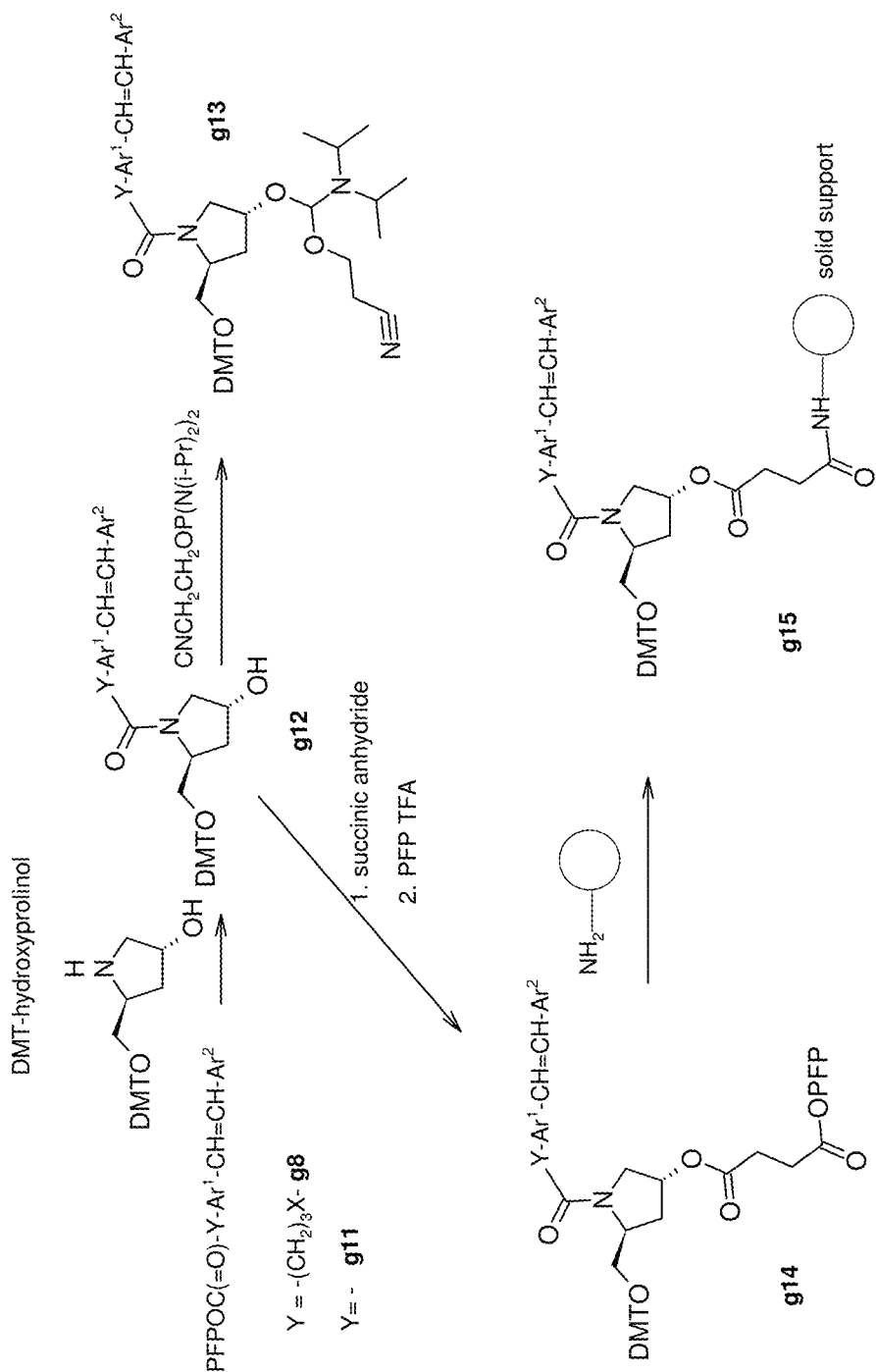
FIG. 4 shows Scheme 3, a general reaction scheme for the preparation of phosphoramidites and oligonucleotide solid synthesis supports in accordance with preferred embodiments of this disclosure.

The activated esters are used directly for the preparation of oligonucleotide-quencher conjugates by reacting, for example, with amine-modified oligonucleotides or, alternatively, with linker moieties. Those linker moieties may be mono- or poly functional and contain various functional groups such as maleimide, biotin, azide, alkyne, amine, hydroxyl, DMT-protected hydroxyl, etc. One particular type of such linker is a hydroxyprolinol analog and is suitable for the preparation of phosphoramidites and oligonucleotide solid synthesis supports as illustrated in Scheme 3 (FIG. 4).

Hydroxyprolinol is a trifunctional reagent that has an amino, a primary and a secondary hydroxyl group. This linker as well as examples of other trifunctional reagents having an amino, primary and a secondary hydroxyl group, are described in U.S. Pat. No. 5,512,667. The primary hydroxyl group in this example is protected with a dimethoxytrityl group whereas the secondary hydroxyl and amino groups are available for further modifications. As illustrated in reaction Scheme 3 (FIG. 4) the activated esters described above can be reacted with the DMT-protected hydroxyprolinol to yield intermediates g12. The free secondary hydroxyl group of intermediates g12 is then reacted with 2-cyanoethyl N,N,N',N'-tetraisopropyl-phosphordiamidite to give the dimethoxytrityl-protected phosphoramidites g13. Alternatively, the intermediates g12 are reacted with succinic anhydride followed by PFP-TFA to yield PFP succinates g14 which in turn reacted with an oligonucleotide synthesis support such as long chain alkylamine CPG or aminomethyl polystyrene to afford solid supports g15. Linkers other than succinate can also be used to link the secondary hydroxyl of hydroxyprolinol to the solid support.

The phosphoramidites g13 and solid supports g15 are versatile reagents that allow on line (automated) incorporation of compounds of this disclosure onto oligonucleotides in various positions of oligonucleotide structure. For example, the phosphoramidites g13 can be used to label the 5'-end as well as placed internally between two nucleotides of an oligonucleotide. The solid supports g15 are used the best for the 3'-end labeling, however, the use of commercially available 5'-nucleoside phosphoramidites will also yield 5'-end labeled oligonucleotides.

Other phosphoramidites described herein have a single hydroxyl group as a one-step precursor to the phosphoramidite and are prepared, for instance, by alkylation of hydroxyl, thiol or amine-substituted aromatic aldehydes or ketones (commercially available or prepared by known methods) with halo or tosyl-alkyl alcohols followed by the olefination reactions described above in Scheme 1 and 2 (FIGS. 2 and 3) and phosphoramidite formation. Those mono-functionalized phosphoramidites are suitable for end-labeling only. Alternatively, the hydroxyl of the one-step precursors can be converted into a variety of reactive groups other than activated esters or phosphoramidites. Examples of such groups include but are not limited to nitrophenyl-carbonate, iodoacetate, tosylate, iodide.

One important aspect of this disclosure is that the phosphoramidites and solid support described herein are generally compatible with standard oligonucleotide synthesis and deprotection conditions.

Another aspect of this disclosure is an oligonucleotide conjugate comprising a fluorescence quenching compound. In one particular embodiment such oligonucleotide conjugate is described by the Formula II

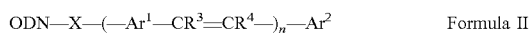
Formula II wherein $Ar^1$ and $Ar^2$ each independently represent a substituted or unsubstituted aryl or heteroaryl group;
at least one of $Ar^1$ or $Ar^2$ contains a nitro group and further additional substituents for the aryl and heteroaryl groups are varied and are selected from: -halogen, —OR', —OC(O)R', —NR'R", —SR', —R', —CN, —NO$_2$, —CO$_2$R', —CONR'R", —C(O)R', —OC(O) NR'R", —NR"C(O)R', —NR"C(O)$_2$R', —NR'—C(O), NR"R'", —NH—C(NH$_2$)=NH, —NR'C(NH$_2$)=NH, —NH—C(NH$_2$)=NR', —S(O)R', —S(O)$_2$R', —S(O)$_2$NR'R", —N$_3$, —CH(Ph)$_2$, perfluoro(C$_1$-C$_4$)alkoxy, and perfluoro(C$_1$-C$_4$)alkyl, in a number ranging from zero to the total number of open valences on the aromatic ring system, where R', R" and R'" are independently selected from hydrogen, (C$_1$-C$_8$)alkyl and heteroalkyl, unsubstituted aryl and heteroaryl, (unsubstituted aryl)-(C$_1$-C$_4$)alkyl, and (unsubstituted aryl)oxy-(C$_1$-C$_4$)alkyl.
Preferred substituents are —OH, Halogen, OR', —OC(O)R', —NR'R", —SR', —R', —CN and —NO$_2$— where R' and R" are independently —H— or —(C$_1$-C$_4$).
Further, $R^3$ and $R^4$ are independently H or (C$_1$-C$_8$) alkyl;
n is from 1 to 3 and when n is 2 or 3 the multiple $Ar^2$ moieties are the same or different;
ODN is an oligonucleotide; and
X is a linking group having from 1 to 100 backbone atoms selected from C, N, O, S, Si and P, said linking group being cyclic, acyclic, aromatic or combination thereof, and connecting the $Ar^1$ moiety with any of the 3' end, 5' end, an internucleotide phosphate (or modified phosphate), a sugar (modified sugar) moiety or a nucleobase (modified nucleobase).

The linker X is formed from the $(R^1)(R^2)Y$ group of compounds of Formula I when they are reacted (or cross-linked) with oligonucleotides (or functionalized oligonucleotides) or used in oligonucleotide synthesis.

In another embodiment, an oligonucleotide conjugate comprises more than one fluorescence quenching compound described herein, which may be the same or different and attached next to each other or distantly. Such oligonucleotide conjugates can be prepared, for instance, by an on-line oligonucleotide synthesis using the aforementioned phosphoramidites g13 and solid supports g15. The phosphoramidites g13 are particularly suitable for this application since they have a cleavable DMT group and therefore can be incorporated at any step of oligonucleotide synthesis. Those conjugates can also be prepared by a combination of on-line and post-synthetic conjugation steps, for example, by first synthesizing an amine-containing oligonucleotide on-line and then reacting it off-line (in solution) with an activated ester reagent such as g8 or g11.

In another embodiment, an oligonucleotide conjugate comprises a fluorescence quenching compound and has the formula:

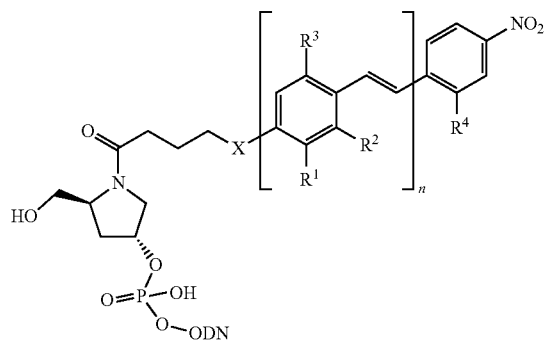

wherein $R^1$ is H or OMe, $R^2$ is H, or $R^1$ and $R^2$ are each —CH=CH— and link together to form an aromatic group, $R^3$ is H or OMe, $R^4$ is H, NO$_2$, or Cl, X is N(Me), N(Et), or O, n is 1 or 2, and ODN is an oligonucleotide.

In another embodiment, an oligonucleotide conjugate in addition to the fluorescence quenching compound described herein comprises a fluorophore. One preferred embodiment of the oligonucleotide conjugate of Formula II is described by the Formula III:

Formula III wherein Fl is a fluorophore;
ODN is an oligonucleotide; and
Q is a quenching compound of structure —X—(—Ar$^1$—CR$^3$=CR$^4$—)$_n$—Ar$^2$.

The configuration of Formula III emphasizes that the fluorophore is covalently attached to one end and the quencher to another end of an oligonucleotide.

Figure 10A:
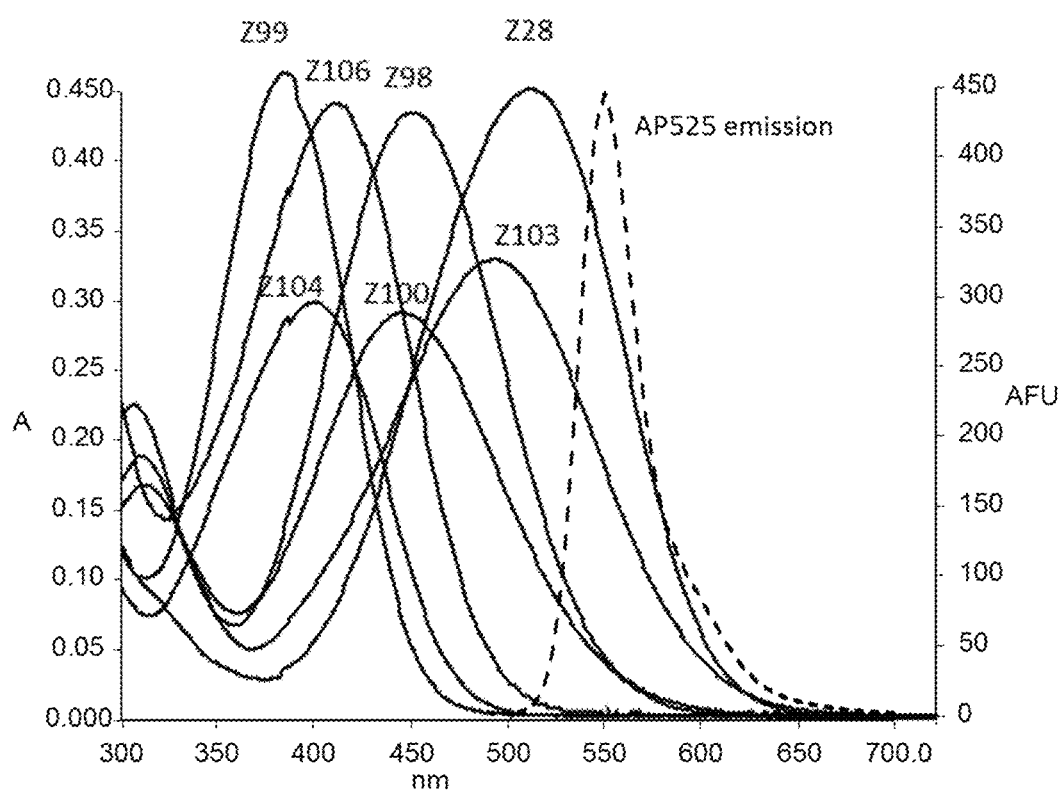
FIG. 10A shows absorption spectra of different quenchers in accordance with preferred embodiments disclosed herein and fluorescence spectrum of the AP525 dye.
Figure 10B:
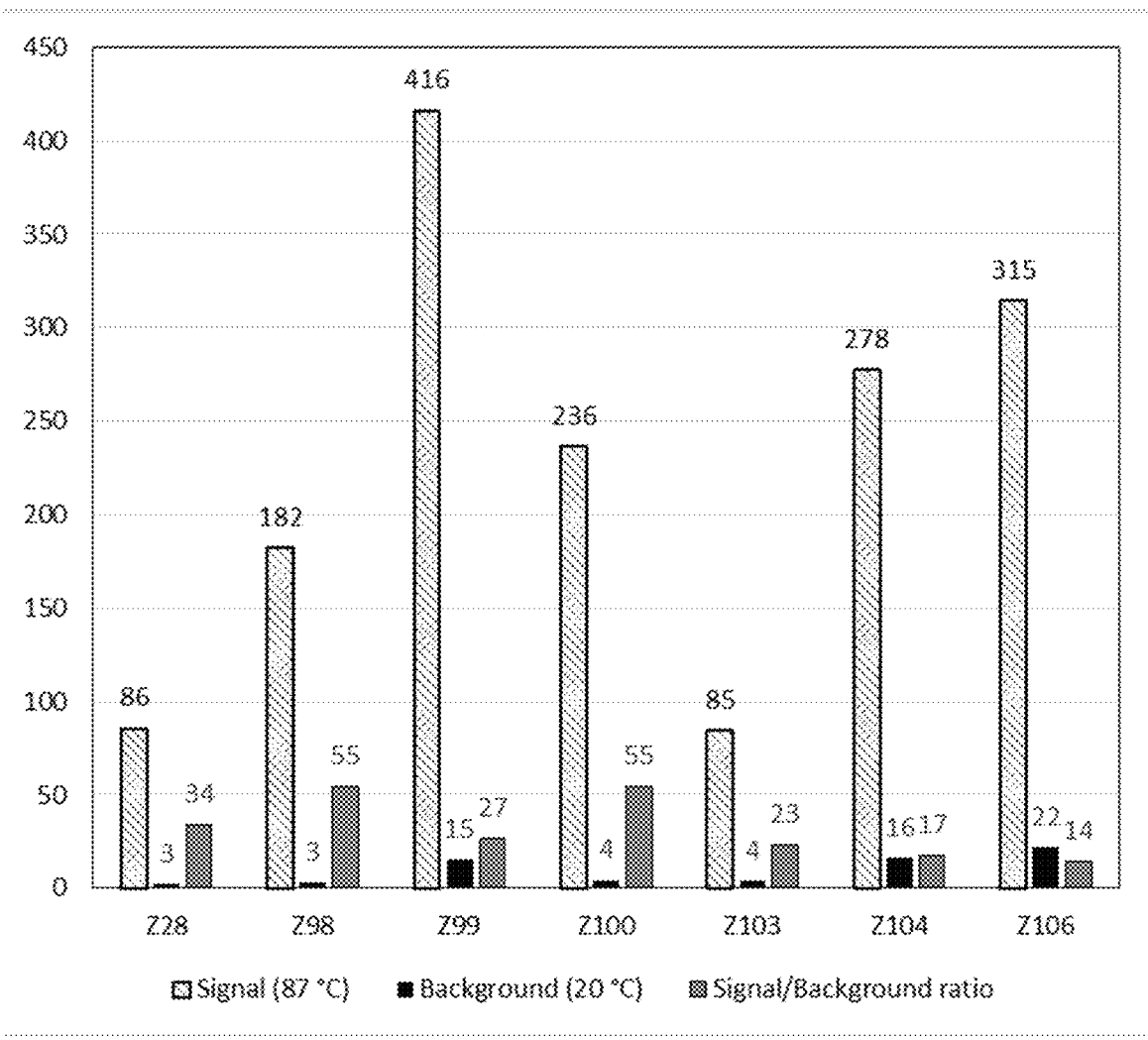
FIG. 10B shows fluorescence of open (signal) and closed (background) forms and signal-to-background ratio (S/B) of an exemplary Molecular Beacon probe, with fluorescence signal and background measured at 90 and 20° C., respectively.
Figure 11A:
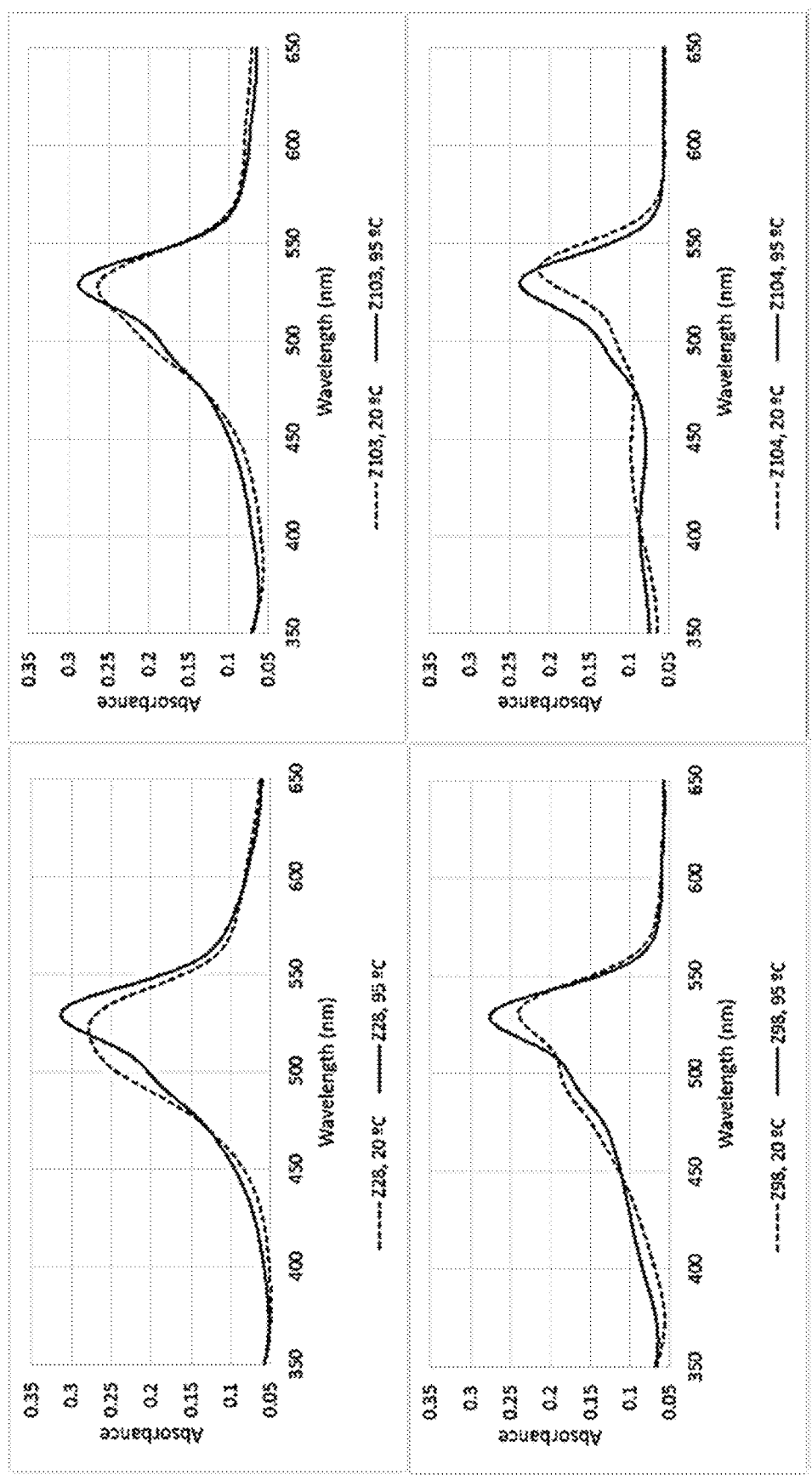
FIG. 11A shows absorption spectra of open (95° C.) and closed (20° C.) forms of an exemplary Molecular Beacon probe labeled with Eclipse (Z28) and various nitrodiarylethene quenchers.
Figure 11B:
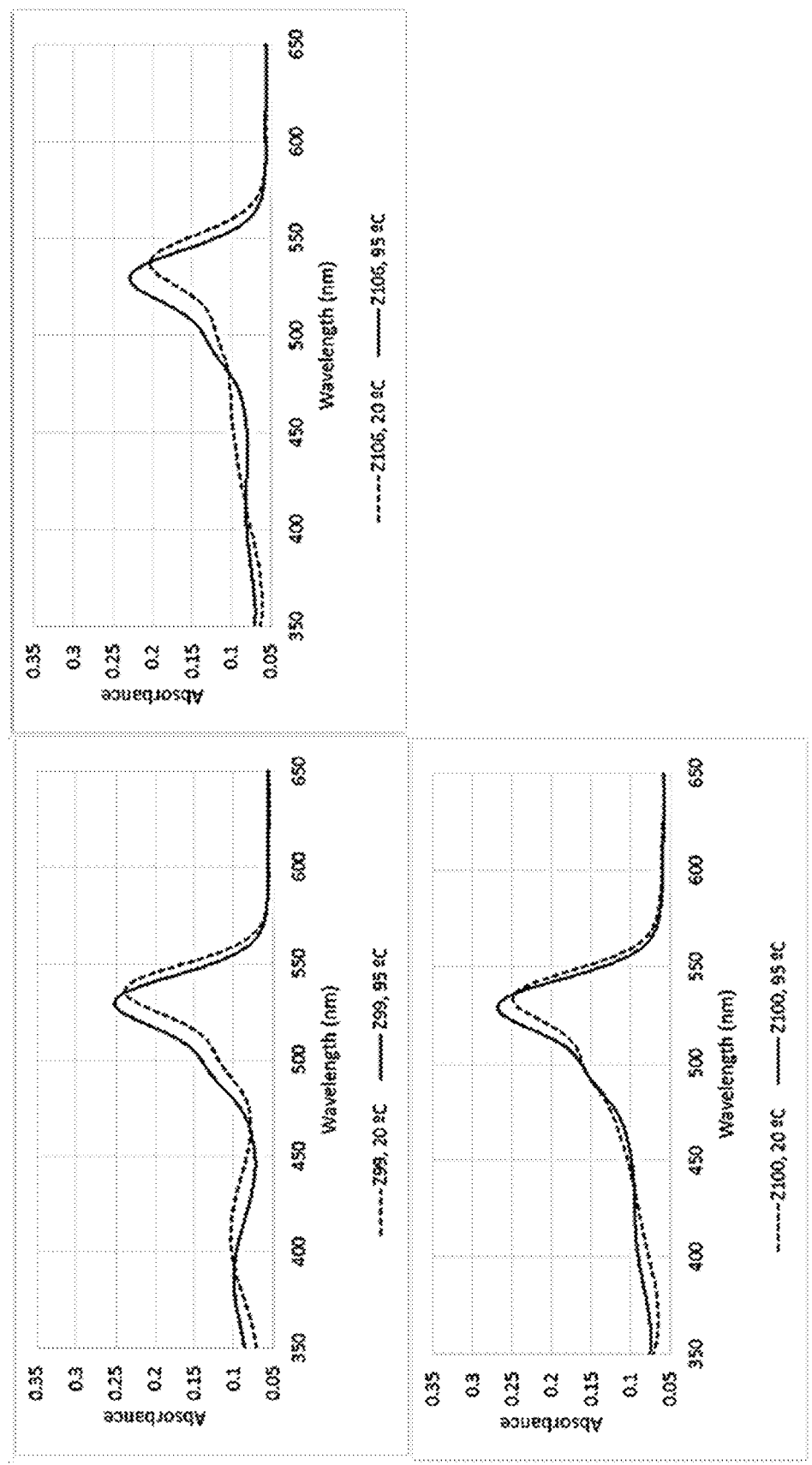
FIG. 11B shows absorption spectra of open (95° C.) and closed (20° C.) forms of an exemplary Molecular Beacon probe labeled with Eclipse (Z28) and various nitrodiarylethene quenchers.

The oligonucleotides of Formula III are efficient Molecular Beacon probes with high hybridization signal and low fluorescence background as illustrated in FIGS. 9 and 10. This example demonstrates that some compounds of the invention generate significantly higher signals compared to the traditional (Z28) quencher. Particularly, the Z99 quencher provides greater than 400% signal increase with insignificant loss of signal-to-background ratio demonstrating that a very efficient quenching can be achieved with no involvement of the FRET mechanism. In this example, the absence of the FRET interaction is postulated from the fact that no overlap of the AP525 emission and the Z99 absorbance spectrum is present (FIG. 10, upper graph). The UV-VIS spectra changes, observed during thermal disassociation of the Molecular Beacon probes (FIG. 11) support the presence of fluorophore-quencher interactions and therefore efficient contact quenching.

In another embodiment, oligonucleotide conjugates of Formula II comprise a minor groove binder. One preferred embodiment of an oligonucleotide configuration in accordance with this disclosure has the structure described by the Formula IV:

Formula IV wherein MGB is a minor groove binder;

Fl is a fluorophore;

ODN is an oligonucleotide; and

Q is a quenching compound of structure —X—(—Ar$^1$—CR$^3$=CR$^4$—)$_n$—Ar$^2$.

This configuration emphasizes that the MGB and fluorophore are covalently attached to one end and the quencher to another end of an oligonucleotide.

MGB-oligonucleotide conjugates can be prepared by post-synthetic conjugation using MGB activated esters or by oligonucleotide synthesis on MGB solid supports as previously described (Lukhtanov et al., 1995 and 1996, U.S. Pat. Nos. 7,564,567, 5,801,155, 6,312,894, 7,205,105, 7,381,818, 7,582,739). Alternatively, MGB phosphoramidites disclosed in US Patent Application Publication No. 20130030166 can also be used. Fluorophore-oligonucleotide conjugates can be prepared, for instance, by using reagents described in U.S. Pat. Nos. 6,972,339, 7,767,834, and 8,163,910. A variety of fluorophore phosphoramidites and solid supports are commercially available from Glen Research. More specifically, oligonucleotide conjugates of Formula IV can be synthesized by analogy with the methods described by Lukhtanov et al. 2007; and U.S. Pat. No. 7,381,818) for MGB Pleiades probes but replacing the Eclipse Quencher with quenching compounds of this invention.

In one embodiment, the oligonucleotides of Formula II could be used in digital PCR and arrays.

Figure 8A:
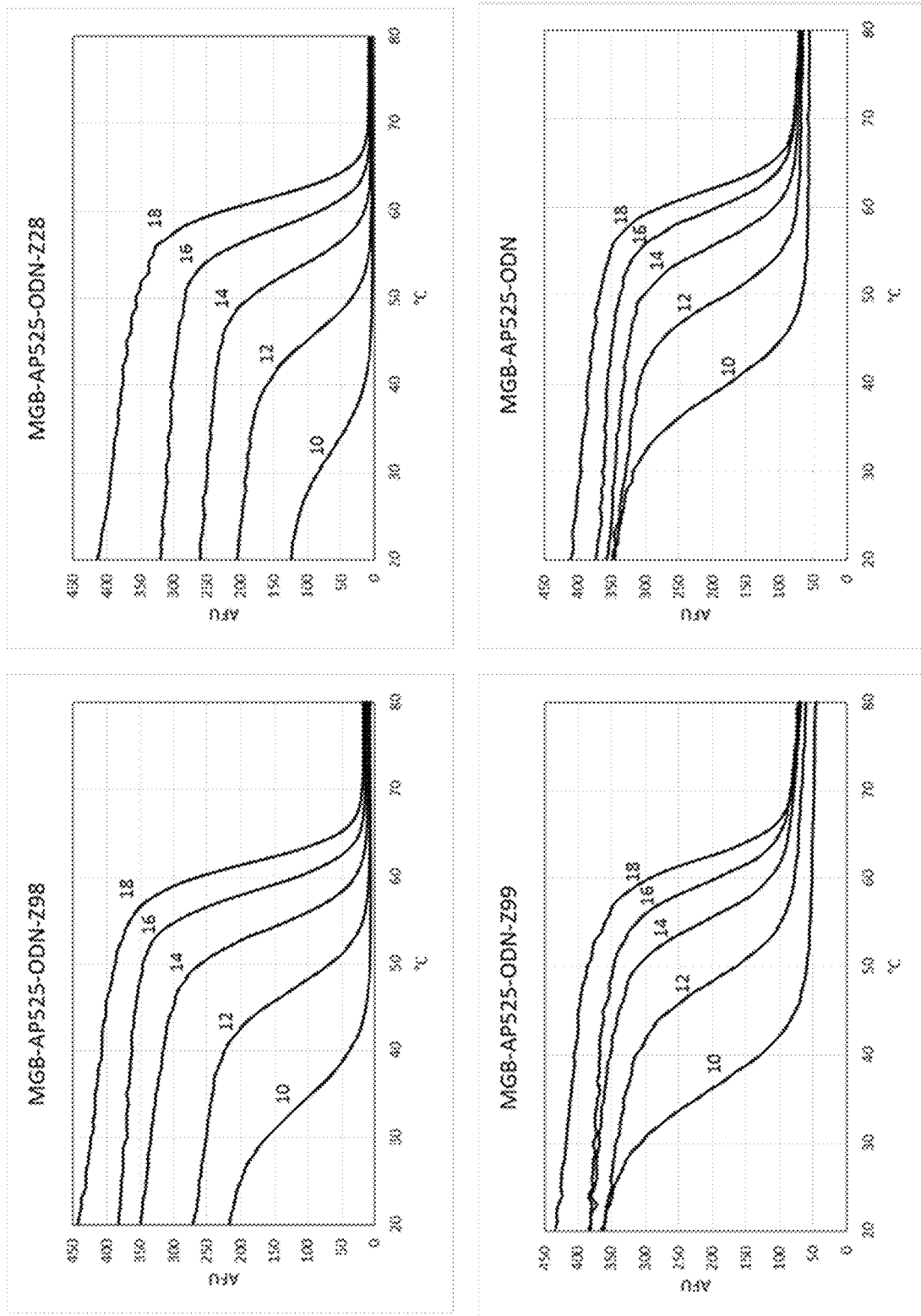
FIG. 8A shows duplex fluorescence of probes of different length and quencher type as a function of temperature.
Figure 8B:
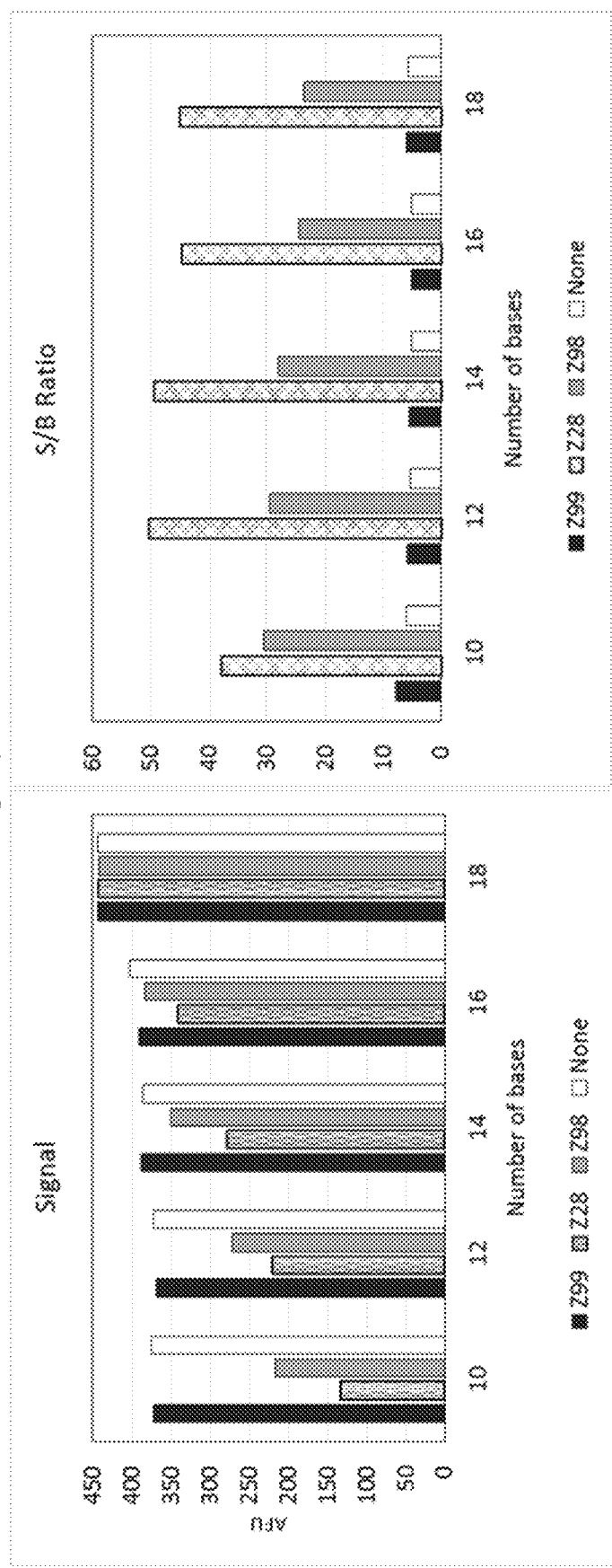
FIG. 8B shows a comparison of fluorescence signal and signal-to-background ratio (S/B) of probes of different length and quencher type, with fluorescence signal and background measured at 20 and 80° C., respectively.

The oligonucleotides of Formula IV are hybridization-triggered fluorogenic probes, which become significantly more fluorescent when hybridized to a target. The previously described MGB Pleiades probes (Lukhtanov et al. 2007) have the same configuration but utilize a different, FRET-based quencher. One major drawback of those probes is that their hybridization signal is highly dependent on probe length. For example, a signal drop of more than 2.5 fold was observed when probe length changed from 18 to 10 bases. Diagnostic assays can benefit from the use of short DNA hybridization probes, which typically demonstrate increased mismatch discrimination leading to improved test specificity. However, the signal drop associated with the use of short FRET-based probes can compromise assay sensitivity. On the contrary, the property of the probes of Formula IV is that their hybridization signal can be made significantly less length-dependent provided that a proper quencher-fluorophore combination is chosen, as illustrated in FIG. 8.

In FIG. 8, homologous 10 to 18-mer probes were labeled with the AP525 fluorophore and MGB at the 5' end and three different quenchers at the 3' end. The probes were annealed to a complementary oligonucleotide template and the resulting DNA duplex then subjected to thermal denaturation. During the denaturation procedure the high fluorescence duplexes transitioned into low fluorescence single strand states. As expected, the probes with the traditional diarylazo-based Z28 quencher had low background fluorescence regardless of probe length but their duplex fluorescence dropped almost three-fold as the probe length was reduced from 18 and 10 bases. On the other hand, the probes containing the novel Z98 quencher showed obvious signal increase, especially in case of the 10 and 12-mer probes. The signal increase was accompanied with a minor reduction in the signal-to-background ratio. The probes containing the Z99 quencher (in accordance with a preferred embodiment described herein) showed even higher hybridization signals and almost no dependence on probe length. However, in this case most of the quenching was due to the MGB quenching effect via the PET mechanism as evidenced by comparison with the no quencher controls. There is a slight improvement (as compared to the no-quencher control) in the signal-to-background ratio for the 10-mer probe indicating that at this length a small contribution of contact quenching begins to take place. Depending on the application, different degrees of quenching, signal intensity and signal-to-background ratio may be required. The examples presented here indicate how using the compounds of the invention an optimal fluorophore-quencher combination, which meets the needs of the application, can be found.

Figure 12A:
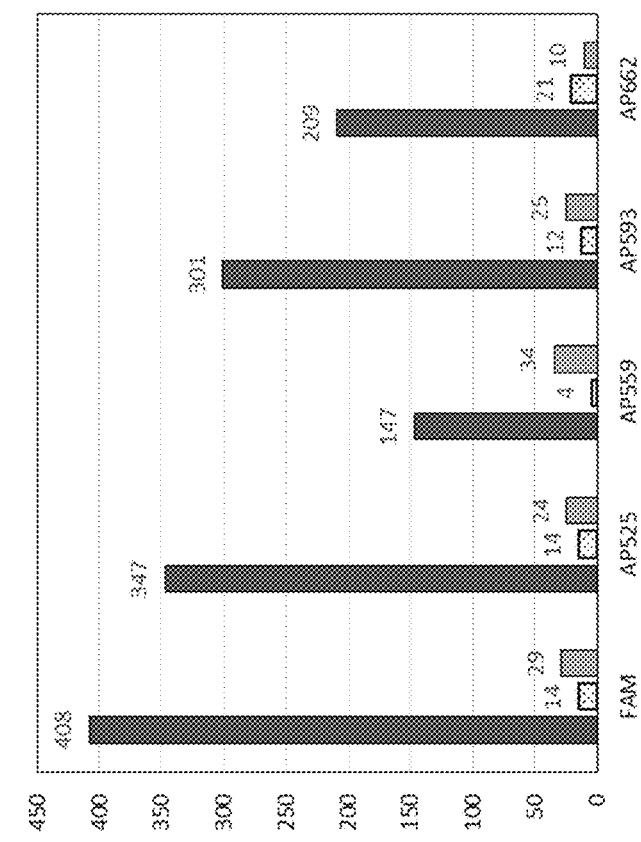
FIG. 12A shows duplex fluorescence (signal), single strand fluorescence (background) and signal-to-background ratio (S/B) of an 11-mer Pleaides probe labeled with FAM, AP525, AP559, AP593 or AP662 and Z101 quenchers.
Figure 12B:
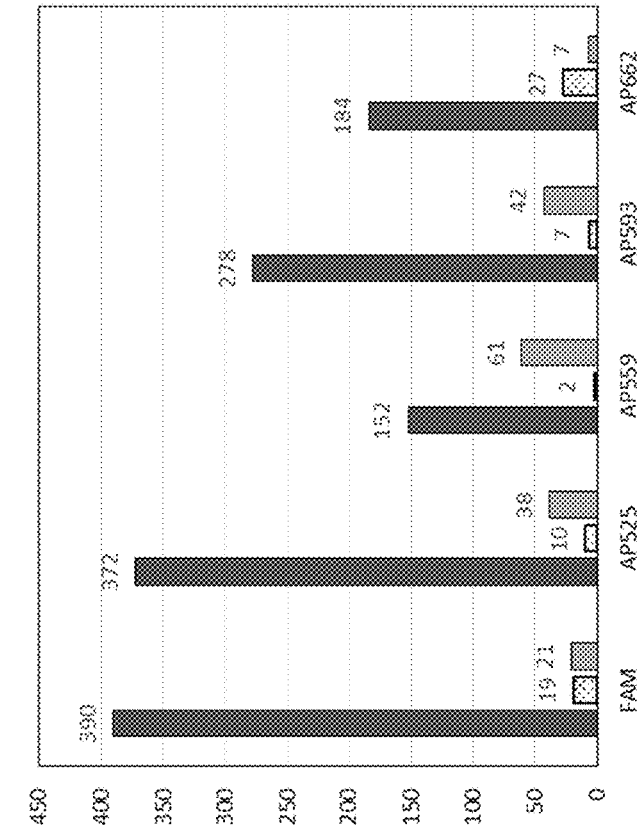
FIG. 12B shows duplex fluorescence (signal), single strand fluorescence (background) and signal-to-background ratio (S/B) of an 11-mer Pleaides probe labeled with FAM, AP525, AP559, AP593 or AP662 and Z106 quenchers.

Another important property of the compounds of the invention is illustrated in FIGS. 12A-12B. It shows that a wide range of fluorophores (FIG. 13B) with their fluorescence spectra stretching from 500-700 nm can be efficiently quenched using the compounds of the invention.

EXAMPLES

Example 1. General Procedure for the Preparation of Formylanilines 2a-c

Figure 14:
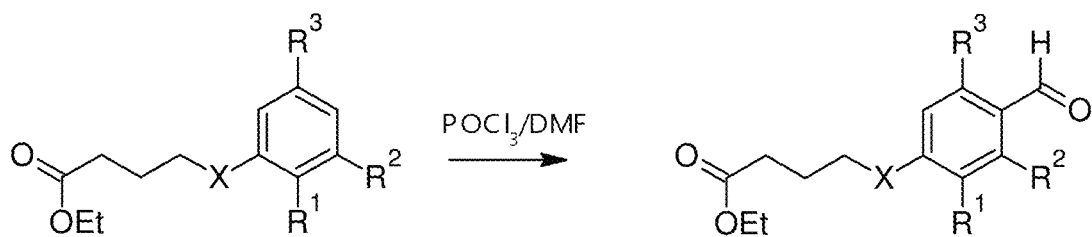
FIG. 14 shows a general reaction scheme for the preparation of formylanilines.

FIG. 14 shows a general reaction scheme for the preparation of formylanilines 2a-c. Phosphorus oxychloride (2.1 g, 13.5 mmol) was added dropwise over 5 min to cold (ice-water bath) anhydrous DMF (10 ml). The flask was removed from the bath and allowed to sit at room temperature for 15 min. Another 10 ml of DMF was added and the reaction was returned to the ice-water bath. After cooling to ~0° C., a solution of 7.2 mmol of 1a-c (1a, Malicka, J. M. et al 2013); (1b and 1c U.S. Pat. No. 8,637,658) in 10 ml of DMF was added dropwise over 5 min. The reaction was removed from the cold bath, heated at 50° C. for 90 min, then cooled and poured into a cold (~0° C.) solution of sodium acetate (10 g) in 60 ml of water. The resultant emulsion was heated with stirring at 100° C. for 15 min, then cooled and neutralized with 1N NaOH to a pH of ~6. The precipitated oil was extracted with ether (2×100 ml). The extract was washed with brine, dried over MgSO$_4$ and concentrated to give crude aldehydes 2a-c, which then were purified by silica gel chromatography eluting with a mixture of ethyl acetate and hexane. Concentration of the pure product fractions afforded aldehydes 2a (1.45 g, 81%), 2b (1.8 g, 77%) and 2c (1.1 g, 49%) as light yellow oils.

2a: $^1$H NMR (CDCl$_3$) δ 9.73 (s, 1H), 7.73 (d, J=8.7 Hz, 2H), 6.73 (d, J=8.7 Hz, 2H), 4.14 (q, J=6.7 Hz, 2H), 3.48 (t, J=7.5 Hz, 2H), 3.06 (s, 3H), 2.36 (t, J=6.9 Hz, 2H), 1.95 (p, J=7.2 Hz, 2H), 1.26 (t, J=7.2 Hz, 3H).

2b: $^1$H NMR (DMSO-d6) δ 10.08 (s, 1H), 7.10 (s, 1H), 6.48 (s, 1H), 4.04 (q, J=7.2, 2H), 3.86 (s, 3H), 3.74 (s, 3H), 3.41 (m, 4H), 2.32 (t, J=7.2 Hz, 2H), 1.77 (p, J=7.5 Hz, 2H), 1.16 (t, J=7.2 Hz, 3H), 1.09 (t, J=7.2 Hz, 3H).

2c: $^1$H NMR (CDCl$_3$) δ 10.22 (s, 1H), 9.32 (dd, J$_1$=8.4 Hz, J$_2$=0.6 Hz, 1H), 8.21 (dd, J$_1$=8.7 Hz, J$_2$=1.2 Hz, 1H), 7.88 (d, J=7.8 Hz, 1H), 7.65 (m, 1H), 7.55 (m, 1H), 7.17 (d, J=7.8 Hz, 1H), 4.07 (q, J=7.2 Hz, 2H), 3.54 (m, 4H), 2.33 (t, J=7.2 Hz, 2H), 1.90 (p, J=7 Hz, 2H), 1.20 (t, J=7.2 Hz, 3H), 1.13 (t, J=7.2 Hz, 3H).

Example 2. General Procedure for the Preparation of Benzaldehydes 2d and 2e

Figure 15:
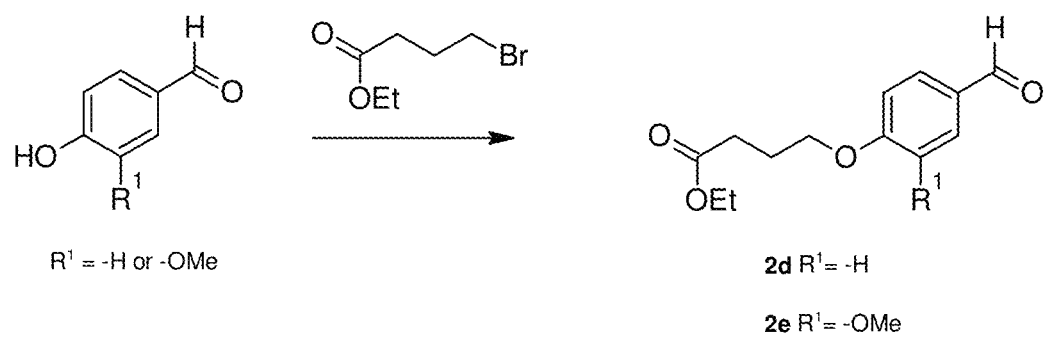
FIG. 15 shows a general scheme for the preparation of benzaldehydes.

FIG. 15 shows a general scheme for the preparation of benzaldehydes 2d and 2e. A solution of 4-hydroxybenzaldehyde or 4-hydroxy-3-methoxybenzaldehyde (55 mmol), ethyl 4-bromobutyrate (8.9 ml, 63 mmol), 1,8-diazabicyclo [5,4,0]undec-7-ene (10 ml, 66 mol) in 100 ml of anhydrous acetonitrile was heated with stirring at 80° C. (bath temperature) for 24 h. The reaction was cooled, concentrated and partitioned between ethyl acetate and 10% citric acid. The organic layer was washed with 10% citric acid, brine, dried over Na$_2$SO$_4$ and concentrated. The crude products were purified either by silica gel chromatography (2d) eluting with 30% ethyl acetate in hexane or crystallization (2e) from ethyl acetate/hexane to afford 10.1 g (78%) of 2d as a colorless liquid or 9.8 g (66%) of 2e as an off-white solid.

2d: 1H NMR (DMSO-d6) δ 9.86 (s, 1H), 7.85 (d, J=8.7 Hz, 2H), 7.11 (d, J=8.7 Hz, 2H), 4.08 (m, 4H), 2.46 (t, J=7.5 Hz, 2H), 1.99 (p, J=7 Hz, 2H), 1.17 (t, J=7.2 Hz, 3H).

2e: $^1$H NMR (DMSO-d6) δ 9.84 (s, 1H), 7.53 (dd, J$_1$=8.1 Hz, J$_2$=1.8 Hz, 1H), 7.39 (d, J=1.8 Hz, 1H), 7.17 (d, J=8.4 Hz, 1H), 4.08 (m, 4H), 3.84 (s, 3H), 2.47 (t, J=7.2 Hz, 2H), 2.01 (p, 7 Hz, 2H), 1.18 (t, J=7.2 Hz, 3H).

Figure 16:
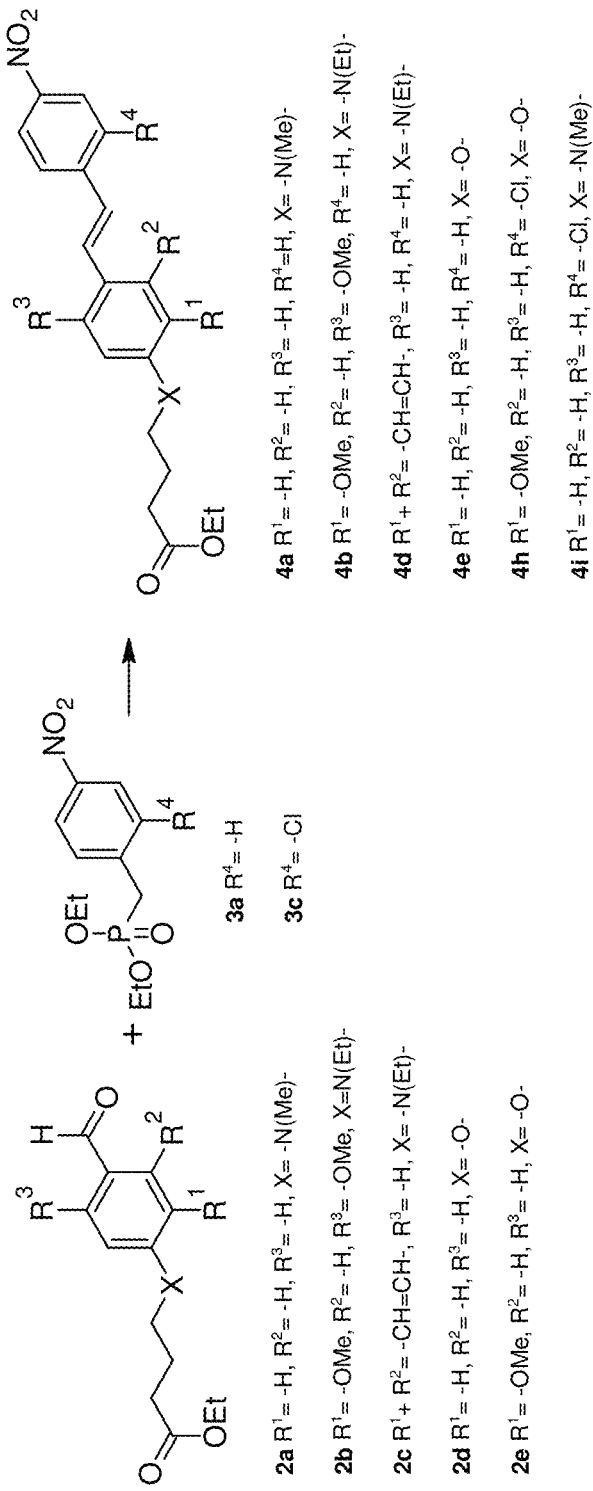
FIG. 16 shows a general scheme for the preparation of nitrostilbenes.

Example 3. General Procedure for the Preparation of Nitrostilbenes 4a, b, d, e, h and i FIG. 16 shows a general scheme for the preparation of nitrostilbenes 4a, b, d, e, h and i. To a mixture of 2 a-e (5.8 mmol) and diethyl (4-nitrobenzyl)phosphonate (3a) (1.74 g, 6.3 mmol) or diethyl (3-chloro-4-nitrobenzyl)phosphonate (3c, synthesized according to US Pat. Application 2013/0261086) (6.3 mmol) was added a solution of sodium ethylate (12 mmol) in 20 ml of anhydrous ethanol. The reaction was agitated for 6-18 h and then treated with solid triethylammonium chloride (2 g) to neutralize excess sodium ethylate. The solvent was removed on a rotary evaporator and the residue partitioned between ethyl acetate and 10% citric acid. The organic phase was washed with brine and dried over Na$_2$SO$_4$. Concentration of the extract gave crude nitrostilbenes 4a, b, d, e, h, i as yellow, orange, red-brown solids (4a, b, e, h, i) or a brown oil (4d). Some of these compounds contained variable amount of respective free acids 5 due to partial saponification during the condensation reaction and were used in the next step without additional purification.

Figure 17:
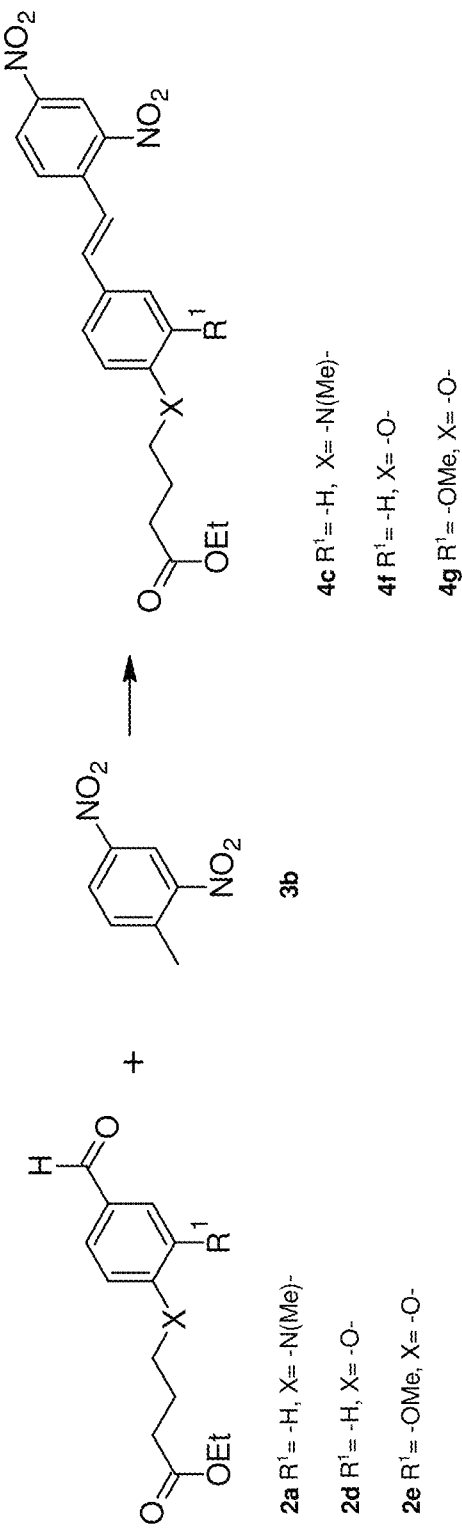
FIG. 17 shows a general scheme for the preparation of dinitrostilbenes.

Example 4. General Procedure for the Preparation of Dinitrostilbenes 4c, f, g FIG. 17 shows a general scheme for the preparation of dinitrostilbenes 4c, f, g. A mixture of 2a, d or e (5.0 mmol), 2,4-dinitrotoluene (1.1 g, 6.0 mmol) and piperidine (0.21 g, 2.5 mmol) was heated with stirring at 80° C. for 3 h, then cooled and dissolved in ethyl acetate. The solution was washed with 10% citric acid, brine, dried over MgSO$_4$ and concentrated. The resultant crude dinitrostilbenes were re-crystallized (4c and f) from ethyl acetate/hexane or purified on silica gel (4 g) eluting with a gradient of ethyl acetate (20-33%) in hexane to afford 1.4 g of 4c (72% yield, black solid), 1.17 g of 4f (58% yield, yellow solid) and 1.4 g of 4 g (65% yield, orange solid).

4c: $^1$H NMR (CDCl$_3$) δ 8.75 (d, J=2.4 Hz, 1H), 8.32 (dd, J$_1$=9 Hz, J$_2$=2.4 Hz, 1H), 7.95 (d, J=8.7 Hz, 1H), 7.45 (d, J=9 Hz, 2H), 7.43 (skewed d, J=15.6 Hz, 1H), 7.28 (skewed d, J=15.9 Hz, 1H), 6.71 (d, J=9 Hz, 2H), 4.15 (q, 6.9 Hz, 2H), 4.44 (t, J=7.5 Hz, 2H), 3.02 (s, 3H), 2.36 (t, J=7.2 Hz, 2H), 1.94 (p, J=7.5 Hz, 2H), 1.27 (t, J=7.2 Hz, 3H).

4f: $^1$H NMR (CDCl$_3$) δ 8.80 (d, J=2.4 Hz, 1H), 8.39 (dd, J$_1$-8.7 Hz, J$_2$=2.4 Hz, 1H), 7.97 (d, J=8.7 Hz, 1H), 7.52 (d, J=8.7 Hz, 2H), 7.48 (skewed d, J=16 Hz, 1H), 7.25 (skewed d, J=16 Hz, 1H), 6.92 (d, J=9 Hz, 2H), 4.15 (q, J=7.2 Hz, 2H), 4.06 (t, J=6 Hz, 2H), 2.54 (t, J=7.2 Hz, 2H), 2.14 (p, J=6.9 Hz, 2H), 1.27 (t, J=7.2 Hz, 3H).

4g: $^1$H NMR (CDCl$_3$) δ 8.80 (d, J=2.4 Hz, 1H), 8, 40 (dd, J1=8.7 Hz, J2=2.4 Hz, 1H), 7.96 (d, J=8.7 Hz, 1H), 7.48 (skewed d, J=16 Hz, 1H), 7.25 (skewed d, J=16 Hz, 1H), 7.12 (skewed dd, J$_1$=8.4 Hz, J$_2$=1.8 Hz, 1H), 7.10 (dd, J=1.8 Hz, 1H), 6.90 (skewed d, J=8.4 Hz, 1H), 4.14 (m, 2H), 3.93 (s, 3H), 2.55 (t, J=7.2 Hz, 2H), 2.19 (p, J=6.6 Hz, 2 h), 1.27 (t, J=7.2 Hz, 3H).

Figure 18:
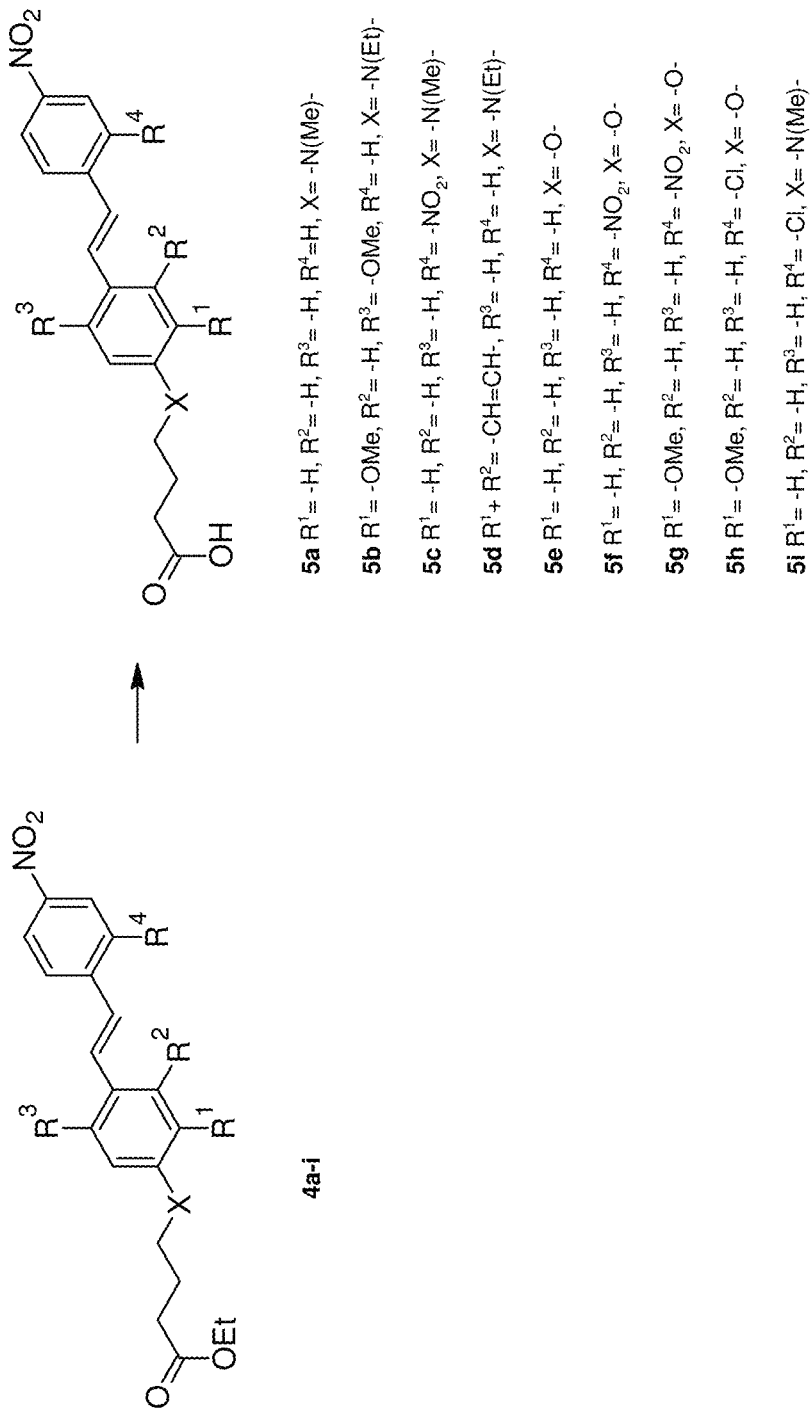
FIG. 18 shows a general scheme for preparation of acids by saponification of ethyl esters.

Example 5. General Procedure for Preparation of Acids 5a-i by Saponification of Ethyl Esters 4a-i FIG. 18 shows a general scheme for preparation of acids 5a-i by saponification of ethyl esters 4a-i To a solution of 4a-g (2-6 mmol) in 60 ml of THF was added 40 ml of MeOH and 20 ml of 1 N NaOH. The reaction was stirred at room temperature for 2-5 hrs until no starting material was found by reverse phase HPLC analysis. The reaction was neutralized by adding 20 ml of 1 N HCl, then concentrated to about 40 ml and diluted with more water (40 ml). The precipitated solid was collected by filtration and washed with water. Drying in vacuo afforded 5a (46% yield from 2a, red-orange solid), 5b (35% yield from 2b, dark brown amorphous solid), 5c (97% yield, dark-purple solid), 5d (77% yield from 2c, brown solid), 5e (43% yield from 2d, red-orange solid), 5f (97% yield, orange solid) or 5 g (92% yield, orange solid).

5a: $^1$H NMR (DMSO-d6) δ 12.13 (s, 1H), 8.17 (d, J=9 Hz, 2H), 7.75 (d, J=8.7 Hz, 2H), 7.50 (d, J=8.7 Hz, 2H), 7.42 (skewed d, J=16 Hz, 1H), 7.10 (skewed d, J=16 Hz, 1H), 6.74 (d, J=9 Hz, 2H), 3.38 (t, J=7.5 Hz, 2H), 2.94 (s, 3H), 2.27 (t, J=7.2 Hz, 2H), 1.75 (p, J=7.5 Hz, 2H).

5b: $^1$H NMR (DMSO-d6) δ 12.7 (br s, 1H), 8.20 (d, J=9 Hz, 2H), 7.75 (d, J=9 Hz, 2H), 7.59 (skewed d, J=16 Hz, 1H), 7.27 (skewed d, J=16 Hz, 1H), 7.24 (s, 1H), 6.57 (s, 1H), 3.83 (s, 3H), 3.80 (s, 3H), 3.20 (t, J=7 Hz, 2H), 3.17 (t, J=7.5 Hz, 2H), 2.33 (t, J=7.2 Hz, 1.68 (p, J=7.5 Hz, 2H), 1.03 (t, J=6.9 Hz, 3H).

5c: $^1$H NMR (DMSO-d6) δ 12.15 (s, 1H), 8.70 (d, J=2.1 Hz, 1H), 8.39 (skewed dd, J$_1$=9 Hz, J$_2$=2.4 Hz, 1H), 8.22 (skewed d, J=9 Hz, 1H), 7.59 (skewed d, J=16 Hz, 1H), 7.50 (d, J=9 Hz, 2H), 7.22 (skewed d, J=16 Hz, 1H), 6.77 (d, J=9 Hz, 2H), 3.41 (t, J=7.2 Hz, 2.97 (s, 3H), 2.27 (t, J=7.2 Hz, 2H), 1.75 (p, J=7.5 Hz, 2H).

5d: $^1$H NMR (DMSO-d6) δ 8.45 (m, 1H), 8.32 (skewed d, J=16 Hz, 1H), 8.23 (m, 3H), 8.01 (d, J=8.7 Hz, 2H), 7.89 (d, J=7.8 Hz, 1H), 7.55 (m, 2H), 7.37 (skewed d, J=16 Hz, 1H), 7.25 (d, J=7.8 Hz, 1H), 3.16 (m, 4H), 1.91 (t, J=7.2 Hz, 2H), 1.61 (p, J=6.9 Hz, 2H), 0.99 (t, J=9 Hz, 3H).

5e: $^1$H NMR (DMSO-d6) δ 12.17 (s, 1H), 8.21 (d, J=8.7 Hz, 2H), 7.81 (d, J=8.7 Hz, 2H), 7.63 (d, J=8.7 Hz, 2H), 7.48 (skewed d, J=16 Hz, 1H), 7.26 (skewed d, J=16 Hz, 1H), 6.97 (d, J=8.7 Hz, 2H), 4.02 (t, J=6.3 Hz, 2H), 2.40 (t, J=7.5 Hz, 2H), 1.95 (p, J=6.9 Hz, 2H).

5f: $^1$H NMR (DMSO-d6) δ 12.18 (s, 1H), 8.72 (d, J=2.1 Hz, 1H), 8.46 (skewed dd, J$_1$=9 Hz, J$_2$=2.4 Hz, 1H), 8.24 (skewed d, J=9 Hz, 1H), 7.62 (d, J=9 Hz, 2H), 7.59 (skewed d, J=16 Hz, 1H), 7.36 (skewed d, J=16 Hz, 1H), 7.01 (d, J=8.7 Hz, 2H), 4.04 (t, J=6.3 Hz, 2H), 2.40 (t, J=7.2 Hz, 2H), 1.95 (p, J=6.9 Hz, 2H).

5g: $^1$H NMR (DMSO-d6) δ 12.17 (s, 1H), 8.72 (d, J=2.1 Hz, 1H), 8.47 (skewed dd, J$_1$=9 Hz, J$_2$=2.4 Hz, 1H), 8.22 (skewed d, J=8.7 Hz, 1H), 7.56 (skewed d, J=16 Hz, 1H), 7.33 (skewed d, J=16 Hz, 1H), 7.28 (d, J=1.8 Hz, 1H), 7.21 (skewed dd, J$_1$=8.4 Hz, J$_2$=1.8 Hz, 1H), 7.02 (skewed d, J=8.4 Hz, 1H), 4.02 (t, J=6.3 Hz, 3.83 (s, 3H), 2.40 (t, J=7.5 Hz, 2H), 1.95 (p, J=6.9 Hz, 2H).

5h: $^1$H NMR (DMSO-d6) δ 12.15 (s, 1H), 8.30 (d, J=2.1 Hz, 1H), 8.18 (skewed dd, J$_1$=9 Hz, J$_2$=2.1, 1H), 8.11

(skewed d, J=9 Hz, 1H), 7.53 (skewed d, J=16 Hz, 1H), 7.36 (skewed d, J=16 Hz, 1H), 7.30 (unresolved d, J~2 Hz, 1H), 7.22 (unresolved dd, $J_1$=9H Hz, $J_2$2 Hz 1H), 7.01 (skewed d, J=9 Hz, 1H), 4.02 (t, J=6.3 Hz, 2H), 3.84 (s, 3H), 2.40 (t, J=7.5 Hz, 2H), 1.95 (p, J=6.9 Hz, 2H).

5i: $^1$H NMR (DMSO-d6) δ 12.12 (s, 1H), 8.24 (d, J=2.1 Hz, 1H), 8.12 (skewed dd, $J_1$=9 Hz, $J_2$=2.1, 1H), 8.06 (skewed d, J=9 Hz, 1H), 7.50 (d, J=9H, 2H), 7.48 (skewed d, J=16, 1H), 7.18 (skewed d, J=16, 1H), 6.75 (d, J=9 Hz, 2H), 3.39 (t, J=7.2 Hz, 2H), 2.95 (s, 3H), 2.67 (t, J=7.2 Hz, 2H), 1.92 (m, 2H).

Example 6. General Procedure for the Preparation of PFP Esters 6a-i

Figure 19:
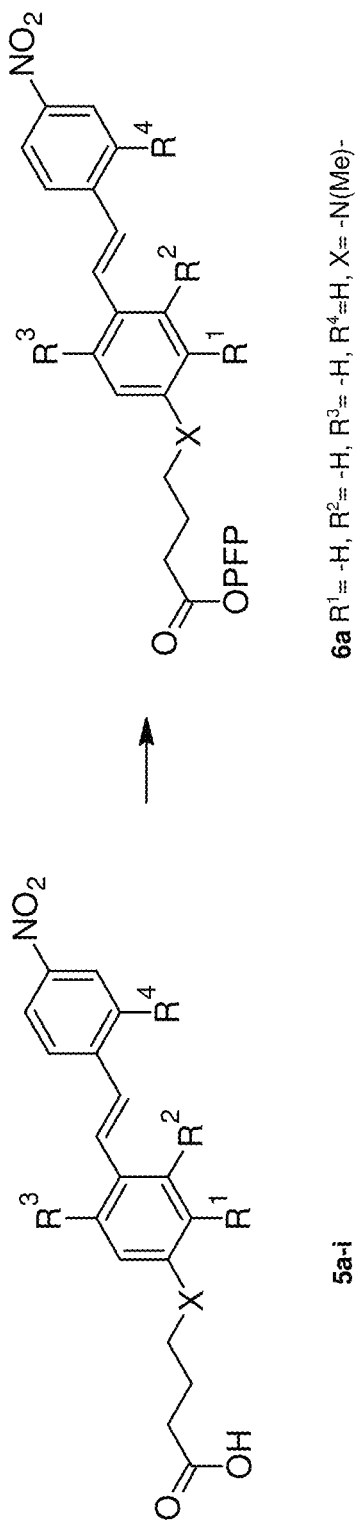
FIG. 19 shows a general scheme for the preparation of PFP esters.

FIG. 19 shows a general scheme for the preparation of PFP esters 6a-i. To a suspension of a carboxylic acid 5a-g (3 mmol) in 40 ml of anhydrous $CH_2Cl_2$ was added 1 ml of triethylamine followed by 0.67 ml (3.9 mmol) of pentafluorophenyl trifluoroacetate to give a clear solution. The solution was kept at ambient temperature for 2-5 h until no starting material was found by reverse phase HPLC analysis. The reaction was concentrated and re-suspended in 1:1 hexane:ethyl acetate (10-20 ml). The precipitated solid was collected by filtration and washed with 4:1 hexane:ethyl acetate. Alternatively, some of the PFP esters were purified by silica gel chromatography eluting with a mixture of ethyl acetate and hexane. Drying in vacuo afforded 6a (78% yield, orange solid), 6b (91% yield after silica gel chromatography, brown oil), 6c (92% yield, dark-purple solid), 6d (55% yield after silica gel column purification, orange solid), 6e (59% yield, yellow solid), 6f (69% yield, yellow solid), 6g (76% yield, orange solid), 6h (72% yield, yellow solid) or 6i (73% yield, dark brown solid).

6a: $^1$H NMR (DMSO-d6) δ 8.18 (d, J=8.7 Hz, 2H), 7.76 (d, J=8.7 Hz, 2H), 7.51 (d, J=9 Hz, 2H), 7.43 (skewed d, J=16 Hz, 1H), 7.12 (skewed d, J=16 Hz, 1H), 6.77 (d, J=9 Hz, 2H), 3.47 (t, J=6.9 Hz, 2H), 2.97 (s, 3H), 2.88 (t, J=7.2 Hz, 2H), 1.91 (p, J=7.2 Hz, 2H).

6b: $^1$H NMR (DMSO-d6) δ 8.20 (d, J=9 Hz, 2H), 7.75 (d, J=9 Hz, 2H), 7.59 (skewed d, J=16 Hz, 1H), 7.28 (skewed d, J=16 Hz, 1H), 7.26 (s, 1H), 6.58 (s, 1H), 3.83 (s, 3H), 3.81 (s, 3H), 3.23 (m, 4H), 2.82 (t, J=6.9 Hz, 2H), 1.85 (p, J=7.2 Hz, 2H), 1.04 (t, J=6.9 Hz, 3H).

6c: $^1$H NMR (CDCl$_3$) δ 8.77 (d, J=2.4 Hz, 1H), 8.34 (skewed dd, J1=9 Hz, J2=2.4 Hz, 1H), 7.96 (d, J=9 Hz, 2H), 7.47 (d, 9 Hz, 1H), 7.44 (skewed d, J=16 Hz, 1H), 7.29 (skewed d, J=16 Hz, 1H), 6.72 (d, J=9 Hz, 2H), 3.53 (t, J=7.2 Hz, 2H), 3.06 (s, 3H), 2.75 (t, J=7.2 Hz, 2H), 2.09 (p, J=7.2 Hz, 2H).

6d: $^1$H NMR (DMSO-d6) δ 8.45 (m, 1H), 8.32 (skewed d, J=16 Hz, 1H), 8.25 (m, 3H), 8.02 (d, J=8.7 Hz, 2H), 7.92 (d, J=8.1 Hz, 2H), 7.58 (m, 2H), 7.40 (skewed d, J=16 Hz, 1H), 7.32 (d, J=8.1 Hz, 2H), 3.29 (t, J=6.9 Hz, 2H), 3.18 (q, J=7.2 Hz, 2H), 2.81 (t, J=6.9 Hz, 2H), 1.84 (p, J=6.9 Hz, 2H), 1.02 (t, J=7.2 Hz, 3H).

6e: $^1$H NMR (DMSO-d6) δ 8.22 (d, J=8.7 Hz, 2H), 7.82 (d, J=8.7 Hz, 2H), 7.62 (d, J=8.4 Hz, 2H), 7.49 (skewed d, J=16 Hz, 2H), 7.27 (skewed d, J=16 Hz, 1H), 6.99 (d, J=8.4 Hz, 2H), 4.11 (t, J=6 Hz, 2H), 2.98 (t, J=7.2 Hz, 2H), 2.14 (p, J=6.3 Hz, 2H).

6f: $^1$H NMR (CDCl$_3$) δ 8.80 (d, J=2.4 Hz, 1H), 8.40 (skewed dd, $J_1$=8.4 Hz, $J_2$=2.1 Hz, 1H), 7.97 (skewed d, J=8.4 Hz, 1H), 7.53 (d, J=8.7 Hz, 2H), 7.52 (skewed d, J=16 Hz, 1H), 7.27 (skewed d, J=16 Hz, 1H), 6.94 (d, J=8.7 Hz, 2H), 4.13 (t, J=6 Hz, 2H), 2.94 (t, J=7.5 Hz, 2H), 2.29 (p, J=6 Hz, 2H).

6g: $^1$H NMR (CDCl$_3$) δ 8.80 (d, J=2.4 Hz, 1H), 8.40 (dd, $J_1$=8.4 Hz, $J_2$=2.4 Hz, 1H), 7.97 (d, J=8.7 Hz, 1H), 7.50 (skewed d, J=16 Hz, 1H), 7.25 (skewed d, J=16 Hz, 1H), 7.13 (d, J=8 Hz, 1H), 7.11 (s, 1H), 6.92 (d, J=8 Hz, 1H), 4.18 (t, J=6 Hz, 2H), 3.94 (s, 3H), 2.97 (t, J=7.2 Hz, 2H), 2.35 (p, J=7 Hz, 2H).

6h: $^1$H NMR (DMSO-d6) δ 8.29 (d, J=2.1 Hz, 1H), 8.18 (skewed dd, $J_1$=9 Hz, $J_2$=2.1, 1H), 8.10 (skewed d, J=9 Hz, 1H), 7.52 (skewed d, J=16 Hz, 1H), 7.36 (skewed d, J=16 Hz, 1H), 7.30 (unresolved d, J~2 Hz, 1H), 7.23 (unresolved dd, $J_1$=9H Hz, $J_2$2 Hz 1H), 7.02 (skewed d, J=9 Hz, 1H), 4.10 (t, J=6.3 Hz, 2H), 3.84 (s, 3H), 2.98 (t, J=7.2 Hz, 2H), 2.13 (p, J=6.9 Hz, 2H).

6i: $^1$H NMR (DMSO-d6) δ 8.26 (d, J=2.1 Hz, 1H), 8.14 (skewed dd, $J_1$=9 Hz, $J_2$=2.1, 1H), 8.08 (skewed d, J=9 Hz, 1H), 7.52 (d, J=9H, 2H), 7.50 (skewed d, J=16 Hz, 1H), 7.20 (skewed d, J=16 Hz, 1H), 6.78 (d, J=9 Hz, 2H), 3.48 (t, J=7.2 Hz, 2H), 2.98 (s, 3H), 2.87 (t, J=7.2 Hz, 2H), 1.92 (p, J=7.2 Hz, 2H).

Figure 20:
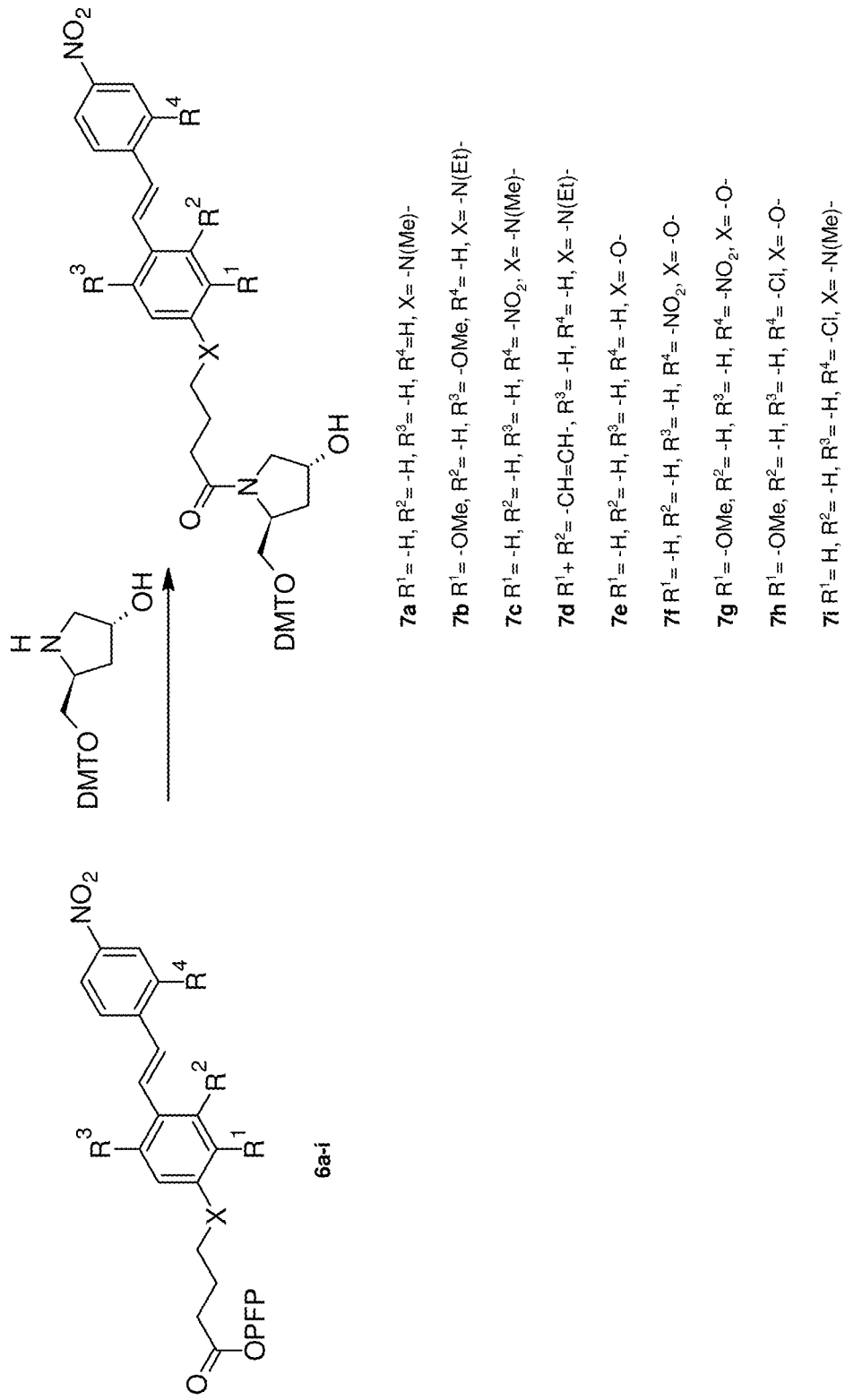
FIG. 20 shows a general scheme for the preparation of DMT-hydroxyprolinol stilbenes.

Example 7. General Procedure for the Preparation of DMT-Hydroxyprolinol Stilbenes 7a-i FIG. 20 shows a general scheme for the preparation of DMT-hydroxyprolinol stilbenes 7a-i.

(1) Preparation of 5-dimethoxytrityloxymethyl-3-hydroxypyrrolidine

A solution of N-Fmoc-5-dimethoxytrityloxymethyl-3-hydroxypyrrolidine (1.28 g, 2 mmol) in a mixture of DMF (12 ml) and TEA (12 ml) was heated at 80° C. for 1 h then concentrated to an oil and re-dissolved in DMF (25 ml) and TEA (0.5 ml). The solution of crude 5-dimethoxytrityloxymethyl-3-hydroxypyrrolidine was promptly used in the next step without additional purification.

(2) Coupling of PFP esters 6 with 5-dimethoxytrityloxymethyl-3-hydroxypyrrolidine The solution of crude 5-dimethoxytrityloxymethyl-3-hydroxypyrrolidine from step 1 was added to a flask containing 1.75 mmol of PFP ester 6. The flask was swirled until a clear solution was obtained. After being stirred at room temperature for a total of 3 h the reaction was concentrated, re-dissolved in ethyl acetate (100-150 ml), washed with dilute NaHCO$_3$, then brine and dried over Na$_2$SO$_4$. The drying agent was removed by filtration and the filtrate concentrated. The resultant material was then chromatographed on silica eluting with ethyl acetate followed by 10% acetone in ethyl acetate. Concentration of the pure product fractions afforded 7a (98% yield, yellow amorphous solid), 7b (95% yield, brown-red amorphous solid), 7c (98% yield, dark-purple amorphous solid), 7d (100% yield, orange amorphous solid), 7e (100% yield, yellow amorphous solid), 7f (100% yield, yellow amorphous solid), 7g (96% yield, orange amorphous solid), 7h (97% yield, yellow amorphous solid) or 7i (93% yield, yellow amorphous solid).

7a (mixture of amide rotamers (3:1)): $^1$H NMR (DMSO-d6) δ 8.18 (d, J=8.7 Hz, 2H), 7.77 (1:3 d+d, J=8.7 Hz, 2H), 7.47 (1:3 d+d, J=8.7 Hz, 2H), 7.41 (skewed 1:3 d+d, J=16 Hz, 1H), 7.31 (m, 4H), 7.28 (s, ¾ H), 7.25 (s, ¼ H), 7.2 (m, 4H), 7.09 (skewed 1:3 d+d, J=16 Hz, 1H), 6.87 (m, 4H), 6.76 (d, J=9 Hz, ¾ 2H), 6.68 (d, J=9 Hz, ¼ 2H), 5.02 (d, J=3.9 Hz, ¾H), 4.92 (d, J=3.9 Hz, ¼ H), 4.39 (m, ¾H), 4.31 (m, ¼ H), 4.20 (m, ¾H), 4.10 (m, ¼ H), 3.72 (s, 1.5H), 3.71 (s, ¼ 3H), 3.69 (s, ¾ 3H), 3.6-3.4 (m, 1H), 3.4-3.1 (m, 4H), 3.0 (m, 1H), 2.94 (s, ¾ 3H), 2.87 (s, ¼ 3H), 2.29 (t, J=6.9 Hz, 2H), 2.1-1.6 (m, 4H).

7b (mixture of amide rotamers (3:1)): $^1$H NMR (DMSO-d6) δ 8.19 (d, J=9 Hz, 2H), 7.74 (d, J=9 Hz, 2H), 7.60

(skewed d, J=16 Hz, 1H), 7.4-7.1 (m, 11H), 6.9-6.8 (m, 4H), 6.63 (s, ¾H), 6.56 (s, ¼ H), 5.00 (d, J=3.9 Hz, ¾H), 4.91 (d, J=3.9 Hz, ¼ H), 4.39 (m, ¾H), 4.30 (m, ¼ H), 4.16 (m, H), 3.85-3.35 (mixture of s, 12H), 3.59 (m, ¾H), 3.45 (m, ¼ H), 3.35-3.0 (m, 6H), 2.97 (m, 1H), 2.26 (t, J=6.9 Hz, 2H), 2.00 (m, 1H), 1.84 (m, 1H), 1.67 (m, 2H), 1.00 (m, 3H).

7c (mixture of amide rotamers (3:1)): $^1$H NMR (DMSO-d6) δ 8.70 (d, J=2.4 Hz, 1H), 8.41 skewed dd, $J_1$=8.7 Hz, $J_2$=2.4 Hz, 1H), 7.89 (d, J=16 Hz, ¼ H), 7.85 (d, J=16 Hz, ¾H), 7.47 (d, J=9 Hz, 2H), 7.35-7.15 (m, 10H), 6.87 (m, 4H), 6.79 (d, J=8.7 Hz, ¾ 2H), 6.70 (d, J=8.7 Hz, ¼ 2H), 5.01 (d, J=3.9 Hz, ¾H), 4.92 (d, J=3.9 Hz, ¼ H), 4.39 (m, ¾H), 4.31 (m, ¼ H), 4.18 (m, ¾H), 4.10 (m, ¼ H), 3.72 (s, 1.5H), 3.70 (s, ¾ 3H), 3.69 (s, ¾ 3H), 3.6-3.45 (m, 1H), 3.45-3.15 (m, 4H), 3.0 (m, 1H), 2.96 (s, ¾ 3H), 2.90 (s, ¼ 3H), 2.29 (t, J=6.9 Hz, 2H), 2.1-1.6 (m, 4H).

7d (mixture of amide rotamers (3:1)): $^1$H NMR (DMSO-d6) δ 8.43 (d, J=8.1 Hz, 1H), 8.32 (d, J=16 Hz, 1H), 8.3-8.1 (m, 3H), 8.02 (d, J=8.7 Hz, 2H), 7.90 (d, J=8.1 Hz, 1H), 7.60-7.42 (m, 2H), 7.37 (d, J=16 Hz, 1H), 7.3-7.1 (m, 10H), 6.83 (m, 4H), 4.99 (d, J=3.9 Hz, ¾H), 4.89 (d, J=3.9 Hz, ¼ H), 4.37 (m, ¾H), 4.35 (m, ¼ H), 4.12 (m, ¾H), 4.10 (m, ¼ H), 3.70 (s, 6H), 3.53 (m, ¾H), 3.45 (m, ¼ H), 3.35-3.0 (m, 6H), 2.95 (m, 1H), 2.24 (t, J=7.2 Hz, 2H), 2.00 (m, 1H), 1.84 (m, 1H), 1.64 (m, 2H), 0.99 (m, 3H).

7e (mixture of amide rotamers (3:1)): $^1$H NMR (DMSO-d6) δ 8.21 (d, J=9 Hz, 2H), 7.82 (d, J=9 Hz, 2H), 7.59 (d, J=8.7 Hz, 2H), 7.49 (skewed d, J=16 Hz, ¼ H), 7.48 (skewed d, J=16 Hz, ¾H), 7.3 (m, 5H), 7.2 (m, 5H), 6.97 (d, J=9 Hz, 1.5H), 6.9 (m, 4.5H), 5.00 (d, J=3.9 Hz, ¾H), 4.92 (d, J=3.9 Hz, ¼ H), 4.42 (m, ¾H), 4.30 (m, ¼ H), 4.19 (m, 1H), 4.05 (m, 1H), 3.92 (m, 1H), 3.72 (mixture of s, 6H), 3.65-3.45 (m, 1H), 3.45-3.15 (m, 2H), 3.0 (m, 1H), 2.44 (t, J=6.9 Hz, 2H), 2.2-1.7 (m, 4H).

7f (mixture of amide rotamers (3:1)): $^1$H NMR (DMSO-d6) δ 8.74 (d, J=2.4 Hz, 1H), 8.48 (dd, $J_1$=8.7 Hz, $J_2$=2.4 Hz, 1H), 8.25 (d, J=8.7 Hz, 1H), 7.6 (m, 3H), 7.4-7.3 (m, 10H), 6.99 (d, J=8.7 Hz, ¾ 2H), 6.92 (d, J=8.7 Hz, ¼ 2H), 6.87 (d, J=9 Hz, 4H), 5.03 (d, J=3.9 Hz, ¾ H), 4.92 (d, J=3.9 Hz, ¼ H), 4.42 (m, ¾ H), 4.30 (m, ¼ H), 4.19 (m, 1H), 4.05 (m, 1H), 3.93 (m, 1H), 3.72 (mixture of s, 6H), 3.65-3.45 (m, 1H), 3.45-3.15 (m, 2H), 3.0 (m, 1H), 2.42 (t, J=6.9 Hz, 2H), 2.2-1.8 (m, 4H).

7g (mixture of amide rotamers (3:1)): $^1$H NMR (CDCl$_3$) δ 8.80 (d, J=2.4 Hz, 1H), 8.39 (dd, $J_1$=8.7 Hz, $J_2$=2.4 Hz, 1H), 7.96 (d, J=8.7 Hz, 1H), 7.48 (skewed d, J=16 Hz, 1H), 7.4-7.05 (m, 12H), 6.91 (m, 1H), 6.8 (m, 4H), 4.64 (m, ¾ H), 4.50 (m, ¼ H), 4.41 (m, 1H), 4.25-4.05 (m, 2H), 3.91 (s, ¾ 3H), 3.85 (s, ¼ 3H), 3.76 (s, 6H), 3.75 (m, 1H), 3.6-3.4 (m, 2H), 3.15 (m, 1H), 2.50 (m, 2H), 2.20 (m, 3H), 1.95 (m, 1H).

7h (mixture of amide rotamers (3:1)): $^1$H NMR (DMSO-d6) δ 8.30 (d, J=2.1 Hz, 1H), 8.20 (skewed dd, $J_1$=9 Hz, $J_2$=2.1, 1H), 8.11 (skewed d, J=9 Hz, 1H), 7.54 (skewed d, J=16 Hz, 1H), 7.4-7.10 (m, 12H), 6.91 (m, 1H), 6.86 (d, J=8.6 Hz, 4H), 5.07 (d, J=4.2 Hz, ¾ H), 4.91 (d, J=4.2 Hz, ¼ H), 4.42 (m, ¾ H), 4.30 (m, ¼ H), 4.18 (m, 1H), 4.05 (m, 1H), 3.92 (m, 1H), 3.82 (s, ¾ 3H), 3.78 (s, ¼ 3H), 3.71 (mixture of s, 6H), 3.65-3.45 (m, 1H), 3.45-3.15 (m, 2H), 3.0 (m, 1H), 2.42 (t, J=6.9 Hz, 2H), 2.2-1.8 (m, 4H).

7i (mixture of amide rotamers (3:1)): $^1$H NMR (DMSO-d6) δ 8.26 (d, J=2.1 Hz, 1H), 8.14 (skewed dd, $J_1$=9 Hz, $J_2$=2.1, 1H), 8.09 (skewed d, J=9 Hz, 1H), 7.56-7.44 (m, 3H), 7.36-7.24 (m, 4H), 7.24-7.14 (m, 6H), 6.87 (m, 4H), 6.76 (d, J=9 Hz, ¾ 2H), 6.70 (d, J=9 Hz, ¼ 2H), 5.00 (d, J=3.9 Hz, ¾ H), 4.91 (d, J=3.9 Hz, ¼H), 4.39 (m, ¾H), 4.31 (m, ¼ H), 4.20 (m, ¾H), 4.10 (m, ¼H), 3.70 (mixture of s, 6H), 3.6-3.45 (m, 1H), 3.4-3.1 (m, 4H), 3.0 (m, 1H), 2.88 (s, 3H), 2.29 (t, J=6.9 Hz, 2H), 2.1-1.6 (m, 4H).

Figure 21:
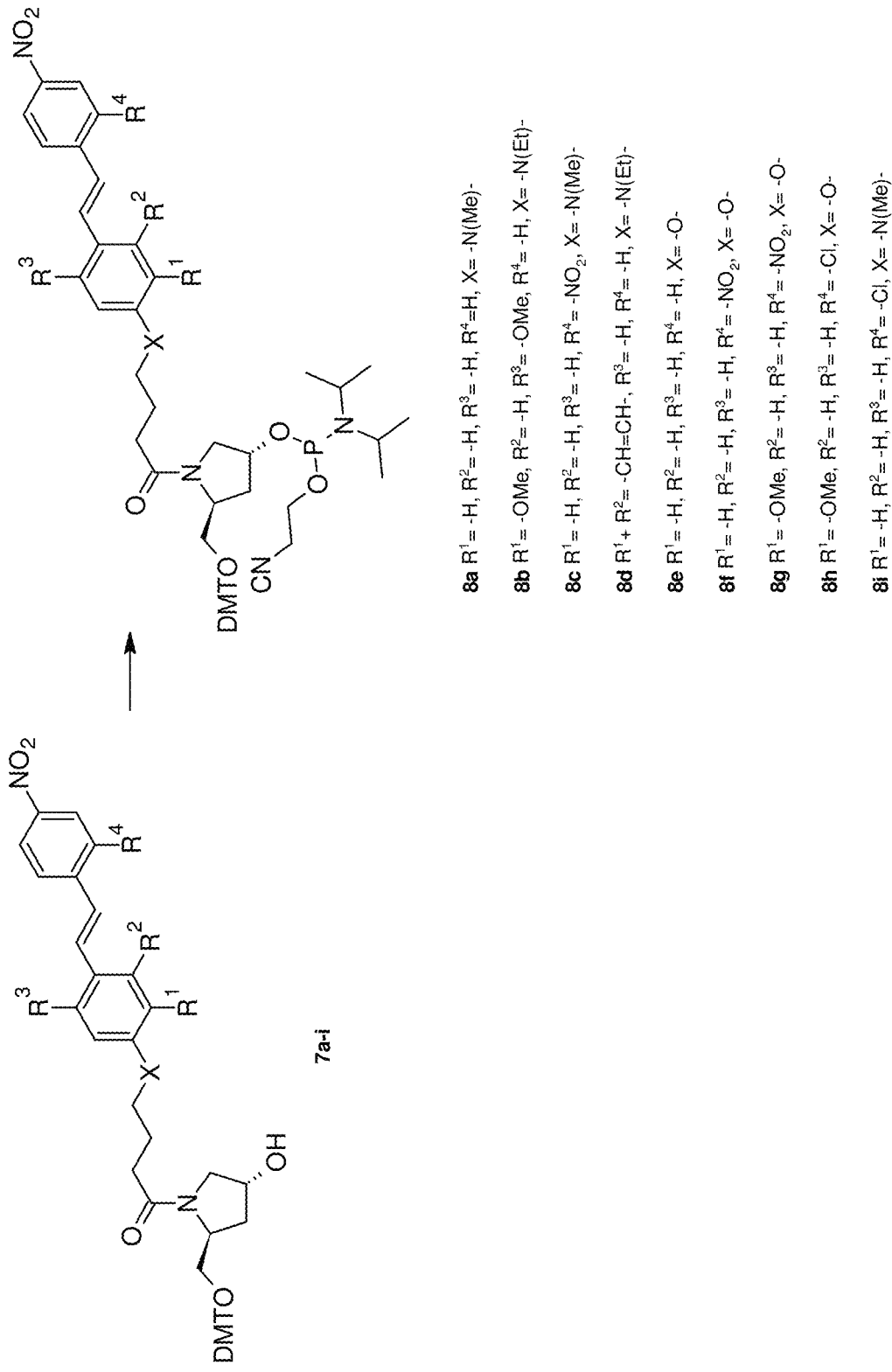
FIG. 21 shows a general scheme for the preparation of DMT-hydroxyprolinol stilbene phosphoramidites.

Example 8. General Procedure for the Preparation of DMT-Hydroxyprolinol Stilbene Phosphoramidites 8a-i FIG. 21 shows a general scheme for the preparation of DMT-hydroxyprolinol stilbene phosphoramidites 8a-i. Diisopropylaminium tetrazolide (2 mmol) was added to a solution of a DMT-hydroxyprolinol stilbenes 7a-g (2 mmol) in 30 ml of anhydrous CH$_2$Cl$_2$ followed by 2-cyanoethyl N,N,N'N'-tetraisopropylphosphordiamidite (2.3 mmol). The reaction was agitated for 5-15 h and analyzed by reverse phase HPLC. Additional 2-cyanoethyl N,N,N'N'-tetraisopropylphosphordiamidite was added if necessary. Upon completion the reaction was concentrated and partitioned between ethyl acetate (100-150 ml) and saturated sodium bicarbonate (50-100 ml). The organic phase was washed with brine, dried over Na$_2$SO$_4$ and concentrated. The obtained oil was re-dissolved in approx. 10 ml of EtOAc and precipitated by adding 200 ml of hexane. After allowing the oil to settle down for 10-15 min the liquid was decanted and the residual material re-dissolved in a small amount (3-5 ml) of anhydrous CH$_2$Cl$_2$. Drying in vacuo afforded 8a (90% yield, red amorphous solid), 8b (76% yield, dark brown-red amorphous solid), 8c (86% yield, black amorphous solid), 8d (76% yield, red-orange amorphous solid), 8e (100% yield, yellow amorphous solid), 8f (86% yield, yellow amorphous solid), 8g (91% yield, orange amorphous solid), 8h (94% yield, orange amorphous solid) or 8i (80% yield, purple amorphous solid).

8a (mixture of diastereomers (1:1) and amide rotamers (3:1)) $^{31}$P NMR (DMSO-d6) δ 146.68, 146.41, 146.27, 145.97.

8b (mixture of diastereomers (1:1) and amide rotamers (3:1)) $^{31}$P NMR (DMSO-d6) δ 146.60, 146.45, 146.23, 145.94.

8c (mixture of diastereomers (1:1) and amide rotamers (3:1)) $^{31}$P NMR (DMSO-d6) δ 146.63, 146.38, 146.25, 145.97.

8d (mixture of diastereomers (1:1) and amide rotamers (3:1)) $^{31}$P NMR (DMSO-d6) δ 146.53, 146.34, 146.16, 146.01.

8e (mixture of diastereomers (1:1) and amide rotamers (3:1)) $^{31}$P NMR (DMSO-d6) δ 146.70, 146.45, 146.24, 145.96.

8f (mixture of diastereomers (1:1) and amide rotamers (3:1)) $^{31}$P NMR (DMSO-d6) δ 146.66, 146.42, 14622, 145.94.

8g (mixture of diastereomers (1:1) and amide rotamers (3:1)) $^{31}$P NMR (DMSO-d6) δ 146.66, 146.47, 146.21, 146.00.

8h (mixture of diastereomers (1:1) and amide rotamers (3:1)) $^{31}$P NMR (DMSO-d6) δ 146.69, 146.50, 146.25, 146.04.

8i (mixture of diastereomers (1:1) and amide rotamers (3:1)) $^{31}$P NMR (DMSO-d6) δ 146.70, 146.45, 146.30, 146.04.

Example 9. Ethyl 4-[[4-[(E)-2-[4-(1,3-dioxan-2-yl)phenyl]ethenyl]phenyl]methylamino]butanoate (10)

Figure 22:
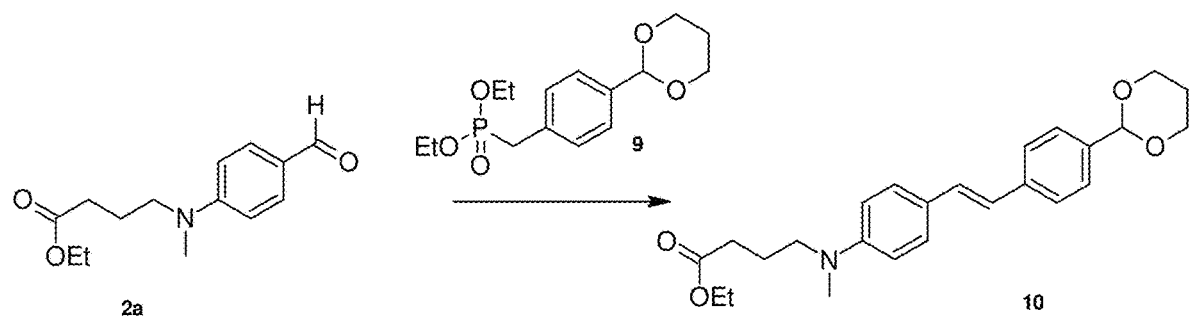
FIG. 22 shows a general scheme for preparation of ethyl 4-[[4-[(E)-2-[4-(1,3-dioxan-2-yl)phenyl]ethenyl]phenyl] methylamino]butanoate (10).

FIG. 22 shows a general scheme for preparation of ethyl 4-[[4-[(E)-2-[4-(1,3-dioxan-2-yl) phenyl]ethenyl]phenyl]methylamino]butanoate (10). To a cold (0-4° C.) solution of diethyl [4-(1,3-dioxan-2-yl)benzyl]phosphonate 9 (Rigamonti, Luca et al Inorganic Chemistry, 2009, 48(8), 3562-3572) (1.65 g, 5.2 mmol) in 100 ml of anhydrous THF was added 1.2 g (10.7 mmol) of potassium tert-butoxide in one portion. The mixture was stirred at 0° C. for 30 min. Ethyl 4-[(4-formylphenyl)(methyl)amino]butanoate (2a) (1.25 g, 5 mmol) was added dropwise via a syringe. After being stirred for 30 min at 0° C. the reaction was treated with a 0.3 g (0.94 mmol) portion of 9 followed by another 0.3 g portion in 1 h. The reaction was concentrated and partitioned between ethyl acetate and saturated NaHCO$_3$. The organic phase was washed with brine, dried over Na$_2$SO$_4$ and concentrated. The resultant oil was chromatographed on silica eluting with 3:1 hexane/ethyl acetate to afford 0.5 g (24% yield) of the desired stilbene 10 as a colorless oil. $^1$H NMR (CDCl$_3$) δ 7.55-7.35 (m, 6H), 7.04 (skewed d, J=16 Hz, 1H), 6.88 (skewed d, J=16 Hz, 1H), 6.68 (d, J=8.4 Hz, 2H), 5.50 (s, 1H), 4.29 (m, 2H), 4.12 (q, J=7.2 Hz, 2H), 4.03 (t, J=12 Hz, 2H), 3.38 (t, J=7.2 Hz, 2H), 2.96 (s, 3H), 2.34 (t, J=7.2 Hz, 2H), 2.25 (m, 1H), 1.92 (p, J=7.2 Hz, 2H), 1.44 (d, J=13 Hz, 1H), 1.25 (t, J=7.2 Hz, 3).

Example 10. Ethyl 4-[[4-[(E)-2-[4-(formyl)phenyl]ethenyl]phenyl]methylamino]butanoate (11)

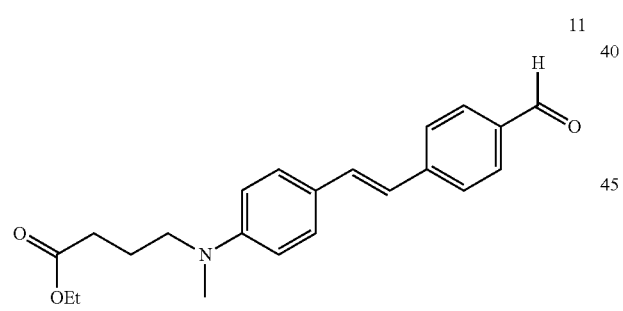

To a solution of 10 (0.5 g, 1.22 mmol) in 80 ml of acetone was added 4 ml of 10% hydrochloric acid. After being kept at room temperature for 3 h the reaction was neutralized by adding 3 ml of triethylamine and then concentrated. The resultant solid was re-suspended in water (approx. 50 ml) and collected by filtration. The solid was washed with water and dried in vacuo to afford 0.4 g (93% yield) of the desired aldehyde 11 as an orange solid. $^1$H NMR (CDCl$_3$) δ 9.96 (s, 1H), 7.83 (d, J=8.4 Hz, 2H), 7.60 (d, J=8.1 Hz, 2H), 7.43 (d, J=8.7 Hz, 2H), 7.20 (skewed d, J=16 Hz, 1H), 6.92 (d, J=16 Hz, 1H), 6.71 (d, J=9 Hz, 2H), 4.14 (q, J=7.2 Hz, 2H), 3.42 (t, J=7.2 Hz, 2H), 2.99 (s, 3H), 2.34 (t, J=7.2 Hz, 2H), 1.26 (t, J=6.9 Hz, 3H).

Example 11. Ethyl 4-[[4-[(E)-2-[4-[(E)-2-[4-nitrophenyl]ethenyl] phenyl] ethenyl] phenyl]methylamino]butanoate (12)

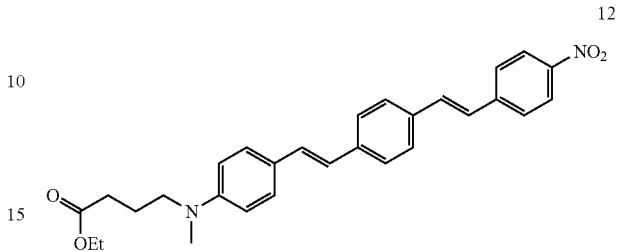

To a solution of aldehyde 11 (0.4 g, 1.13 mmol) and diethyl (4-nitrobenzyl)phosphonate (3a) (0.33 g, 1.2 mmol) in 10 mL of anhydrous THF was added a solution of sodium hydride (55 mg, 2.3 mmol) in 10 ml of anhydrous ethanol. After being agitated for 4 h the reaction was filtered and the collected solid was washed with methanol. Drying in vacuo afforded 0.497 g (93% yield) of the desired bis-stilbene 12 as a brown-red solid. $^1$H NMR (DMSO-d6) δ 8.23 (d, J=9H, 2H), 7.87 (d, J=9H, 2H), 7.7-7.3 (m, 8H), 7.21 (skewed d, J=16 Hz, 1H), 6.99 (skewed d, J=16 Hz, 1H), 6.72 (d, J=9 Hz, 2H), 4.06 (q, J=7.2 Hz, 2H), 2.92 (s, 3H), 3.4 (m, 2H), 2.35 (t, J=7.2 Hz, 2H), 1.78 (p, J=7.5 Hz, 2H), 1.18 (t, J=7.2 Hz, 3H).

Example 12. 4-[[4-[(E)-2-[4-[(E)-2-[4-nitrophenyl]ethenyl]phenyl]ethenyl]phenyl]methylamino]butanoic acid (13)

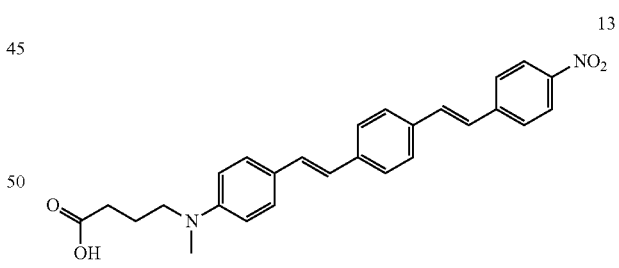

A suspension of bis-stilbene 12 (0.48 g, 1.02 mmol) in a mixture of THF (40 ml), MeOH (40 ml), water 5 ml and 50% NaOH (1 ml) was heated at 60° C. with stirring for 6 h. The reaction was cooled concentrated, re-suspended in water (50 ml) and neutralized with 1 N HCl to a pH of 4. The red-brown solid was collected by filtration and washed with water. Drying in vacuo afforded 0.43 g (95% yield) of the desired acid 13 as a brown solid. $^1$H NMR (DMSO-d6) δ 8.24 (d, J=9 Hz, 2H), 7.86 (d, J=9 Hz, 2H), 7.7-7.4 (m, 8H), 7.21 (skewed d, J=16 Hz, 1H), 6.99 (skewed d, J=16 Hz, 1H), 6.73 (d, J=9 Hz, 2H), 3.34 (m, 2H), 2.27 (m, 2H), 1.73 (p, J=8.1 Hz, 2H).

Example 13. Pentafluorophenyl 4-[[4-[(E)-2-[4-[(E)-2-[4-nitrophenyl]ethenyl]phenyl]ethenyl]phenyl]methylamino]butanoate (14)

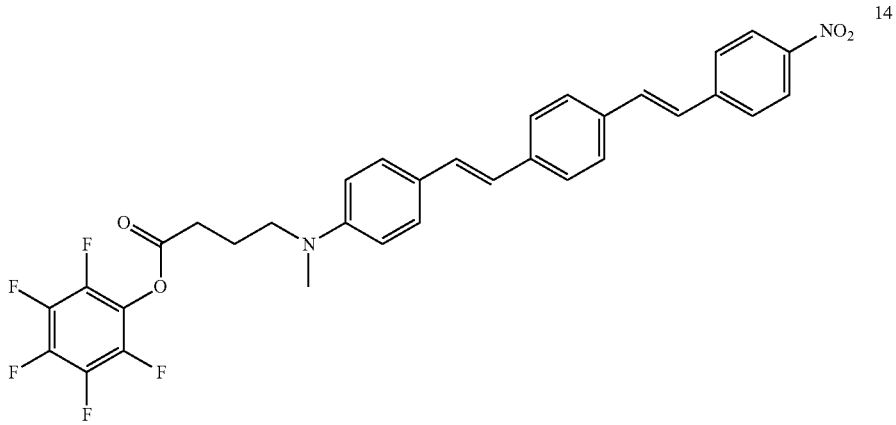 [SMILES: CN(CCCC(=O)Oc1c(F)c(F)c(F)c(F)c1F)c1ccc(/C=C/c2ccc(/C=C/c3ccc([N+](=O)[O-])cc3)cc2)cc1]

To a suspension of acid 13 (0.43 g, 0.97 mmol) in 20 ml DMF was added triethylamine (1.5 ml, 10.8 mmol) followed by PFP-TFA added over 5 h in four 0.25 ml (4×1.45 mmol) portions. The final suspension was concentrated and diluted with 10 ml of acetonitrile. The resultant red solid was collected by filtration, washed with ether and dried in vacuo to give 0.555 g (94% yield) of PFP ester 14. $^1$H NMR (CDCl$_3$) δ 8.22 (d, J=8.4 Hz, 2H), 7.63 (d, J=8.7 Hz, 2H), 7.51 (s, 4H), 7.43 (d, J=8.7 Hz, 2H), 7.27 (skewed d, J=16 Hz, 1H), 7.13 (skewed d, J=16 Hz, 1H), 7.11 (skewed d, J=16 Hz, 1H), 6.91 (skewed d, J=16 Hz, 1H), 6.72 (d, J=8.7 Hz, 2H), 3.49 (t, J=7 Hz, 2H), 3.08 (s, 3H), 2.74 (t, J=7 Hz, 2H), 2.08 (p, J=7 Hz, 2H).

Example 14. 1-[(2S,4R)-4-hydroxy-2-((bis(4-methoxyphenyl)(phenyl)methoxy)methyl)pyrrolidin-1-yl]-4-[[4-[(E)-2-[4-[(E)-2-[4-nitrophenyl]ethenyl]phenyl]ethenyl]phenyl]methylamino]butan-1-one (14)

(1) Preparation of 5-dimethoxytrityloxymethyl-3-hydroxypyrrolidine

A solution of N-Fmoc-5-dimethoxytrityloxymethyl-3-hydroxypyrrolidine (U.S. Pat. No. 6,184,389) (0.7 g, 1.09 mmol) in a mixture of DMF (10 ml) and TEA (10 ml) was heated at 80° C. for 1 h then concentrated to an oil and re-dissolved in DMF (25 ml) and TEA (0.5 ml). The solution of crude 5-dimethoxytrityloxymethyl-3-hydroxypyrrolidine was promptly used in the next step without additional purification.

(2) Coupling of PFP ester 13 with 5-dimethoxytrityloxymethyl-3-hydroxypyrrolidine The solution of crude 5-dimethoxytrityloxymethyl-3-hydroxypyrrolidine, prepared as described above, was added to a flask containing 0.55 g (0.90 mmol) of PFP ester 13. The flask was swirled for 2 h until a clear red solution was obtained. After being stirred at room temperature for a total of 3 h the reaction was concentrated, re-dissolved in CH$_2$Cl$_2$ (100-150 ml), washed with dilute NaHCO$_3$, then brine and dried over Na$_2$SO$_4$. The drying agent was removed by filtration and the filtrate concentrated. The resultant material was then chromatographed on silica eluting with CH$_2$Cl$_2$ followed by 5% MeOH in CH$_2$Cl$_2$. Concentration of the pure product fractions afforded 14 (0.7 g, 97% yield) as a red amorphous solid (mixture of amide rotamers (2:1) according to $^1$H NMR). $^1$H NMR (CDCl$_3$) δ 8.22 (d, J=8.7 Hz, 2H),

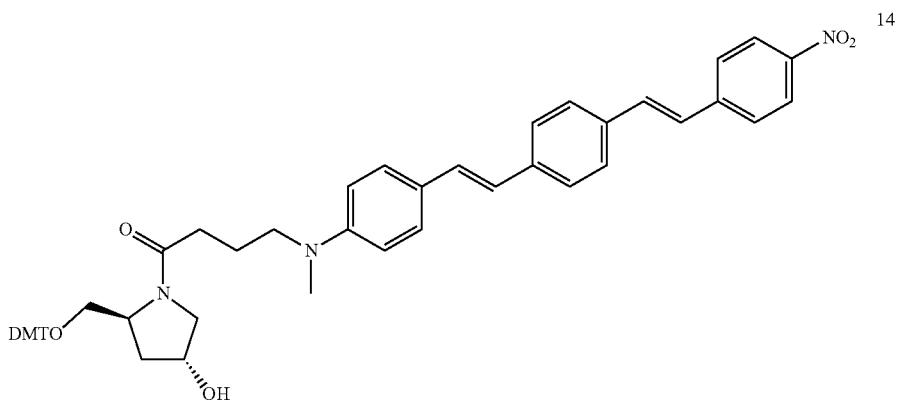

7.63 (d, J=8.7 Hz, 2H), 7.51 (s, 4H), 7.4-7.0 (m, 13H), 6.95-6.6 (m, 8H), 4.62 (m, ⅔H), 4.53 (m, ⅓H), 4.41 (m, ⅔H), 4.06 (m, ⅓H), 3.75 (mixture s, 6H), 3.9-3.6 (m, 1H), 3.6-3.05 (m, 5H), 2.97 (s, ⅔ 3H), 2.90 (s, ⅓ 3H), 2.4-1.7 (m, 6H).

Example 15. 1-[(2S,4R)-1-[4-[[4-[(E)-2-[4-[(E)-2-[4-nitrophenyl]ethenyl]phenyl]ethenyl]phenyl]methylamino]-1-oxobutyl]-2-((bis(4-methoxyphenyl)(phenyl)methoxy)methyl)pyrrolidin-4-yl]-, 2-cyanoethyl N,N-diisopropylphosphoramidoite (15)

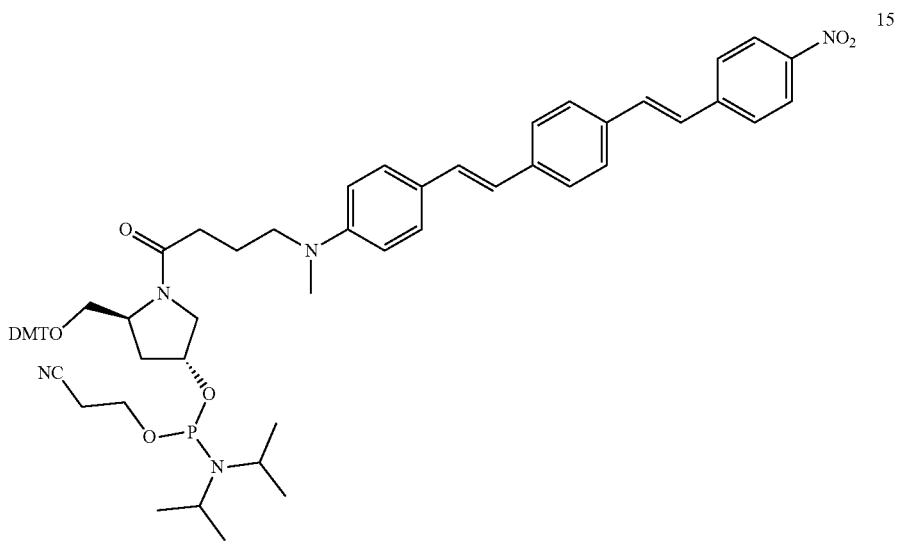

Disopropylaminium tetrazolide (0.9 mmol) was added to a partial solution of 14 (0.7 g, 0.875 mmol) in 20 ml of anhydrous CH$_2$Cl$_2$ followed by 2-cyanoethyl N,N,N'N'-tetraisopropylphosphordiamidite (0.33 g, 1.1 mmol). The reaction was agitated for 5 h then diluted with CH$_2$Cl$_2$ (100 ml) and washed saturated sodium bicarbonate (100 ml). The organic phase was washed with brine, dried over Na$_2$SO$_4$ and concentrated to approx. 10 ml. The obtained oil was diluted with 100 ml of hexane. The resultant solid was collected by filtration and washed with hexane. Drying in vacuo afforded 0.845 g (92% yield) of phosphoramidite 15 as an orange-brown amorphous solid (mixture of diastereomers (1:1) and amide rotamers (2:1) according to $^{31}$P NMR) $^{31}$P NMR (CDCl$_3$) δ 147.79, 147.61, 147.27, 146.85.

Example 16. 4-[(E)-2-(4-Nitrophenyl)ethenyl]benzoic acid, sodium salt (16)

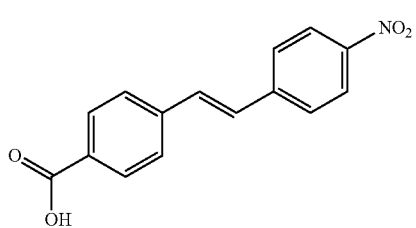

To a solution of sodium ethoxide (15 mmol) in 25 ml of anhydrous ethanol was added 0.75 g (5 mmol) of 4-carboxybenzaldehyde followed by 1.5 g (5.8 mmol) of diethyl (4-nitrobenzyl)phosphonate (3a). The reaction was stirred at 90° C. for 1 h then cooled and diluted with 20 ml of ethyl acetate. The resultant solid was collected by filtration, washed with ethyl acetate and dried. The obtained crude product was re-crystallized from hot water (10-15 ml) to afford 0.89 g (61% yield) of nitrostilbenecarboxylic acid (sodium salt) 16 as yellow crystals. $^1$H NMR (DMSO-d6) δ 8.23 (d, J=9 Hz, 2H), 7.87 (d, J=9 Hz, 2H), 7.86 (d, J=9 Hz, 2H), 7.56 (d, J=8.4 Hz, 2H), 7.54 (skewed d, J=16.5 Hz, 1H), 7.41 (skewed d, J=16.5 Hz, 1H).

Example 17. Pentafluorophenyl 4-[(E)-2-(4-nitrophenyl)ethenyl]benzoate (17)

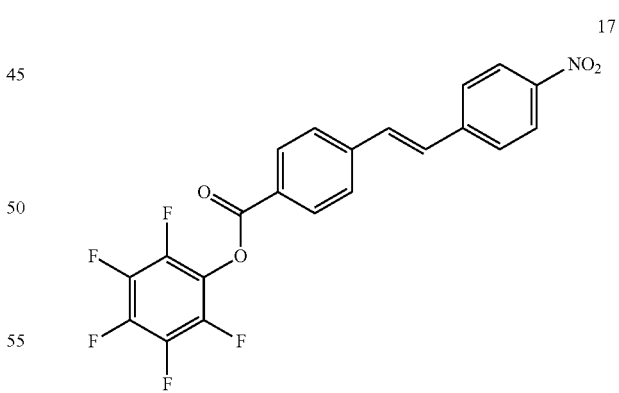

To a suspension of acid 16 (0.89 g, 3.2 mmol) in 30 ml of anhydrous DMF was added 1 ml of triethylamine followed by two portions (0.8 and 0.5 ml, total of 7.57 mmol) of PFP-TFA with a 30 min interval. The resultant clear reaction was checked by reverse phase for completeness and then concentrated. The obtained solid was partitioned between CH₂Cl₂ and 10% citric acid. The organic phase was washed with brine, dried over MgSO₄ and concentrated. The crude product was re-crystallized from 10% ethyl acetate/hexane to afford 1.1 g (79%) of PFP ester 17 as a light yellow solid. ¹H NMR (CDCl₃) δ 8.26 (d, J=9 Hz, 2H), 8.23 (d, J=8.4 Hz), 7.71 (d, J=8.7 Hz, 2H), 7.69 (d, J=9 Hz, 2H), 7.33 (s, 2H).

Example 18. ((2S,4R)-4-hydroxy-2-((bis(4-methoxyphenyl)(phenyl)methoxy)methyl)pyrrolidin-1-yl) (4-((E)-2-(4-nitrophenyl)ethenyl) phenyl) methanone (18)

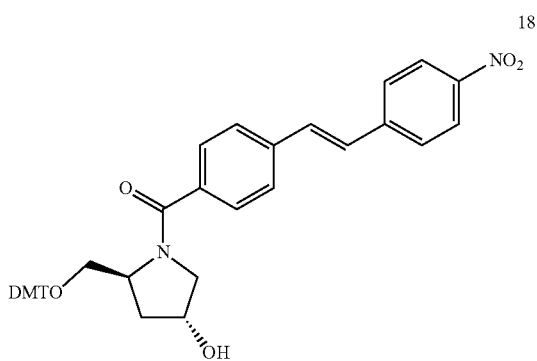

(1) Preparation of 5-dimethoxytrityloxymethyl-3-hydroxypyrrolidine

A solution of N-Fmoc-5-dimethoxytrityloxymethyl-3-hydroxypyrrolidine (1.2 g, 1.87 mmol) in a mixture of DMF (12 ml) and TEA (12 ml) was heated at 80° C. for 1 h then concentrated to an oil and re-dissolved in DMF (25 ml) and TEA (0.5 ml). The solution of crude 5-dimethoxytrityloxymethyl-3-hydroxypyrrolidine was promptly used in the next step without additional purification.

(2) Coupling of PFP ester 17 with 5-dimethoxytrityloxymethyl-3-hydroxypyrrolidine The solution of crude 5-dimethoxytrityloxymethyl-3-hydroxypyrrolidine prepared as described above, was added to a flask containing 0.70 g (1.61 mmol) of PFP ester 17. The flask was swirled until a clear solution was obtained. After being stirred at room temperature for a total of 3 h the reaction was concentrated, re-dissolved in ethyl acetate (100-150 ml), washed with dilute NaHCO₃, then brine and dried over Na₂SO₄. The drying agent was removed by filtration and the filtrate concentrated. The resultant material was then chromatographed on silica eluting with ethyl acetate followed by 10% acetone in ethyl acetate. Concentration of the pure product fractions afforded 18 (1.01 g, 93% yield) as a light yellow amorphous solid (mixture of amide rotamers (1:10) according to NMR data). ¹H NMR (DMSO-d6) δ 8.26 (d, J=8.7 Hz, 2H), 7.91 (d, J=9 Hz, 2H), 7.78 (skewed d, J=8.1 Hz, 2H), 7.58 (m, 4H), 7.40 (skewed d, J=7.5 Hz, 2H), 7.25 (m, 7.4H), 7.02 (m, 0.6H), 6.87 (m, 4H), 5.10 (m, 0.1H), 4.88 (d, J=2.7 Hz, 9/10H), 4.46 (m, 1H), 4.35 (m, 0.1H), 4.23 (m, 1H), 3.75 (m, 1.5H), 3.73 (s, 3H), 3.72 (s, 3H), 3.55 (m, 0.2H), 3.36 (m, 1H), 3.11 (m, 1H), 2.70 (m, 0.1H), 2.55 (m, 0.1H), 2.11 (m, 1H), 2.08 (m, 1H).

Example 19. ((2S,4R)-1-((4-((E)-2-(4-nitrophenyl)ethenyl) phenyl)oxomethyl)-2-((bis(4-methoxyphenyl)(phenyl)methoxy)methyl)pyrrolidin-4-yl),-2-cyanoethyl N,N-diisopropylphosphoramidoite (19)

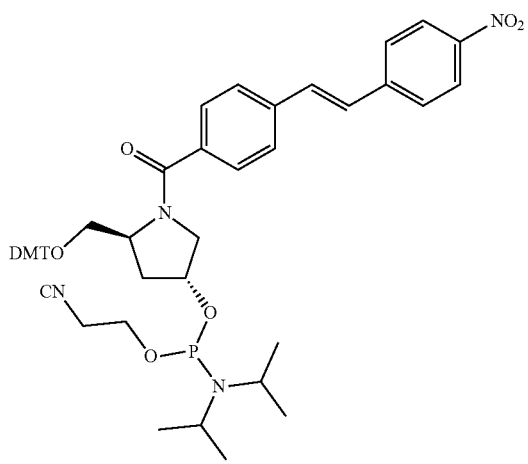

Diisopropylaminium tetrazolide (1.6 mmol) was added to a solution of 18 (1.1 g, 1.63 mmol) in 30 ml of anhydrous CH₂Cl₂ followed by 2-cyanoethyl N,N,N'N'-tetraisopropylphosphordiamidite (0.62 g, 2.06 mmol). The reaction was agitated for 10 h then concentrated and partitioned between ethyl acetate (100 ml) and saturated sodium bicarbonate (100 ml). The organic phase was washed with brine, dried over Na₂SO₄ and concentrated. The obtained oil was re-dissolved in approx. 10 ml of ethyl acetate and precipitated by adding 200 ml of hexane. After allowing the oil to settle for 10-15 min the liquid was decanted and the residual material re-dissolved in a small amount (3-5 ml) of anhydrous CH₂Cl₂. Drying in vacuo afforded phosphoramidite 19 (1.3 g, 92% yield) as a yellow amorphous solid (mixture of diastereomers (1:1) and amide rotamers (1:10)) ³¹P NMR (DMSO-d6) δ 146.13, 145.76.

Example 20. Methyl 4-{6-[(E)-2-(4-nitrophenyl)ethenyl]pyridin-2-yl}benzoate (20)

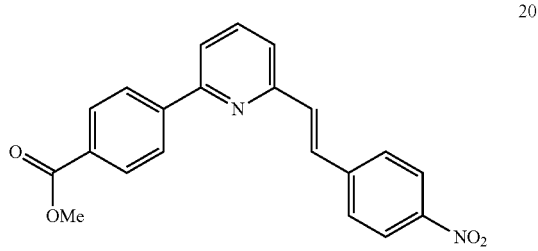 [SMILES: COC(=O)c1ccc(-c2cccc(/C=C/c3ccc([N+](=O)[O-])cc3)n2)cc1]

A solution of sodium ethoxide (7.3 mmol) in 15 ml of anhydrous ethanol was added to a mixture methyl 4-(6-formylpyridin-2-yl)benzoate (0.905 g, 3.75 mmol) and diethyl (4-nitrobenzyl)phosphonate (3a) (1.1 g, 4 mmol). The reaction was stirred at room temperature for 1 h and then diluted with 20 ml of water. The resultant solid was collected by filtration and washed with water. Drying in vacuo afford 1.3 g of stilbene 20 (mixture of methyl and ethyl esters) as a light yellow solid. ¹H NMR (CDCl₃) δ 8.25 (d, J=9 Hz, 2H), 8.18 (s, 4H), 7.9-7.7 (m, 5H), 7.45-7.35 (m, 2H), 4.42 (q, J=7.2 Hz, 1H), 3.97 (s, 1.5H), 1.44 (t, J=7.2 Hz, 1.5H).

Example 21. 4-{6-[(E)-2-(4-Nitrophenyl)ethenyl]pyridin-2-yl}benzoic acid (21)

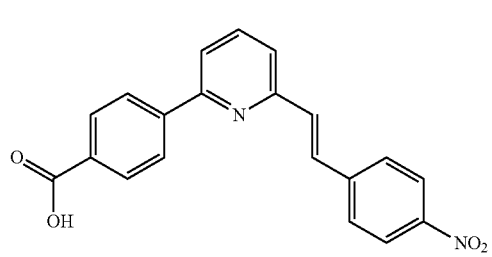

To a solution of 20 (1.3 g, 3.6 mmol) in 30 ml of THF was added 20 ml of MeOH followed by 10 ml of 1N NaOH. After being stirred at 50° C. for 3 h the reaction was cooled, neutralized with 1N HCl to a pH of 2-3, then concentrated and diluted with water (approx. 30 ml). The obtained solid was collected by filtration and washed with water. Drying in vacuo afforded 1.25 g (100%) of acid 21 as a light yellow solid. ¹H NMR (DMSO-d6) δ 13.11 (s, 1H), 8.34 (d, J=8.4 Hz, 2H), 8.27 (d, J=9 Hz, 2H), 8.08 (d, J=8.4 Hz, 2H), 8.05-7.90 (m, 5H), 7.67 (d, J=16 Hz, 1H), 7.66 (dd, J₁=6.6 Hz, J₂=2.1 Hz, 1H).

Example 22. Pentafluorophenyl 4-{6-[(E)-2-(4-nitrophenyl)ethenyl]pyridin-2-yl}benzoate (22)

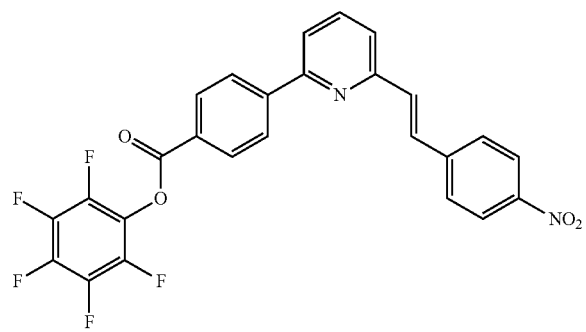

Pentafluorophenyl trifluoroacetate was added in two portions (0.5 and 0.4 ml, total of 5.2 mmol) with a 1 h interval to a solution of acid 21 (1.25 g, 3.6 mmol) and triethylamine (1 ml, 7.3 mmol). After being stirred for a total of 3 h the reaction was concentrated and the resulting solid re-suspended in 10 ml of ethyl acetate. The solid was collected by filtration and washed with small amount of ethyl acetate (approx. 5 ml) and 20% ethyl acetate/hexane (approx. 20 ml). Drying in vacuo afforded 1.28 g (69%) of PFP ester 22 as an off-white solid. ¹H NMR (CDCl₃) δ 8.4-8.2 (m, 6H), 7.92-7.82 (m, 2H), 7.80-7.70 (m, 3H), 7.45 (d, J=7.5 Hz, 1H), 7.39 (skewed d, J=16 Hz, 1H).

Example 23. ((2S,4R)-4-hydroxy-2-((bis(4-methoxyphenyl)(phenyl)methoxy)methyl)pyrrolidin-1-yl) (4-{6-[(E)-2-(4-nitrophenyl)ethenyl]pyridin-2-yl}phenyl)methanone (23)

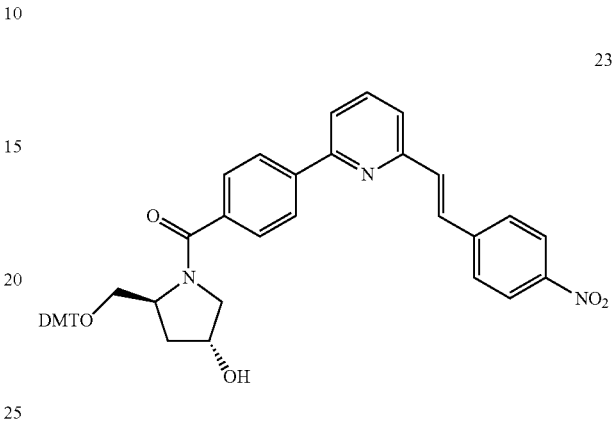

(1) Preparation of 5-dimethoxytrityloxymethyl-3-hydroxypyrrolidine

A solution of N-Fmoc-5-dimethoxytrityloxymethyl-3-hydroxypyrrolidine (1.2 g, 1.87 mmol) in a mixture of DMF (12 ml) and TEA (12 ml) was heated at 80° C. for 1 h then concentrated to an oil and re-dissolved in DMF (25 ml) and TEA (0.5 ml). The solution of crude 5-dimethoxytrityloxymethyl-3-hydroxypyrrolidine was promptly used in the next step without additional purification.

(2) Coupling of PFP ester 22 with 5-dimethoxytrityloxymethyl-3-hydroxypyrrolidine The solution of crude 5-dimethoxytrityloxymethyl-3-hydroxypyrrolidine prepared as described above, was added to a flask containing 0.82 g (1.61 mmol) of PFP ester 22. The flask was swirled until a clear solution was obtained. After being stirred at room temperature for a total of 3 h the reaction was concentrated, re-dissolved in ethyl acetate (100-150 ml), washed with dilute NaHCO₃, then brine and dried over Na₂SO₄. The drying agent was removed by filtration and the filtrate concentrated. The resultant material was then chromatographed on silica eluting with ethyl acetate followed by 10% acetone in ethyl acetate. Concentration of the pure product fractions afforded 23 (1.2 g, 100% yield) as a light yellow amorphous solid (mixture of amide rotamers (1:10) according to NMR data). ¹H NMR (DMSO-d6) δ 8.32 (d, J=8.1 Hz, 2H), 8.28 (d, J=9 Hz, 2H), 8.17 (m, 0.3H), 8.05-7.9 (m, 5H), 7.75-7.6 (m, 4H), 7.40 (m, 2H), 7.26 (m, 7H), 7.02 (m, 0.6H), 6.88 (m, 4H), 5.13 (m, 0.1H), 4.90 (d, J=2.7 Hz, ⁹⁄₁₀H), 4.49 (m, 1H), 4.38 (m, 0.1H), 4.31 (m, 1H), 3.75 (m, 1.3H), 3.73 (s, 3H), 3.72 (s, 3H), 3.41 (m, 2H), 3.11 (m, 1H), 2.75 (m, 0.1H), 2.55 (m, 0.1H), 2.13 (m, 1H), 2.03 (m, 1H).

Example 24. ((2S,4R)-1-((4-{6-[(E)-2-(4-nitrophenyl)ethenyl]pyridin-2-yl}phenyl)oxomethyl)-2-((bis(4-methoxyphenyl)(phenyl)methoxy)methyl)pyrrolidin-4-yl)-, 2-cyanoethyl N,N-diisopropylphosphoramidoite (24)

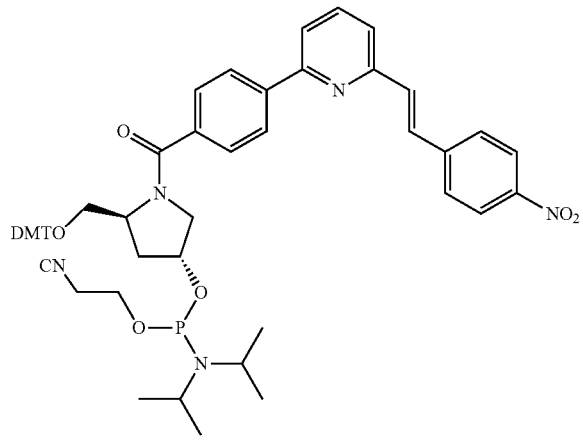

24

Diisopropylaminium tetrazolide (1.6 mmol) was added to a solution of 23 (1.2 g, 1.60 mmol) in 30 ml of anhydrous $CH_2Cl_2$ followed by 2-cyanoethyl N,N,N'N'-tetraisopropylphosphordiamidite (0.62 g, 2.06 mmol). The reaction was agitated for 10 h then concentrated and partitioned between ethyl acetate (100 ml) and saturated sodium bicarbonate (100 ml). The organic phase was washed with brine, dried over $Na_2SO_4$ and concentrated. The obtained oil was re-dissolved in approx. 10 ml of ethyl acetate and precipitated by adding 200 ml of hexane. After allowing the oil to settle for 10-15 min the liquid was decanted and the residual material re-dissolved in a small amount (3-5 ml) of anhydrous $CH_2Cl_2$. Drying in vacuo afforded phosphoramidite 24 (1.38 g, 91% yield) as a light yellow amorphous solid (mixture of diastereomers (1:1) and amide rotamers (1:10)) $^{31}$P NMR (DMSO-d6) δ 146.08, 145.77.

Example 25. Methyl 4'-[(E)-2-(2,4-dinitrophenyl)ethenyl]biphenyl-4-carboxylate (25)

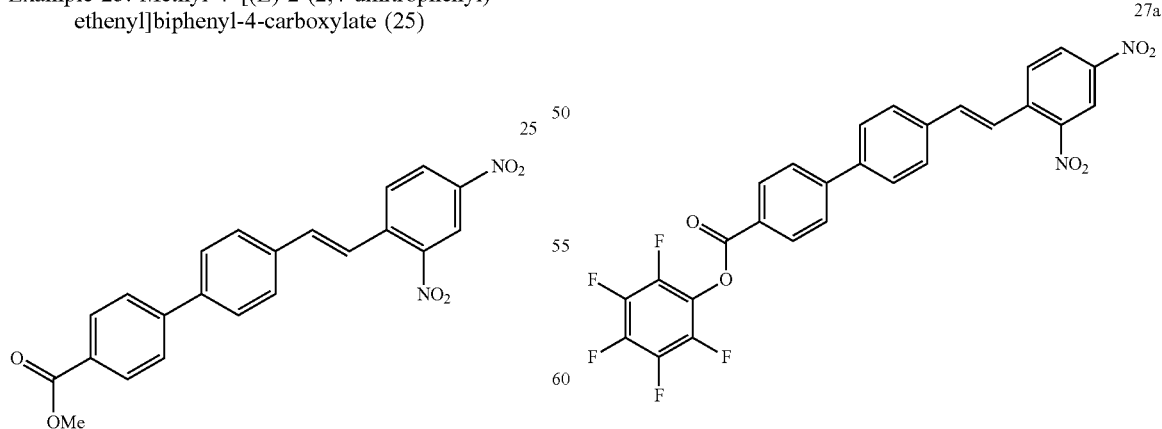

25

A mixture of methyl 4-(4-formylphenyl)benzoate (1.0 g, 4.1 mmol), 2,4-dinitrotoluene, (0.9 g, 5 mmol), piperidine (0.2 ml, 2 mmol) and pyridine (3 ml) was heated at 80° C. with stirring for 8 h. The reaction was cooled and re-suspended in approx. 100 ml of 10% citric acid. The resultant brown solid was collected by filtration, washed with water and dried. The crude material was re-suspended in hot ethyl acetate and filtered. The collected solid was washed with ethyl acetate. Drying in vacuo afforded 0.97 g (58% yield) of stilbene 25 as a bright yellow solid. $^1$H NMR (CDCl$_3$) δ 8.84 (d, J=2.4 Hz, 1H), 8.44 (dd, J1=8.7 Hz, J2=2.4 Hz, 1H), 8.12 (d, J=8.4 Hz, 2H), 8.01 (d, J=8.7 Hz, 1H), 7.68 (m, 7H), 7.32 (d, J=16 Hz, 1H), 3.59 (s, 3H).

Example 26. 4'-[(E)-2-(2,4-Dinitrophenyl)ethenyl]biphenyl-4-carboxylic acid (26a)

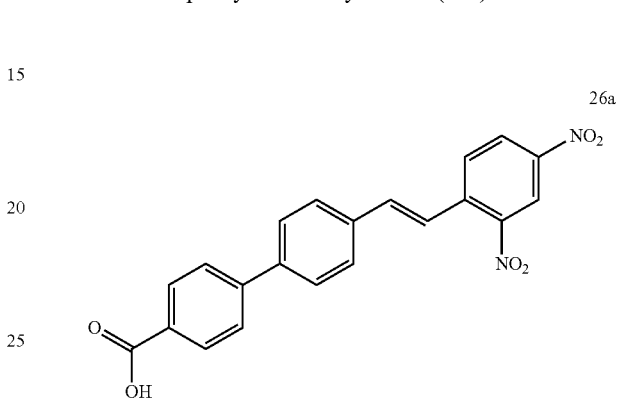

26a

To a solution of ester 25 (0.95 g, 2.35 mmol) in 60 ml of THF was added 40 ml of methanol and 20 ml of 1N NaOH. The reaction was kept at room temperature for 15 h until no starting material was found by reverse phase HPLC analysis and then neutralized by adding 20 ml of 1N HCl. The yellow solid was collected by filtration, washed with water and dried in vacuo to give 0.72 g (78%) of acid 26a. $^1$H NMR (DMSO-d6) δ 13.02 (s, 1H), 8.76 (d, J=2.4 Hz, 1H), 8.52 (dd, J$_1$=9 Hz, J$_2$=2.4 Hz, 1H), 8.28 (d, J=9 hz, 1H), 8.03 (skewed d, J=8.1 Hz, 2H), 7.95-7.75 (m, 6H), 7.67 (skewed d, J=16 Hz, 1H), 7.59 (skewed d, J=16 Hz, 1H).

Example 27. Pentafluorophenyl 4'-[(E)-2-(2,4-dinitrophenyl)ethenyl]biphenyl-4-carboxylate (27a)

27a

To a suspension of acid 26a (0.71 g, 1.181 mmol) in 25 ml of anhydrous $CH_2Cl_2$ was added 0.9 ml of triethylamine followed by 0.5 ml (2.91 mmol) of pentafluorophenyl trifluoroacetate. The reaction was stirred at room temperature for 5 h, then concentrated and re-suspended in a small amount (approx. 5-10 ml) of 50% ethyl acetate in hexane, The yellow solid was collected by filtration washed with 20% ethyl acetate in hexane and dried to afford 0.94 g (93% yield) of PFP ester 27a. $^1$H NMR (DMSO-d6) δ 8.77 (d, J=2.4 Hz, 1H), 8.55 (dd, J$_1$=9 Hz, J$_2$=2.4 Hz, 1H), 8.29 (m, 3H), 8.04 (skewed d, J=8.4 Hz, 2H), 7.92 (skewed d, J=8.1 Hz, 2H), 7.85 (skewed d, J=8.1 Hz, 2H), 7.70 (skewed d, J=16 Hz, 1H), 7.63 (skewed d, J=16 Hz, 1H).

Example 28. ((2S,4R)-4-hydroxy-2-((bis(4-methoxyphenyl)(phenyl)methoxy)methyl)pyrrolidin-1-yl) (4-{4-[(E)-2-(2,4-dinitrophenyl)ethenyl]phenyl}phenyl)methanone (28a)

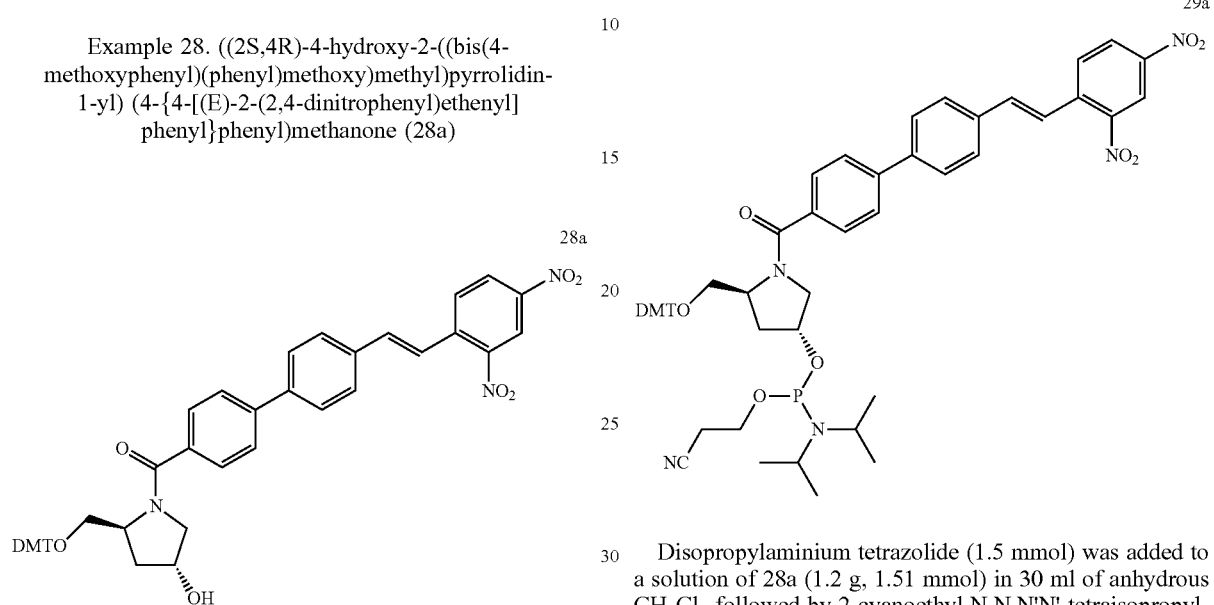

(1) Preparation of 5-dimethoxytrityloxymethyl-3-hydroxypyrrolidine

A solution of N-Fmoc-5-dimethoxytrityloxymethyl-3-hydroxypyrrolidine (1.2 g, 1.88 mmol) in a mixture of DMF (12 ml) and TEA (12 ml) was heated at 80° C. for 1 h then concentrated to an oil and re-dissolved in DMF (25 ml) and TEA (0.5 ml). The solution of crude 5-dimethoxytrityloxymethyl-3-hydroxypyrrolidine was promptly used in the next step without additional purification.

(2) Coupling of PFP ester 27a with 5-dimethoxytrityloxymethyl-3-hydroxypyrrolidine The solution of crude 5-dimethoxytrityloxymethyl-3-hydroxypyrrolidine prepared as described above, was added to a flask containing 0.90 g (1.61 mmol) of PFP ester 27a. The flask was swirled until a clear solution was obtained. After being stirred at room temperature for a total of 5 h the reaction was concentrated, re-dissolved in ethyl acetate (100-150 ml), washed with dilute NaHCO$_3$, then brine and dried over Na$_2$SO$_4$. The drying agent was removed by filtration and the filtrate concentrated. The resultant material was then chromatographed on silica eluting with ethyl acetate followed by 10% acetone in ethyl acetate. Concentration of the pure product fractions afforded 28a (1.27 g, 99% yield) as a light yellow solid (mixture of amide rotamers (1:10) according to NMR data). $^1$H NMR (DMSO-d6) δ 8.77 (d, J=2.4 Hz, 1H), 8.52 (dd, J$_1$=9 Hz, J$_2$=2.4 Hz, 1H), 8.29 (d, J=9 Hz, 1H), 7.8 (m, 6H), 7.65 (m, 4H), 7.45-7.0 (m, 10H), 6.87 (m, 4H), 5.10 (m, 0.1H), 4.89 (d, J=2.4 Hz, 9/10H), 4.49 (m, 1H), 4.38 (m, 0.1H), 4.30 (m, 1H), 3.75 (m, 1.3H), 3.73 (s, 3H), 3.72 (s, 3H), 3.39 (m, 2H), 3.10 (m, 1H), 2.75 (m, 0.1H), 2.55 (m, 0.1H), 2.13 (m, 1H), 2.03 (m, 1H).

Example 29. ((2S,4R)-1-((4-{4-[(E)-2-(2,4-dinitrophenyl)ethenyl]phenyl}phenyl)oxomethyl)-2-((bis(4-methoxyphenyl)(phenyl)methoxy)methyl)pyrrolidin-4-yl),-2-cyanoethyl N,N-diisopropylphosphoramidoite (29a)

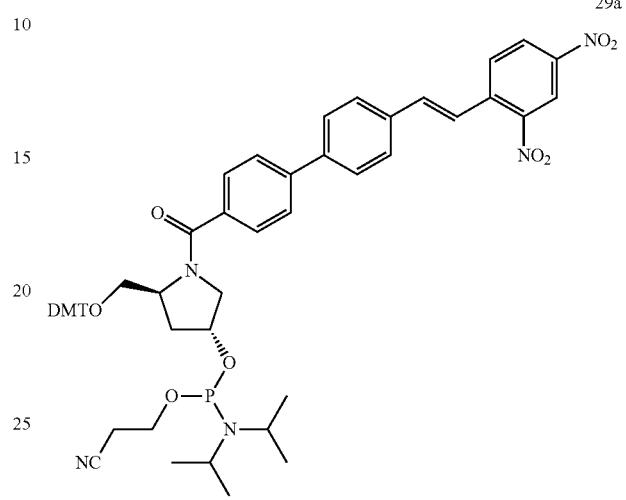

Disopropylaminium tetrazolide (1.5 mmol) was added to a solution of 28a (1.2 g, 1.51 mmol) in 30 ml of anhydrous CH$_2$Cl$_2$ followed by 2-cyanoethyl N,N,N'N'-tetraisopropylphosphordiamidite (0.58 g, 1.91 mmol). The reaction was agitated for 15 h then concentrated and partitioned between ethyl acetate (100 ml) and saturated sodium bicarbonate (100 ml). The organic phase was washed with brine, dried over Na$_2$SO$_4$ and concentrated. The obtained oil was re-dissolved in approx. 10 ml of ethyl acetate and precipitated by adding 200 ml of hexane. After allowing the oil to settle for 10-15 min the liquid was decanted and the residual material re-dissolved in a small amount (3-5 ml) of anhydrous CH$_2$Cl$_2$. Drying in vacuo afforded phosphoramidite 29a (1.5 g, 100% yield) as a light yellow amorphous solid (mixture of diastereomers (1:1) and amide rotamers (1:10)) $^{31}$P NMR (DMSO-d6) δ 146.08, 145.81.

Example 30. (2E)-3-{4-[(E)-2-(2,4-Dinitrophenyl)ethenyl]phenyl}prop-2-enoic acid (26b)

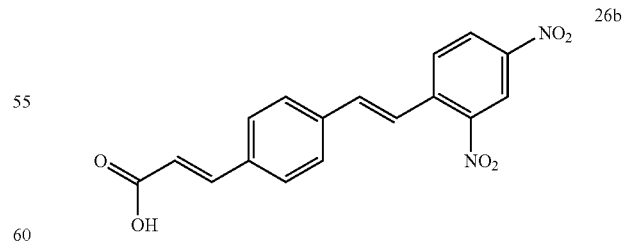

A mixture of 4-formylcinnamic acid (1.76 g, 10 mmol), 2,4-dinitrotoluene (2.18 g, 12 mmol), piperidine (1 ml, 10 mmol) and pyridine (10 ml) was heated at 80° C. with stirring for 6 h. The resultant brown oil was concentrated and re-suspended in 10% citric acid (approx. 100 ml). The brown solid was collected by filtration, washed with water and dried in vacuo to give 4.0 g of crude product, which was then purified by refluxing with approx. 100 ml of ethanol, cooling and filtration. Drying in vacuo afforded 2.4 g (70.5% yield) of sufficiently pure 26b as a brown solid. $^1$H NMR (DMSO-d6) δ 8.75 (d, J=2.4 Hz, 2H), 8.51 (dd, $J_1$=9 Hz, $J_2$=2.4 Hz, 2H), 8.25 (d, J=9 Hz, 2H), 7.73 (m, 4H), 7.60 (s, 2H), 7.58 (d, J=16 Hz, 1H), 6.60 (d, J=16 Hz, 1H).

Example 31. Pentafluorophenyl (2E)-3-{4-[(E)-2-(2,4-dinitrophenyl)ethenyl]phenyl}prop-2-enoate (27b)

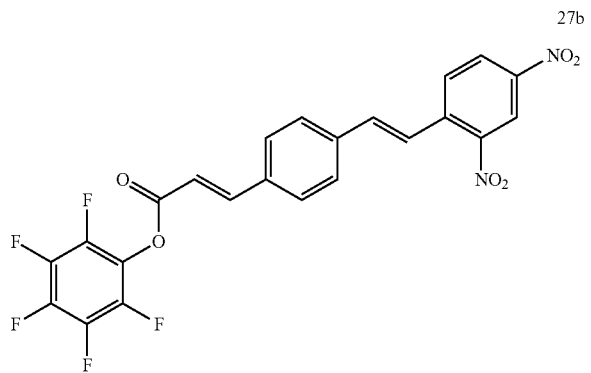 [SMILES: O=C(/C=C/c1ccc(/C=C/c2ccc([N+](=O)[O-])cc2[N+](=O)[O-])cc1)Oc1c(F)c(F)c(F)c(F)c1F]

27b

To a suspension of acid 26b (2.35 g, 6.9 mmol) in 92 ml of anhydrous $CH_2Cl_2$ was added 3.3 ml (24 mmol) followed by 1.5 ml (8.73 mmol) of pentafluorophenyl trifluoroacetate. The reaction was stirred at room temperature for 3 h until no starting material was found by reverse phase HPLC analysis. The reaction was concentrated and re-suspended in approx. 10 ml of 50% ethyl acetate in hexane. The yellow solid was collected by filtration, washed with 20% ethyl acetate in hexane and dried to afford 2.65 g (76% yield) of PFP ester 27b. $^1$H NMR (CDCl$_3$) δ 8.85 (d, J=2.1 Hz, 2H), 8.46 (dd, $J_1$=8.7 Hz, $J_2$=2.1 Hz, 2H), 7.99 (d, J=8.7 Hz, 2H), 7.95 (d, J=16.2 Hz, 1H), 7.73 (d, J=16 Hz, 1H), 7.66 (s, 4H), 7.28 (d, J=16 Hz, 1H), 6.70 (d, J=16.2 Hz, 1H).

Example 32. ((2S,4R)-4-hydroxy-2-((bis(4-methoxyphenyl)(phenyl)methoxy)methyl)pyrrolidin-1-yl) ((E)-2-{4-[(E)-2-(2,4-dinitrophenyl)ethenyl]phenyl}ethynyl)methanone (28b)

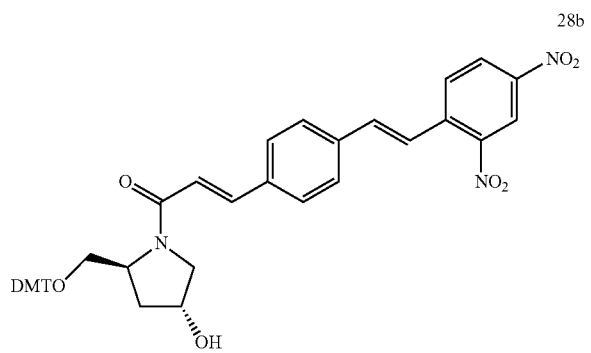

28b (1) Preparation of 5-dimethoxytrityloxymethyl-3-hydroxypyrrolidine

A solution of N-Fmoc-5-dimethoxytrityloxymethyl-3-hydroxypyrrolidine (1.1 g, 1.71 mmol) in a mixture of DMF (11 ml) and TEA (11 ml) was heated at 80° C. for 1 h then concentrated to an oil and re-dissolved in DMF (25 ml) and TEA (0.5 ml). The solution of crude 5-dimethoxytrityloxymethyl-3-hydroxypyrrolidine was promptly used in the next step without additional purification.

(2) Coupling of PFP ester 27b with 5-dimethoxytrityloxymethyl-3-hydroxypyrrolidine.

The solution of crude 5-dimethoxytrityloxymethyl-3-hydroxypyrrolidine prepared as described above, was added to a flask containing 0.74 g (1.47 mmol) of PFP ester 27b. The flask was swirled until a clear solution was obtained. After being stirred at room temperature for a total of 5 h the reaction was concentrated, re-dissolved in ethyl acetate (100-150 ml), washed with dilute $NaHCO_3$, then brine and dried over $Na_2SO_4$. The drying agent was removed by filtration and the filtrate concentrated. The resultant material was then chromatographed on silica eluting with ethyl acetate followed by 10% acetone in ethyl acetate. Concentration of the pure product fractions afforded 28b (1.07 g, 98% yield) as a yellow solid (mixture of amide rotamers (1:1) according to NMR data). $^1$H NMR (DMSO-d6) δ 8.76 (apparent t, J=2.1 Hz, 1H), 8.52 (apparent dt, $J_1$=9 Hz, $J_2$=2.1 Hz, 1H), 8.28 (apparent dd, $J_1$=9 Hz, $J_2$=2.1 Hz, 1H), 7.82 (skewed d, J=8.4 Hz, 1H), 7.73 (m, 3H), 7.62 (m, 2H), 7.55-7.45 (m, 1H), 7.35-7.05 (m, 10H), 6.86 (m, 2H), 6.76 (m, 2H), 5.05 (d, J=3.9 Hz, 0.5H), 4.98 (d, J=4.2 Hz, 0.5H), 4.71 (m, 0.5H), 4.67 (m, 0.5), 4.30 (m, 1H), 3.82 (m, 0.5H), 3.72 (s, 3H), 3.70 (s, 3H), 3.66 (s, 3H), 3.65 (s, 3H), 3.75-3.60 (m, 1.5H), 3.4-3.2 (m, 1H), 3.15-2.9 (m, 1.5H), 2.10 (m, 0.5H), 1.98 (m, 1.5H).

Example 33. ((2S,4R)-1-(((E)-2-{4-[(E)-2-(2,4-dinitrophenyl)ethenyl]phenyl}ethynyl)oxomethyl)-2-((bis(4-methoxyphenyl)(phenyl)methoxy)methyl)pyrrolidin-4-yl),-2-cyanoethyl N,N-diisopropylphosphoramidoite (29b)

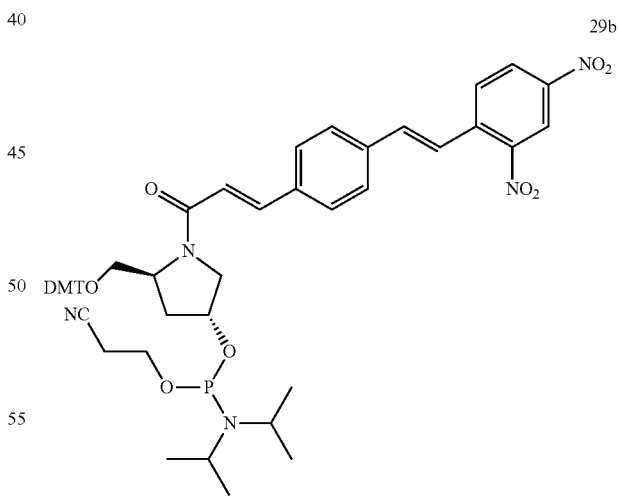

29b

Disopropylaminium tetrazolide (1.4 mmol) was added to a solution of 28b (1.05 g, 1.41 mmol) in 28 ml of anhydrous $CH_2Cl_2$ followed by 2-cyanoethyl N,N,N'N'-tetraisopropylphosphordiamidite (0.54 g, 1.77 mmol). The reaction was agitated for 15 h then concentrated and partitioned between ethyl acetate (100 ml) and saturated sodium bicarbonate (100 ml). The organic phase was washed with brine, dried over $Na_2SO_4$ and concentrated. The obtained oil was re-dissolved in approx. 10 ml of ethyl acetate and precipitated by adding 200 ml of hexane. After allowing the oil to settle for 10-15 min the liquid was decanted and the residual material re-dissolved in a small amount (3-5 ml) of anhydrous $CH_2Cl_2$. Drying in vacuo afforded phosphoramidite 29b (1.3 g, 98% yield) as a yellow amorphous solid (mixture of diastereomers (1:1) and amide rotamers (1:1)) $^{31}P$ NMR (DMSO-d6) δ 146.62, 146.46, 146.26, 145.88.

Example 34: Absorption Spectra of Exemplary Z98-Z112 Quenchers

Figure 5:
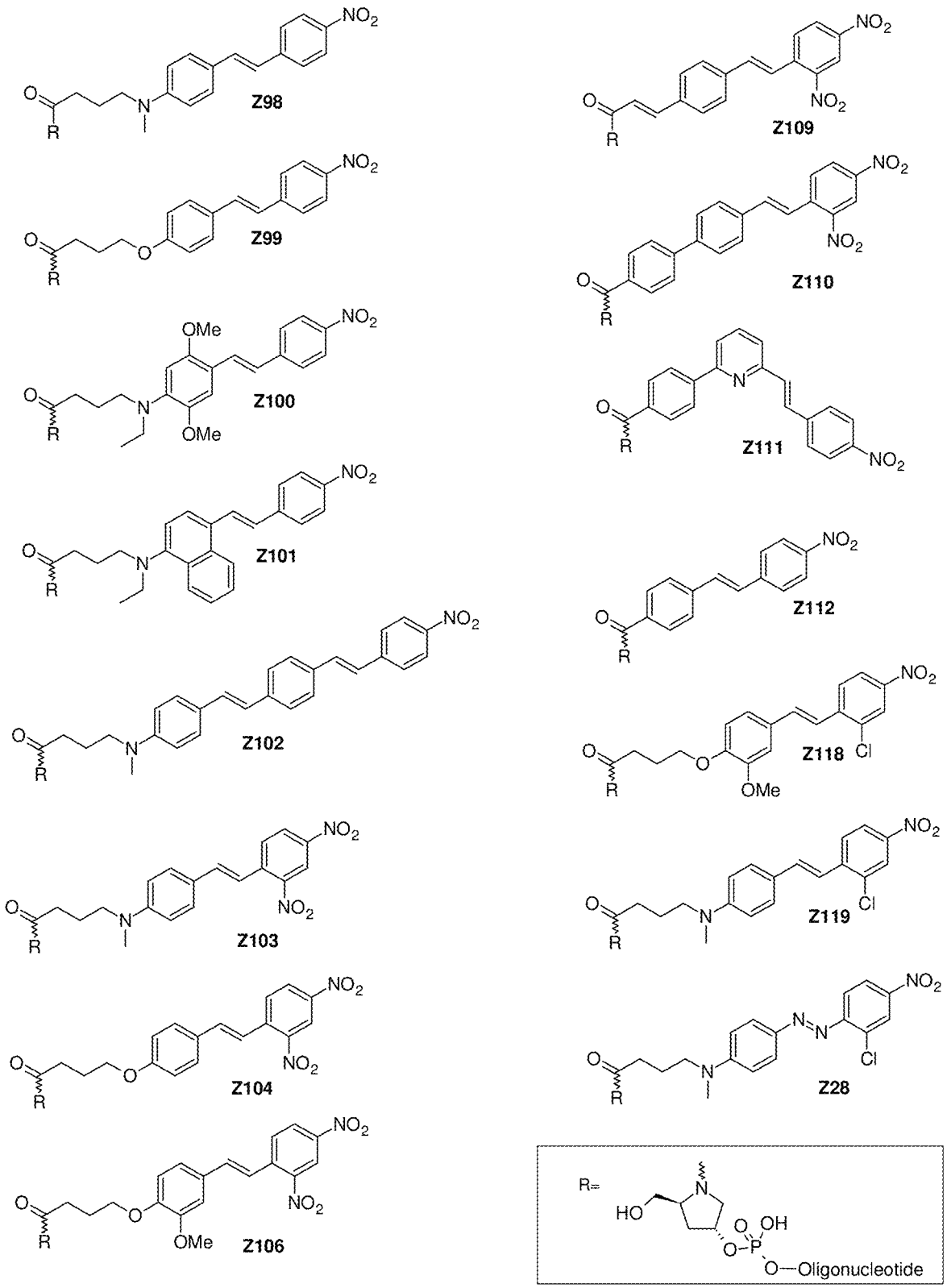
FIG. 5 shows examples of nitrodiarylethene quenchers in accordance with preferred embodiments disclosed herein.
Figure 6A:
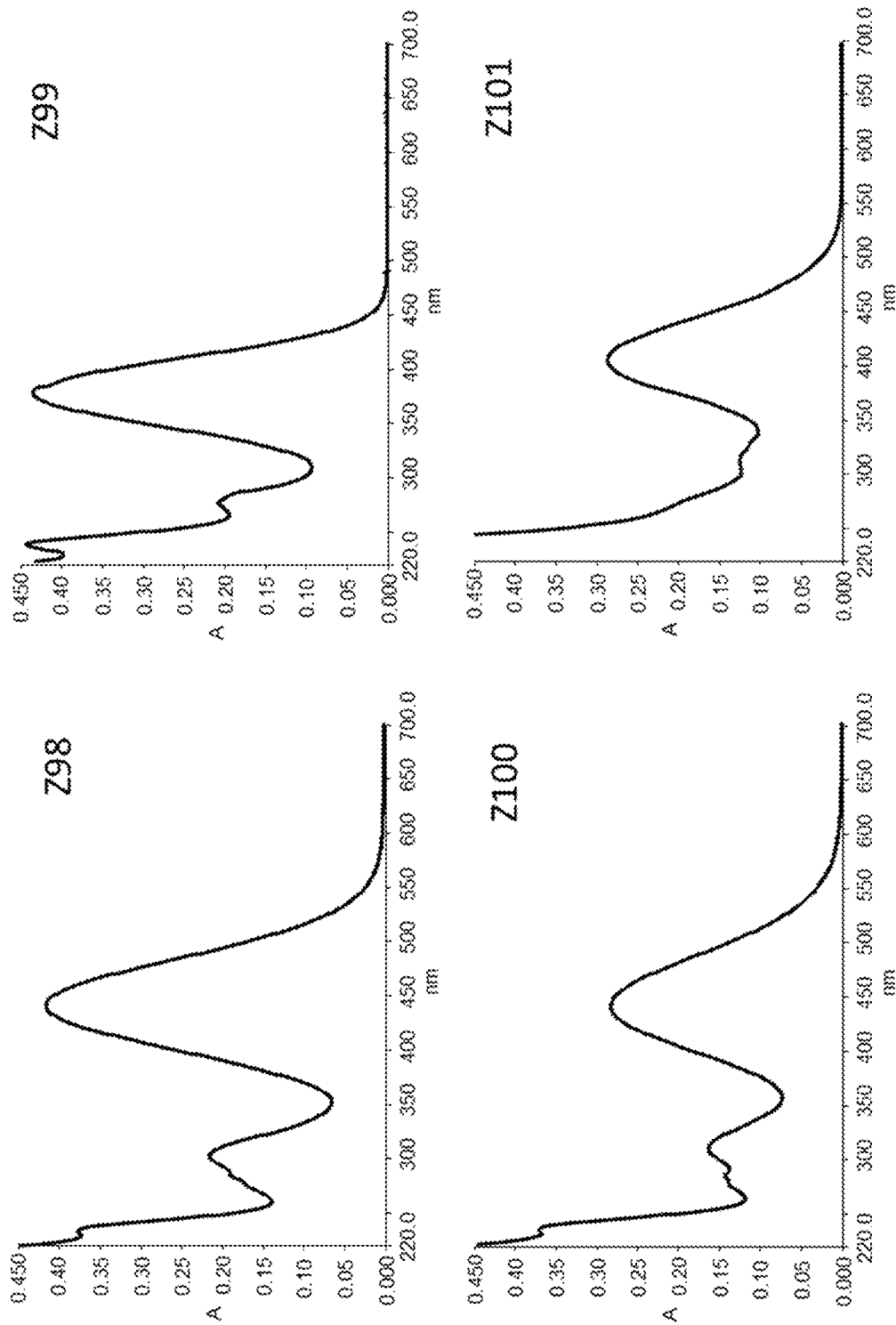
FIG. 6A shows absorption spectra in methanol of selected quenchers in accordance with preferred embodiments disclosed herein.
Figure 6B:
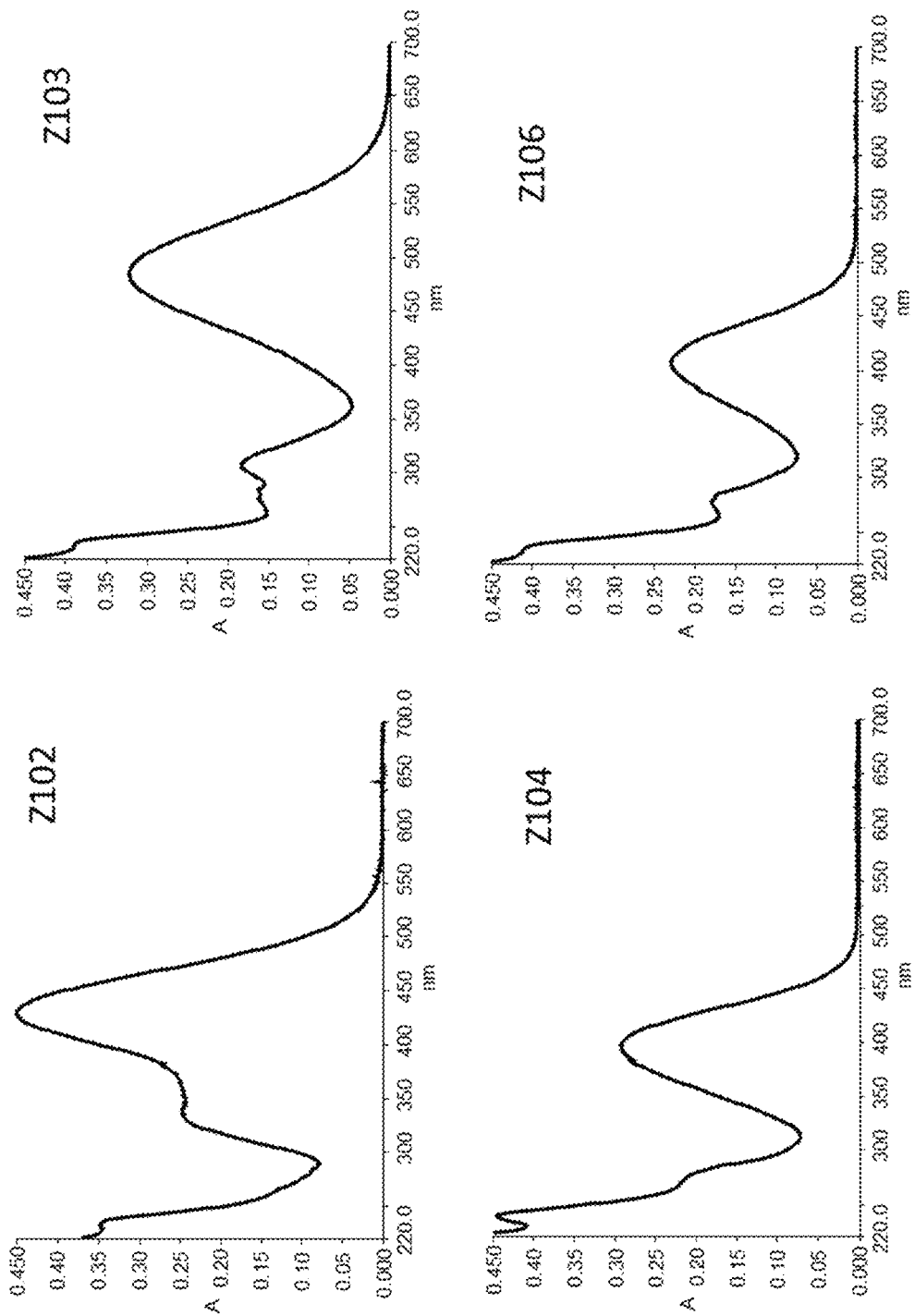
FIG. 6B shows absorption spectra in methanol of selected quenchers in accordance with preferred embodiments disclosed herein
Figure 6C:
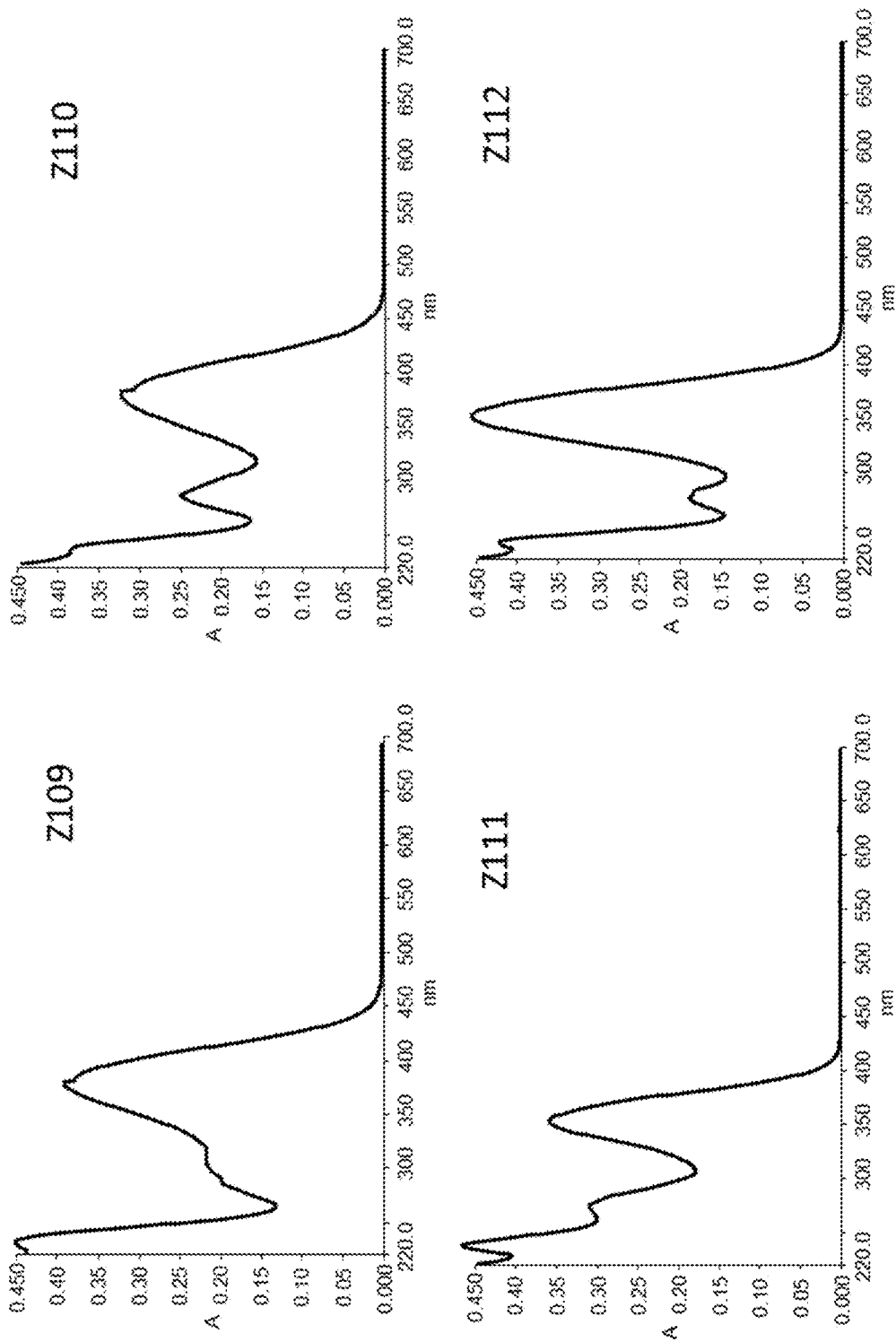
FIG. 6C shows absorption spectra in methanol of additional selected quenchers in accordance with preferred embodiments disclosed herein.
Figure 6D:
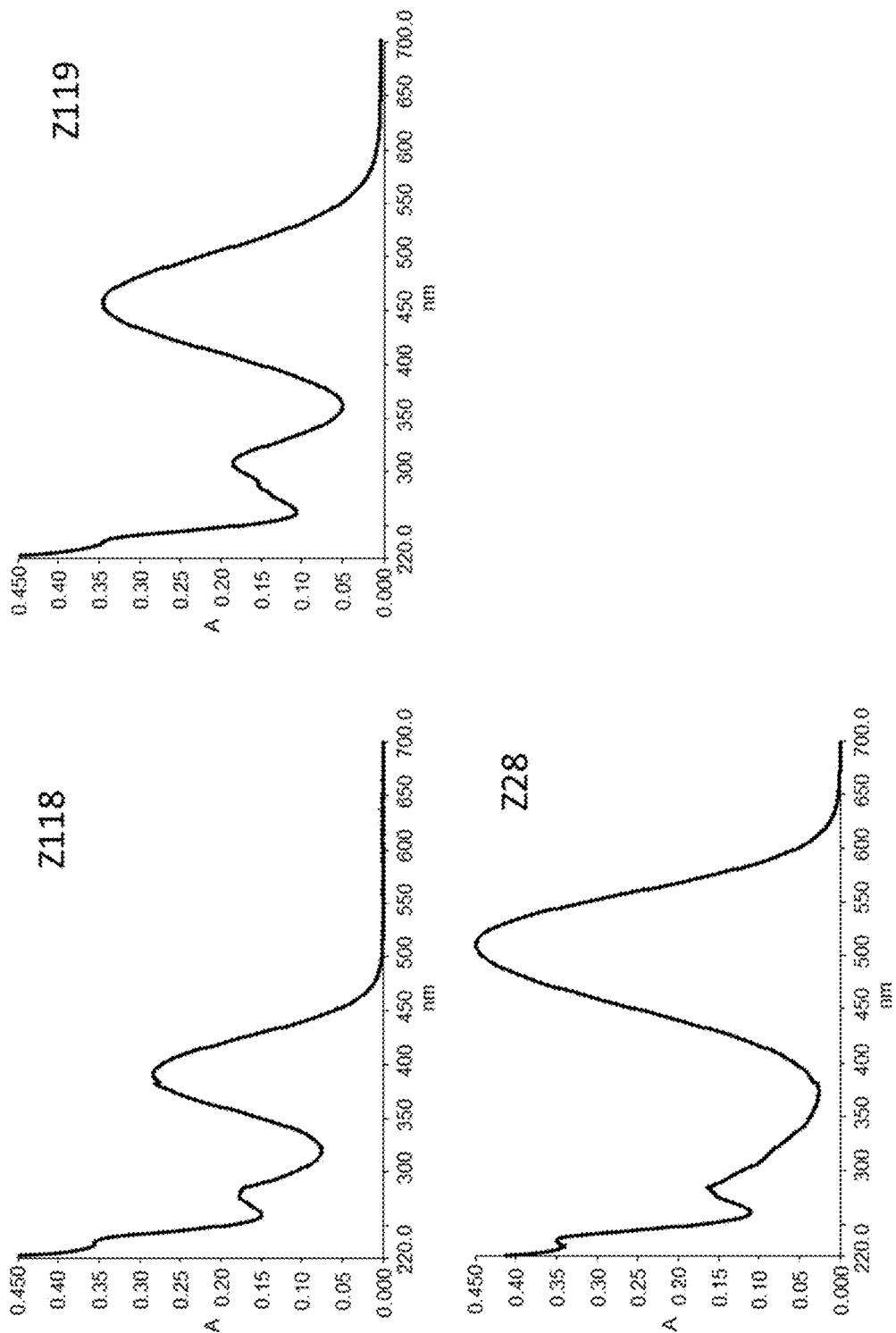
FIG. 6D shows absorption spectra in methanol of selected quenchers in accordance with preferred embodiments disclosed herein

Absorption spectra of various quenchers in accordance with preferred embodiments of the present disclosure, Z98-Z112 as shown in FIG. 5, in methanol were obtained using the instrumentation and measurement conditions described in Table 1 below.

TABLE 1

| Instrumentation and measurement conditions | |
|---|---|
| Instrument | PE Lambda 2S UV-VIS spectrophotometer |
| Conc. (mM) | 0.01-0.03 |
| Solvent | Methanol |
| Temperature (° C.) | Ambient |

FIGS. 6A-6D show the absorption spectra for each exemplary quencher.

Example 35. Oligonucleotide Synthesis

A number of oligonucleotides were synthesized and coupled to MGB, FAM or AP525, and an exemplary quencher in accordance with preferred embodiments of the present disclosure, using the instrumentation and synthesis conditions described in Table 2 below.

TABLE 2

| Instrumentation and synthesis conditions | |
|---|---|
| Instrument | ABI 3900 DNA synthesizer |
| Scale | 200 nmol |
| Deblocking | 3% TCA |
| Amidite conc. | 50 mM (double coupling for all quencher amidites) |
| Activator | 5-Ethylthiotetrazole |
| Oxidation | $I_2$/Pyridine/Water |
| Capping | $Ac_2O$/Pyridine/MeIm |
| Deprotection | conc. $NH_4OH$, 25% EtOH (70° C., 2 h) |
| Purification | 4.6 × 250 mm Luna C18 RP HPLC (2 mL/min, gradient of $CH_3CN$, triethylammonium bicarbonate buffer, pH ~9) |
| Probe concentration determination | $E_{340\ nm} = 72,000\ M^{-1}cm^{-1}$, (measured in 50 mM Tris-HCl pH 8.5) |
| Mass spectroscopy | Thermo Scientific, LCQ Fleet, ESI (TEA-HFIPA buffer) |

The mass spectrometry for the synthesized oligonucleotide probes is listed in Table 3 below.

TABLE 3

Summary of Mass-Spectrometry data for synthesized oligonucleotide probes

| SEQ. ID No. | Sequence (5'-3') | Calc MW | Found MW | % Purity |
|---|---|---|---|---|
| 1 | MGB-FAM-TGTTCCGGAT*A-Z98** | 5655.5 | 5654.7 | 98.61 |
| 2 | MGB-AP525-TGTTCTGGATA-Z98 | 5940.6 | 5939.9 | 97.92 |
| 1 | MGB-FAM-TGTTCCGGAT*A-Z99 | 5642.4 | 5642.0 | 100.00 |
| 2 | MGB-AP525-TGTTCTGGATA-Z99 | 5927.5 | 5927.2 | 97.79 |
| 1 | MGB-FAM-TGTTCCGGAT*A-Z100 | 5729.6 | 5729.1 | 95.81 |
| 2 | MGB-AP525-TGTTCTGGATA-Z100 | 6014.7 | 6014.1 | 99.04 |
| 1 | MGB-FAM-TGTTCCGGAT*A-Z101 | 5719.6 | 5719.3 | 100.00 |
| 2 | MGB-AP525-TGTTCTGGATA-Z101 | 6004.7 | 6004.3 | 100.00 |
| 1 | MGB-FAM-TGTTCCGGAT*A-Z102 | 5757.6 | 5757.8 | 100 |
| 2 | MGB-AP525-TGTTCTGGATA-Z102 | 6042.7 | 6208.5 | 99.15 |
| 1 | MGB-FAM-TGTTCCGGAT*A-Z103 | 5700.4 | 5700.4 | 96.89 |
| 2 | MGB-AP525-TGTTCTGGATA-Z103 | 5985.5 | 6151.2 | 100 |
| 1 | MGB-FAM-TGTTCCGGAT*A-Z104 | 5687.4 | 5687.8 | 98.19 |
| 2 | MGB-AP525-TGTTCTGGATA-Z104 | 5972.5 | 6137.9 | 100 |
| 1 | MGB-FAM-TGTTCCGGAT*A-Z106 | 5717.4 | 5717.1 | 98.61 |
| 2 | MGB-AP525-TGTTCTGGATA-Z106 | 6002.5 | 6167.5 | 98.25 |
| 1 | MGB-FAM-TGTTCCGGAT*A-Z109 | 5655.3 | 5654.7 | 97.59 |
| 2 | MGB-AP525-TGTTCTGGATA-Z109 | 5940.5 | 6105.6 | 93.89 |
| 1 | MGB-FAM-TGTTCCGGAT*A-Z110 | 5705.4 | 5705.2 | 96.22 |
| 2 | MGB-AP525-TGTTCTGGATA-Z110 | 5990.5 | 6155.1 | 96.03 |

TABLE 3-continued

Summary of Mass-Spectrometry data for synthesized oligonucleotide probes

| SEQ. ID No. | Sequence (5'-3') | Calc MW | Found MW | % Purity |
|---|---|---|---|---|
| 1 | MGB-FAM-TGTTCCGGAT*A-Z111 | 5661.4 | 5660.8 | 98.76 |
| 2 | MGB-AP525-TGTTCTGGATA-Z111 | 5946.5 | 6110.3 | 100 |
| 1 | MGB-FAM-TGTTCCGGAT*A-Z112 | 5584.3 | 5584.4 | 98.86 |
| 2 | MGB-AP525-TGTTCTGGATA-Z112 | 5869.4 | 6034.8 | 100 |
| 3 | MGB-FAM-TGTTCCGGAT*A (SEQ ID NO: 3) | 5154 | 5153.8 | 98.04 |
| 4 | MGB-AP525-TGTTCTGGATA (SEQ ID NO: 4) | 5439.1 | 5604.2 | 97.66 |

T*-5-(4-hydroxybutynyl)thymidine
**In Table 3, each probe containing a quencher for evaluation has one of the following sequences: MGB-F-TGTTCCGGAT*A-Q (SEQ ID NO: 1), or MGB-AP-TGTTCTGGATA-Q (SEQ ID NO: 2), wherein MGB is a minor groove binder, F is FAM, AP is AP525, T* is 5-(4-hydroxybutynyl) thymidine, and Q is one of the exemplary quenchers Z98, Z99, Z100, Z101, Z102, Z103, Z104, Z106, Z109, Z110, Z111, or Z112, in accordance with preferred embodiments. The final two probes in Table 3, MGB-FAM-TGTTCCGGAT*A (SEQ ID NO: 3) and MGB-AP525-TGTTCTGGATA (SEQ ID NO: 4), do not contain a quencher.

Example 36. Evaluation of MGB-Fl-5'-ODN-Q Hybridization Probes Containing Examples of Nitrodiarylethene Quenchers This example illustrates the ability of the new quenchers (Z098, Z099, Z100, Z101, Z102, Z103, Z104, Z106, Z109, Z110, Z111, and Z112) to improve background-corrected fluorescence signal in short, 11-mer oligonucleotides as compared to the traditional quencher (Z028). This example also illustrates the ability of the new quenchers to improve background-corrected signal when evaluated with two different fluorophores with different excitation wavelengths (495 and 525 nm).

Figure 7B:
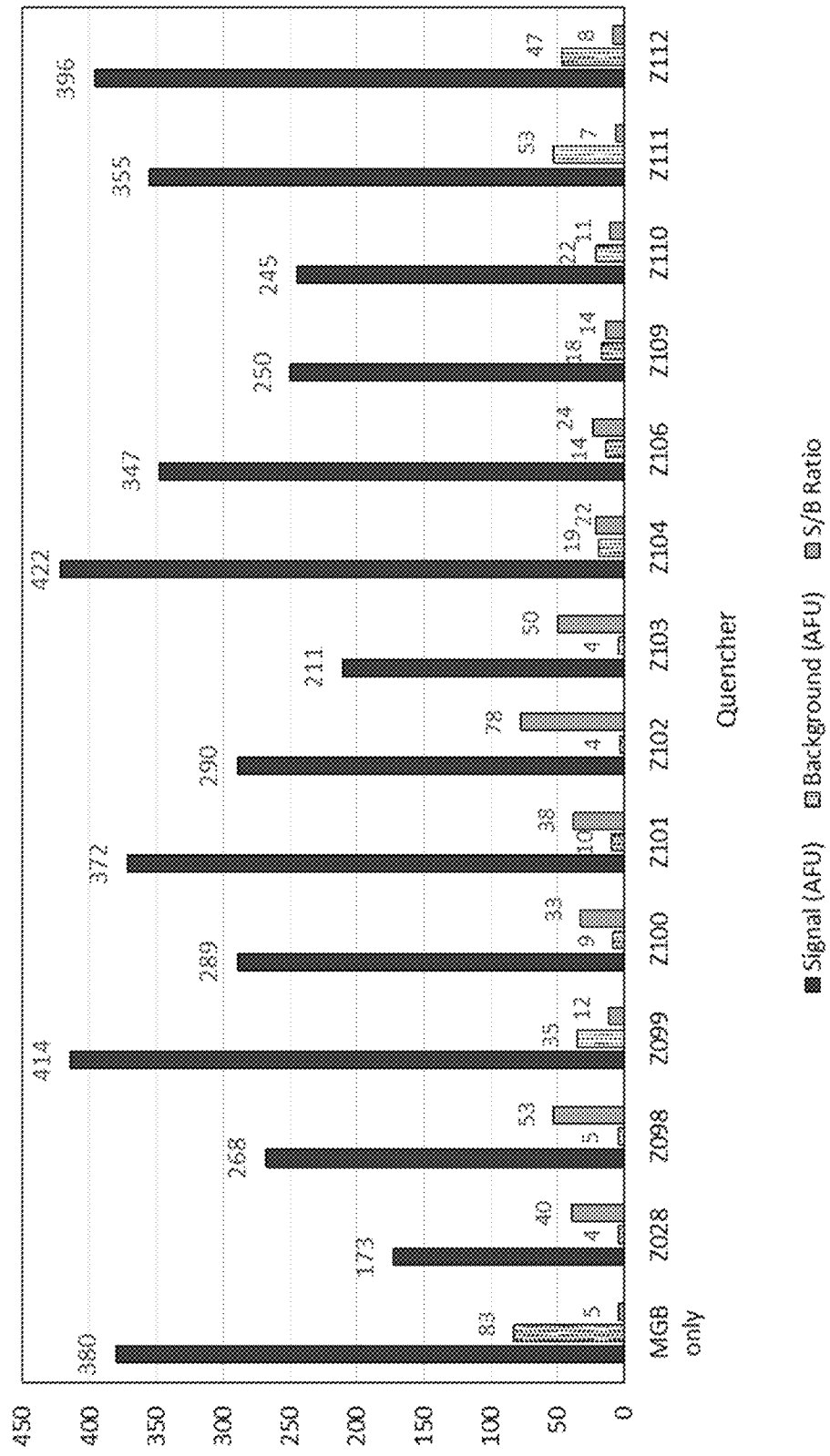
FIG. 7B shows duplex fluorescence (signal), single strand fluorescence (background) and signal-to-background ratio (S/B) of 11-mer Pleaides probes labeled with AP525 and selected quenchers in accordance with preferred embodiments disclosed herein.

To evaluate preferred embodiments of new nitrodiarylethene quenchers (shown in FIG. 5), the duplex fluorescence (Signal), single strand fluorescence (Background) and Signal-to-background ratio (S/B) of two 11-mer Pleaides probes labeled with FAM (or AP525) were investigated. To generate a fluorescent signal the MGB-FAM-5'-TGTTCCGGAT*A-Q (SEQ ID NO:1) or MGB-AP525-5'-TGTTCTGGATA-Q (SEQ ID NO:2) probes (100 nM) were hybridized in a PCR buffer with the 5'-ACTATCCG-GAACAT (SEQ ID NO:5) complement (150 nM) by briefly heating the solution to 80° C. then cooling to 20° C. The probes' sequences were MGB-FAM-5'-TGTTCCGGAT*A-Q (SEQ ID NO:1) and MGB-AP525-5'-TGTTCTGGATA-Q (SEQ ID NO:2). Fluorescence background was measured in the absence of the complement. Results are summarized in FIGS. 7A-7B, which show the improved background-corrected fluorescence signal for the short, 11-mer oligonucleotides containing the new quenchers. Instrumentation and measurement conditions were as shown in Table 4 below.

TABLE 4

Instrumentation and measurement conditions

| | |
|---|---|
| Instrument | Varian Cary Eclipse Fluorimeter |
| Data mode | Fluorescence |

TABLE 4-continued

Instrumentation and measurement conditions

| | |
|---|---|
| Scan mode | Emission |
| X Mode | Wavelength (nm) |
| Ex. Wavelength (nm) | 495 (FAM), 528 (AP525) |
| Em. Wavelength (nm) | 518 (FAM), 550 (AP525) |
| Ex. Slit (nm) | 5 |
| Em. Slit (nm) | 5 |
| Measurement temperature (° C.) | 20.00 |
| 1X PCR buffer | 40 mM NaCl, 10 mM Tris, 5 mM MgCl$_2$, pH 8.9 |

Example 37. Evaluation of Pleiades Probes Labeled with Long-Wavelength Dyes and Nitrodiarylethene Quenchers This example also illustrates the ability of selected new quenchers (Z101 and Z106) to show improvement of background-corrected fluorescence when evaluated with fluorophores with longer emission wavelengths in short, 11-mer oligonucleotides.

Figure 13A:
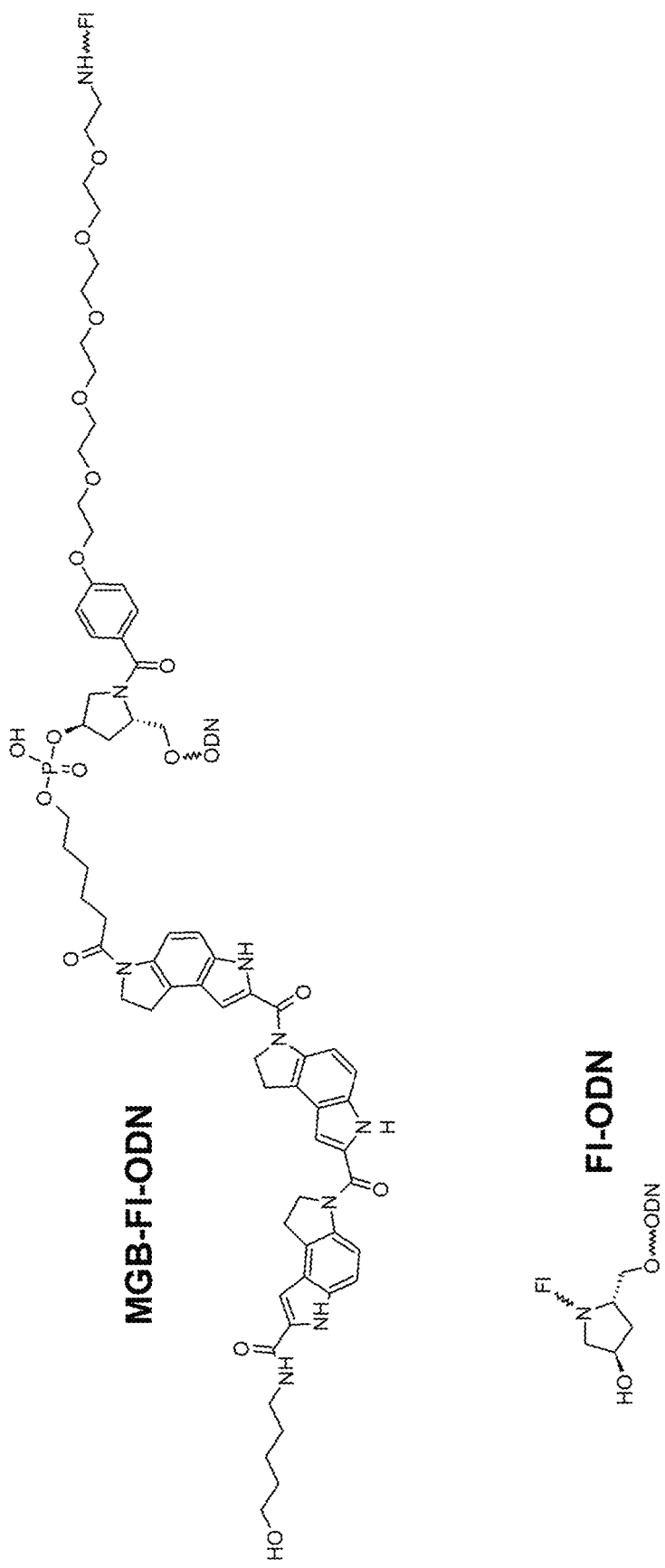
FIG. 13A shows structures of exemplary Fl-ODN and MGB-Fl-ODN.
Figure 13B:
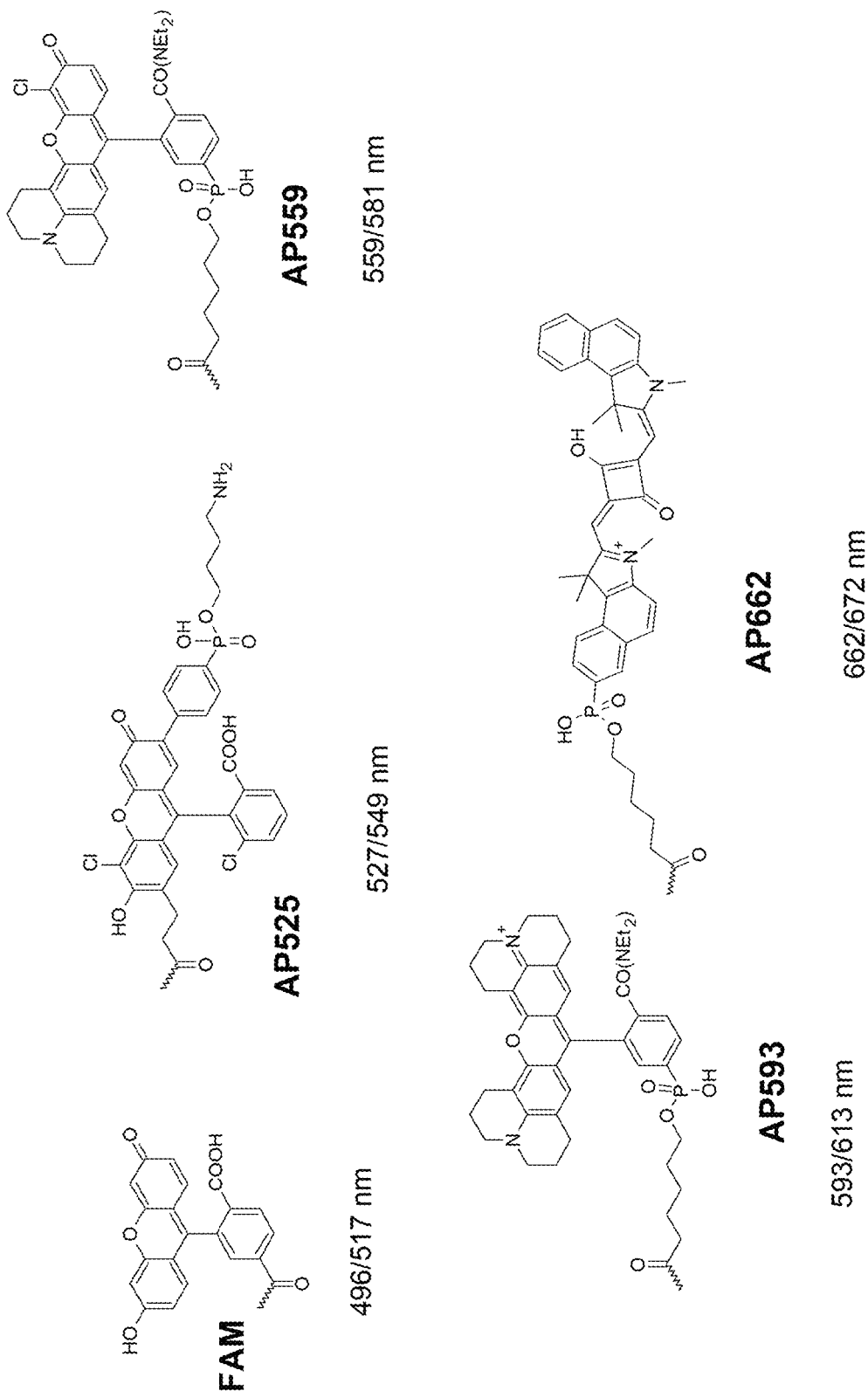
FIG. 13B shows structures of exemplary FAM, AP525, AP559, AP593 and AP662 fluorophores to demonstrate properties of quenchers in accordance with preferred embodiments disclosed herein.

The evaluation was done as described in Example 36. Sequences and experimental details are shown in Table 5 and Table 6 below. The probe sequences were -MGB-Fl-5'-TGTTCCGGAT*A-Q (SEQ ID NO:6) or MGB-Fl-TGT-TCTGGATA-Q (SEQ ID NO:7), where Fl varied as shown in Table 5. To generate fluorescent signal the probe (100 nM) was hybridized in PCR buffer with the 5'-ACTATCCG-GAACAT (SEQ ID NO:5) complement (150 nM). Results are summarized in FIG. 12. Both signal and background values were measured at 20° C. MGB and fluorophore structures are shown in FIG. 13A-13B. Wavelengths under the structures in FIG. 13B indicate the excitation and emission maxima.

TABLE 5

| ODN type | ODN Sequence (5'-3') | Fl | Q |
|---|---|---|---|
| Probe | MGB-Fl-TGTTCCGGAT*A-Q (SEQ ID NO: 6) | FAM, AP525, AP559, AP593, AP662 | Z101, Z106 |
| Probe | MGB-Fl-TGTTCTGGATA-Q (SEQ ID NO: 7) | FAM, AP525, AP559, AP593, AP662 | Z101, Z106 |
| Complement | ACTATCCGGAACAT (SEQ ID NO: 5) | N/A | N/A |

TABLE 6

Instrumentation and measurement conditions

| | |
|---|---|
| Instrument | Varian Cary Eclipse Fluorimeter |
| Data mode | Fluorescence |
| Scan mode | Emission |
| X Mode | Wavelength (nm) |
| Ex. Wavelength (nm) | 495 (FAM), 528 (AP525), 560 (AP559), 595 (AP593), 666(AP662) |
| Em. Wavelength (nm) | 518 (FAM), 550 (AP525), 582 (AP559), 612(AP593), 678 (AP662) |
| Ex. Slit (nm) | 5 |
| Em. Slit (nm) | 5 |
| Measurement temperature (° C.) | 20.00 |
| 1X PCR buffer | 40 mM NaCl, 10 mM Tris, 5 mM MgCl$_2$, pH 8.9 |

TABLE 7

| Probe length (number of bases) | ODN Sequence (5'-3') | 5'-Fluorophore | 3'-Quencher |
|---|---|---|---|
| 10 | TTTTAATTTT (SEQ ID NO: 9) | MGB-AP525 | Z28, Z98, Z99, None (Control) |
| 12 | TTTTTAATTTTT (SEQ ID NO: 10) | MGB-AP525 | Z28, Z98, Z99, None |
| 14 | TTTTTTAATTTTTT (SEQ ID NO: 11) | MGB-AP525 | Z28, Z98, Z99, None |
| 16 | TTTTTTTAATTTTTTT (SEQ ID NO: 12) | MGB-AP525 | Z28, Z98, Z99, None |
| 18 | TTTTTTTTAATTTTTTTT (SEQ ID NO: 13) | MGB-AP525 | Z28, Z98, Z99, None |
| Complement | CCCTCTAAAAAAAAATTAAAAAAAAATCTCCC (SEQ ID NO: 8) | N/A | N/A |

TABLE 8

Instrumentation and measurement conditions

| | |
|---|---|
| Instrument | Varian Cary Eclipse Fluorimeter |
| Data mode | Fluorescence |
| Scan mode | Emission |
| X Mode | Wavelength (nm) |
| Ex. Wavelength (nm) | 525 |
| Em. Wavelength (nm) | 550 |
| Ex. Slit (nm) | 5 |
| Em. Slit (nm) | 5 |
| Measurement temperature (° C.) | Temperature gradient: 20.00-80.00, 1° C./min |
| 1X PCR buffer | 40 mM NaCl, 10 mM Tris, 5 mM MgCl$_2$, pH 8.9 |

Example 38. Evaluation of Fluorescence Properties of Variable Length Pleaides Probes Labeled with the APS25 Fluorophore and Z98 and Z99 Nitrodiarylethene Quenchers This example illustrates (in FIG. 8A-8B) that hybridization signal of short (10-18 mer) probes of Formula IV can be substantially length-independent, provided that a proper quencher-fluorophore combination is chosen.

To generate fluorescent signal the MGB-AP525-5'-ODN-Q or AP525-5'-ODN-Q probes (100 nM) shown in Table 7 below were hybridized in a PCR buffer with the 5'-CCCTCTAAAAAAAAATTAAAAAAAAATCTCCC (SEQ ID NO:8) complement (200 nM) by briefly heating the solution to 80° C. and cooling down to 20° C. Instrumentation and measurement conditions are shown in Table 8. Fluorescence background was measured in the absence of the complement. Results are summarized in FIGS. 8A and 8B.

Example 39. Evaluation of a Molecular Beacon Probe Labeled with APS25 Fluorophore and Different Nitrodiarylethene Quenchers This example illustrates the ability of some quenchers of the disclosure to improve fluorescence signal in a Molecular Beacon probe as compared to a traditional (Z28) quencher.

To evaluate fluorogenic properties of representative nitrodiarylethene quenchers in a Molecular Beacon-like probe design the following oligonucleotides were synthesized as shown in Table 9:

TABLE 9

| ODN Sequence (5'-3')* | 3'-Fluorophore | 5'-Quencher |
|---|---|---|
| <u>ATGT</u>GATTTTT<u>CACAT</u> (SEQ ID NO: 14) | AP525 | Z28, Z98, Z99, Z100, Z103, Z104, Z106 |

*Stem-forming sequence is underlined

Figure 9A:
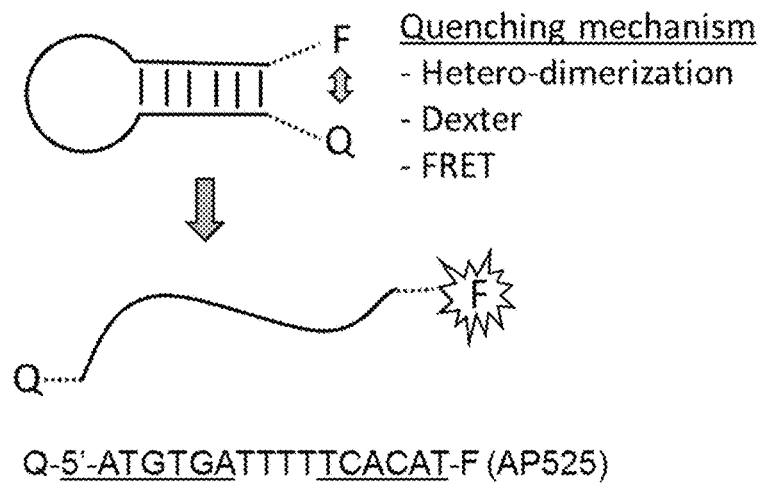
FIG. 9A shows an exemplary structure and mechanism of action of an exemplary Molecular Beacon probe labeled with AP525 fluorophore and different quenchers in accordance with preferred embodiments disclosed herein.
Figure 9B:
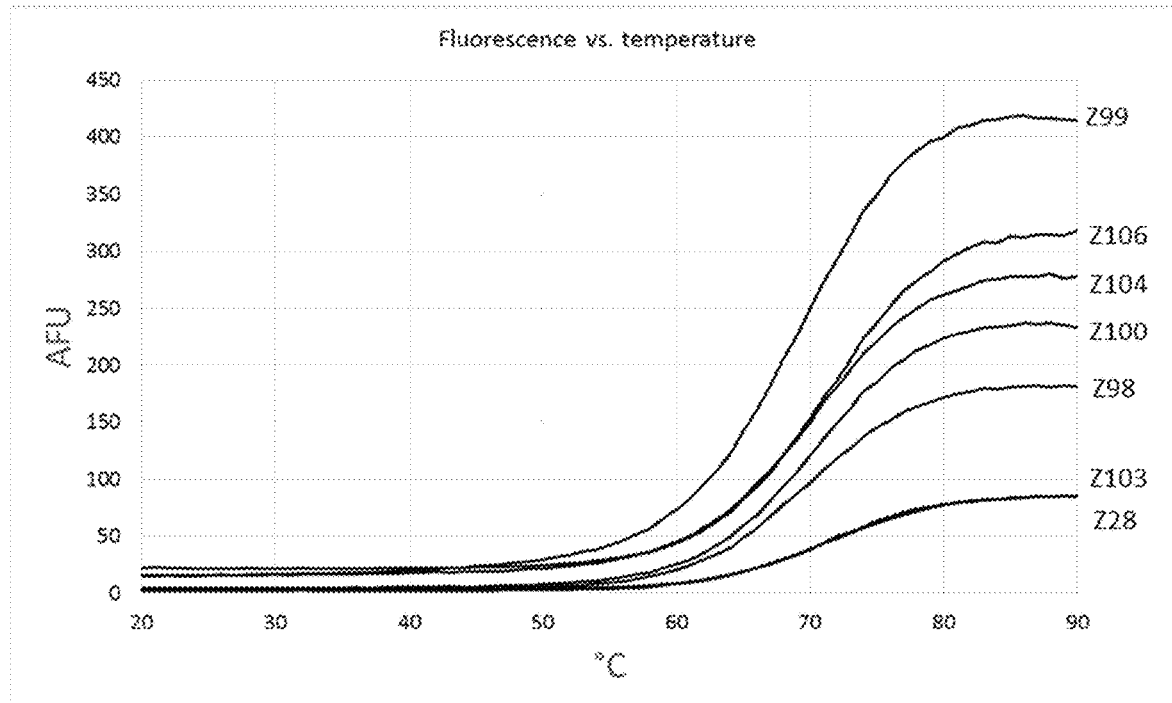
FIG. 9B shows fluorescence versus temperature for probes labeled with different quenchers in accordance with preferred embodiments disclosed herein.

The probes contained a stem-forming sequence, which encouraged the formation of a stem-loop structure (Tm ~70° C.) with the fluorophore and a quencher positioned in close proximity (FIG. 9A). Instrumentation and measurement conditions are shown below in Table 10. Thermal denaturation of the stem lead to separation of the fluorophore and release of fluorescence, shown in FIG. 9B. Background fluorescence (closed form) and Signal (open form) were measured at 20 and 90° C., respectively. Results of the experiment are summarized in FIGS. 10A and 10B.

TABLE 10

Instrumentation and measurement conditions

| Instrument | Varian Cary Eclipse Fluorometer |
|---|---|
| Data mode | Fluorescence |
| Scan mode | Emission |
| X Mode | Wavelength (nm) |
| Ex. Wavelength (nm) | 527 |
| Em. Wavelength (nm) | 549 |
| Ex. Slit (nm) | 5 |
| Em. Slit (nm) | 5 |
| Measurement temperature (° C.) | Temperature gradient: 20.00-90.00, 1° C./min |
| 1X PCR buffer | 40 mM NaCl, 10 mM Tris, 5 mM MgCl$_2$, pH 8.9 |

To determine a possible quenching mechanism, the stem-loop probes were analyzed by UV-VIS spectrometry at 20 and 95° C. using the instrumentation and measurement conditions in Table 11 below. The resulting absorption spectra are summarized in FIG. 11A-11B.

TABLE 11

Instrumentation and measurement conditions

| Instrument | Varian Cary 400 UV-VIS spectrophotometer |
|---|---|
| Conc. (mM) | 1.6 µM |
| Solvent | 1xPCR buffer |
| Measurement temperature (° C.) (high T) | 95.00 |
| Measurement temperature (° C.) (low T) | 20.00 |

REFERENCES CITED

The following documents and publications are hereby incorporated by reference.

U.S. and Foreign Patent Documents

REFERENCES CITED

The following documents and publications are hereby incorporated by reference.

U.S. and Foreign Patent Documents

EP Patent No.
1384789
PCT Patent Publication Nos.
2014/0335515
2013/0030166
U.S. Pat. Nos.
RE 38,416
5,419,966
5,512,667
5,585,481
5,696,251
5,736,626
5,801,155
5,942,610
6,150,097
6,312,894
6,323,337
6,399,392
6,699,661
6,699,975
6,790,945
6,821,727
6,972,339
7,019,129
7,166,715
7,205,105
7,262,007
7,381,818
7,439,341
7, 564,567
7,582,739
7,767,834
7,759,470
7,803,536
7,879,986
8,163,910
8,637,658

Non-Patent References

Ausubel, et al., CURRENT PROTOCOLS IN MOLECULAR BIOLOGY, John Wiley &Sons (1987, 1988, 1989, 1990, 1991, 1992, 1993, 1994, 1995, 1996)

Berge, S. M., et al., Journal of Pharmaceutical Science, 66, 1-19 (1977)

Bonnet et al., Proc. Nat. Acd. SCi USA, 96: 6171-6176 (1999)

Crisalli and Kool, Bioconjug Chem., 22: 2345-54 (2011)

Demidov and Frank-Kamenetskii, TRENDS in Biochemical Sciences, 29: 62-71 (2004)

Eckstein (ed.), OLIGONUCLEOTIDES AND ANALOGUES: A PRACTICAL APPROACH, IRL Press (1991)

Edmonds et al., in Modern Carbonyl Olefination. Ed. T. Takeda, Wiley-VCH Verlag GmbH & Co. KGaA, Weinheim (2004)

Gait (ed.), OLIGONUCLEOTIDE SYNTHESIS: A PRACTICAL APPROACH, IRL Press (1984)

T. W. Greene and P. G. Wuts, Greene's Protective Groups in Organic Chemistry, Wiley, 4nd ed. (2007)

Harrison and Harrison et al., Compendium of Synthetic Organic Methods, Vols. 1-8, John Wiley and Sons. (1971-1996)

Heid et al., Genome Res. 6: 986-994 (2009)

Hermanson, Bioconjugate Techniques, Elsevier (1996)

Johansson et al., J. Am. Chem. Soc., 124: 6950-6956 (2002)

Knemeyer and Marme, DNA & Gene Sequences. 1, No. 2: 145-157 (2007)

Kutyavin et al., Nucl. Acids Res. 28: 655-661 (2000)

Lakowicz, Principles of Fluorescence Spectroscopy, Third Edition, Springer (2007)
Lukhtanov et al., Bioconjugate Chemistry, 6, 418-426 (1995)
Lukhtanov et al., Bioconjug Chem. 7:564-7 (1996)
Lukhtanov et al., Nucl. Acids Res., 35: e30 (2007)
Malicka, J. M. et al., Chemistry—A European Journal, 19: 12991-13001 (2013)
March J., in Advanced Organic Chemistry, Chapter 4", 4th edition John Wiley and Sons, New York (1992)
Maniatis, Fritsch & Sambrook, MOLECULAR CLONING: A LABORATORY MANUAL, Cold Spring Harbor Laboratory Press (1982)
Morrison et al., Anal. Biochem., 183: 231-244 (1998)
Paris et al. Nucleic Acids Res., 38(7): e95 (2010)
Reddy, et al., Pharmacol. Therap., 84:1-111 (1999)
Sambrook, Fritsch & Maniatis, MOLECULAR CLONING: A LABORATORY MANUAL, Second Edition, Cold Spring Harbor Laboratory Press (1989)
Sedlak and Jerome, Diagn Microbiol Infect Dis. 75(1):1-4 (2013)
Tolstrup et al., Nucl. Acids. Res., 31:3758-3762 (2003)
Tyagi et al., Nat Biotechnol., 14; 303-8 (1996)
Tyagi et al., Nat Biotechnol., 16:49-53 (1998)
Walker, et al., Biopolymers, 44:323-334 (1997)
Wemmer, D. E. and Dervan P. B., Current Opinion in Structural Biology, 7:355-361 (1997)
Zimmer, C and Wahnert, U., Prog. Biophys. Molec. Bio. 47:31-112 (1986)

What is claimed is:

1. A quencher reagent for oligonucleotide labeling having the formula:

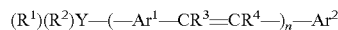

$(R^1)(R^2)Y-(-Ar^1-CR^3=CR^4-)_n-Ar^2$ wherein $Ar^1$ and $Ar^2$ are substituted phenyl, wherein $Ar^1$ and $Ar^2$ are independently substituted with one or more of H, $(C_1-C_8)$alkyl, halogen, alkyloxy, phenyl, or combinations thereof, and at least one of $Ar^1$ and $Ar^2$ is substituted with one or more $NO_2$ groups;

$R^3$ and $R^4$ are independently H or $(C_1-C_8)$ alkyl;

n is from 1 to 3;

Y is a linking group connecting $Ar^1$ with $R^1$ and $R^2$ and having from 1 to 100 main chain atoms selected from C, N, O, S, P and Si, wherein the main chain atom of Y directly connected to $Ar^1$ is selected from N, O, S, or C, and wherein if the main chain atom of Y directly connected to $Ar^1$ is C, the main chain C atom is further directly connected only to C, H, N, S, Si or P;

$R^1$ is a phosphoramidite having the formula —OP$(N(iPr)_2)(OCH_2CH_2CN)$) or a linking group attached to a solid support having the formula —O—C(=O)Z-solid support, wherein iPr is isopropyl, wherein Z is 1 to 30 main chain atoms in length wherein the main chain atoms are selected from C, N, O, P, and S; and $R^2$ is H, or a dimethoxytrityl-protected hydroxyl group.

2. The quencher reagent of claim 1 wherein at least one of $Ar^1$ and $Ar^2$ is substituted with at least two $NO_2$ groups.

3. The quencher reagent of claim 1, wherein Y further comprises acyclic, cyclic, or aromatic groups, or combinations thereof.

4. The quencher reagent of claim 1, wherein Z further comprises acyclic, cyclic, or aromatic groups, or combinations thereof.

5. A method for preparing an oligonucleotide conjugate labeled with a quencher, comprising:

reacting an oligonucleotide with the quencher reagent of claim 1 to produce an oligonucleotide conjugate labeled with a quencher.

6. A quencher reagent for oligonucleotide labeling having the formula:

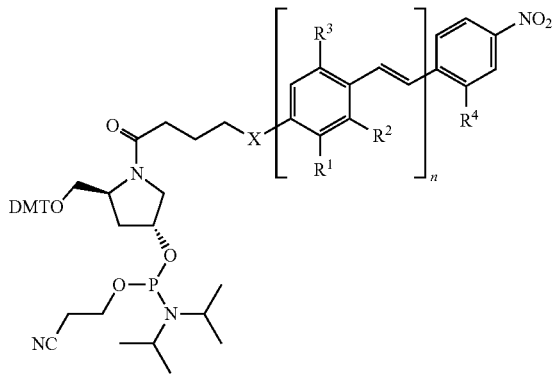

wherein DMT is dimethoxytrityl, $R^1$ is H or OMe, $R^2$ is H, or $R^1$ and $R^2$ are each —CH=CH— and link together to form an aromatic group, $R^3$ is H or OMe, $R^4$ is H, $NO_2$, or Cl, n is 1 or 2, and X is N(Me), N(Et), or O.

7. A method for preparing an oligonucleotide conjugate labeled with a quencher, comprising:

reacting an oligonucleotide with the quencher reagent of claim 6 produce an oligonucleotide conjugate labeled with a quencher.

* * * * *

UNITED STATES PATENT AND TRADEMARK OFFICE
CERTIFICATE OF CORRECTION

PATENT NO. : 10,738,346 B2
APPLICATION NO. : 15/909096
DATED : August 11, 2020
INVENTOR(S) : Eugeny A. Lukhtanov et al.

Page 1 of 1

It is certified that error appears in the above-identified patent and that said Letters Patent is hereby corrected as shown below:

In the Specification
In Column 7, Line 7, delete ""Super A®:" and insert -- "Super A®: --, therefor.
In Column 7, Line 9, delete ""Super G":" and insert -- "Super G®: --, therefor.
In Column 7, Line 10, delete ""Super T":" and insert -- "Super T®: --, therefor.
In Column 11, Lines 37-51, delete " 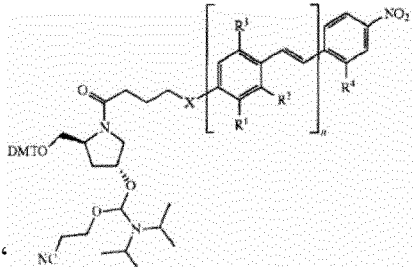 " and insert
-- 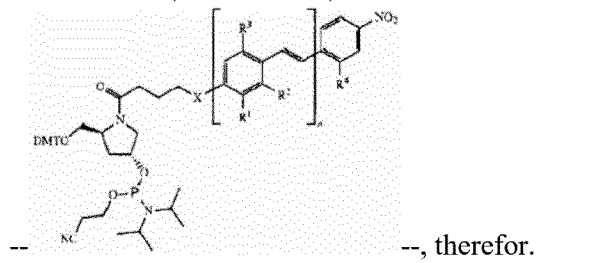 --, therefor.
In Column 12, Line 23, delete "g1." and insert -- g11. --, therefor.
In Column 17, Line 63, delete "J1-8.7 Hz," and insert -- J1=8.7 Hz, --, therefor.
In Column 19, Line 3, delete "J22 Hz 1H)," and insert -- J2~2 Hz, 1H), --, therefor.
In Column 20, Line 11, delete "J22 Hz 1H)," and insert -- J2~2 Hz, 1H), --, therefor.

Signed and Sealed this
Tenth Day of August, 2021

Drew Hirshfeld
*Performing the Functions and Duties of the
Under Secretary of Commerce for Intellectual Property and
Director of the United States Patent and Trademark Office*

```
                            SEQUENCE LISTING

<160> NUMBER OF SEQ ID NOS: 14

<210> SEQ ID NO 1
<211> LENGTH: 11
<212> TYPE: DNA
<213> ORGANISM: Artificial Sequence
<220> FEATURE:
<223> OTHER INFORMATION: Probe sequence
<220> FEATURE:
<221> NAME/KEY: m
<222> LOCATION: (1)..(1)
<223> OTHER INFORMATION: m is T attached to MGB and FAM
<220> FEATURE:
<221> NAME/KEY: m
<222> LOCATION: (10)..(10)
<223> OTHER INFORMATION: m is 5-(4-hydroxybutynyl)thymidine
<220> FEATURE:
<221> NAME/KEY: m
<222> LOCATION: (11)..(11)
<223> OTHER INFORMATION: m is A attached to exemplary quencher Z98, Z99,
      Z100, Z101, Z102, Z103, Z104, Z106, Z109, Z110, Z111, or Z112

<400> SEQUENCE: 1
mgttccggam m                                                          11

<210> SEQ ID NO 2
<211> LENGTH: 11
<212> TYPE: DNA
<213> ORGANISM: Artificial Sequence
<220> FEATURE:
<223> OTHER INFORMATION: Probe sequence
<220> FEATURE:
<221> NAME/KEY: m
<222> LOCATION: (1)..(1)
<223> OTHER INFORMATION: m is T attached to MGB and AP525
<220> FEATURE:
<221> NAME/KEY: m
<222> LOCATION: (11)..(11)
<223> OTHER INFORMATION: m is A attached to exemplary quencher Z98, Z99,
      Z100, Z101, Z102, Z103, Z104, Z106, Z109, Z110, Z111, or Z112

<400> SEQUENCE: 2
mgttctggat m                                                          11

<210> SEQ ID NO 3
<211> LENGTH: 11
<212> TYPE: DNA
<213> ORGANISM: Artificial Sequence
<220> FEATURE:
<223> OTHER INFORMATION: Probe sequence
<220> FEATURE:
<221> NAME/KEY: m
<222> LOCATION: (1)..(1)
<223> OTHER INFORMATION: m is T attached to MGB and FAM
<220> FEATURE:
```

```
<221> NAME/KEY: m
<222> LOCATION: (10)..(10)
<223> OTHER INFORMATION: m is 5-(4-hydroxybutynyl)thymidine

<400> SEQUENCE: 3
mgttccggam a                                                             11

<210> SEQ ID NO 4
<211> LENGTH: 11
<212> TYPE: DNA
<213> ORGANISM: Artificial Sequence
<220> FEATURE:
<223> OTHER INFORMATION: Probe sequence
<220> FEATURE:
<221> NAME/KEY: m
<222> LOCATION: (1)..(1)
<223> OTHER INFORMATION: m is T attached to MGB and AP525

<400> SEQUENCE: 4
mgttctggat a                                                             11

<210> SEQ ID NO 5
<211> LENGTH: 14
<212> TYPE: DNA
<213> ORGANISM: Artificial Sequence
<220> FEATURE:
<223> OTHER INFORMATION: Complement sequence

<400> SEQUENCE: 5
actatccgga acat                                                          14

<210> SEQ ID NO 6
<211> LENGTH: 11
<212> TYPE: DNA
<213> ORGANISM: Artificial Sequence
<220> FEATURE:
<223> OTHER INFORMATION: Probe sequence
<220> FEATURE:
<221> NAME/KEY: m
<222> LOCATION: (1)..(1)
<223> OTHER INFORMATION: m is T attached to MGB and one fluorophore of
      FAM, AP525, AP559, AP593, or AP662
<220> FEATURE:
<221> NAME/KEY: m
<222> LOCATION: (10)..(10)
<223> OTHER INFORMATION: m is 5-(4-hydroxybutynyl)thymidine
<220> FEATURE:
<221> NAME/KEY: m
<222> LOCATION: (11)..(11)
<223> OTHER INFORMATION: m is A attached to exemplary quencher Z101 or
      Z106

<400> SEQUENCE: 6
mgttccggam m                                                             11

<210> SEQ ID NO 7
<211> LENGTH: 11
<212> TYPE: DNA
<213> ORGANISM: Artificial Sequence
<220> FEATURE:
<223> OTHER INFORMATION: Probe sequence
<220> FEATURE:
<221> NAME/KEY: m
<222> LOCATION: (1)..(1)
<223> OTHER INFORMATION: m is T attached to MGB and one fluorophore of
      FAM, AP525, AP559, AP593, or AP662
<220> FEATURE:
<221> NAME/KEY: m
<222> LOCATION: (11)..(11)
<223> OTHER INFORMATION: m is A attached to exemplary quencher Z101 or
      Z106
```

```
<400> SEQUENCE: 7
mgttctggat m                                                            11

<210> SEQ ID NO 8
<211> LENGTH: 32
<212> TYPE: DNA
<213> ORGANISM: Artificial Sequence
<220> FEATURE:
<223> OTHER INFORMATION: Complement sequence

<400> SEQUENCE: 8
ccctctaaaa aaaaattaaa aaaaaatctc cc                                     32

<210> SEQ ID NO 9
<211> LENGTH: 10
<212> TYPE: DNA
<213> ORGANISM: Artificial Sequence
<220> FEATURE:
<223> OTHER INFORMATION: Probe sequence with 5' attached MGB and AP525
      and 3' attached quencher Z28, Z98, Z99, or no quencher

<400> SEQUENCE: 9
ttttaatttt                                                              10

<210> SEQ ID NO 10
<211> LENGTH: 12
<212> TYPE: DNA
<213> ORGANISM: Artificial Sequence
<220> FEATURE:
<223> OTHER INFORMATION: Probe sequence with 5' attached MGB and AP525
      and 3' attached quencher Z28, Z98, Z99, or no quencher

<400> SEQUENCE: 10
tttttaattt tt                                                           12

<210> SEQ ID NO 11
<211> LENGTH: 14
<212> TYPE: DNA
<213> ORGANISM: Artificial Sequence
<220> FEATURE:
<223> OTHER INFORMATION: Probe sequence with 5' attached MGB and AP525
      and 3' attached quencher Z28, Z98, Z99, or no quencher

<400> SEQUENCE: 11 tttttaatt tttt                                                          14

<210> SEQ ID NO 12
<211> LENGTH: 16
<212> TYPE: DNA
<213> ORGANISM: Artificial Sequence
<220> FEATURE:
<223> OTHER INFORMATION: Probe sequence with 5' attached MGB and AP525
      and 3' attached quencher Z28, Z98, Z99, or no quencher

<400> SEQUENCE: 12
tttttttaat tttttt                                                       16

<210> SEQ ID NO 13
<211> LENGTH: 18
<212> TYPE: DNA
<213> ORGANISM: Artificial Sequence
<220> FEATURE:
<223> OTHER INFORMATION: Probe sequence with 5' attached MGB and AP525
      and 3' attached quencher Z28, Z98, Z99, or no quencher

<400> SEQUENCE: 13
```

```
tttttttaa ttttttt                                                    18

<210> SEQ ID NO 14
<211> LENGTH: 16
<212> TYPE: DNA
<213> ORGANISM: Artificial Sequence
<220> FEATURE:
<223> OTHER INFORMATION: Probe sequence with 3' attached AP525 and 5'
      attached quencher Z28, Z98, Z99, Z100, Z103, Z104, or Z106

<400> SEQUENCE: 14
atgtgatttt tcacat                                                    16
```